(12) United States Patent
Chin et al.

(10) Patent No.: US 9,375,145 B2
(45) Date of Patent: Jun. 28, 2016

(54) SYSTEMS AND METHODS FOR CONTROLLING ACQUISITION OF SENSOR INFORMATION

(71) Applicant: Elwha LLC, Bellevue, WA (US)

(72) Inventors: Hon Wah Chin, Palo Alto, CA (US); Roderick A. Hyde, Redmond, WA (US); Robert C. Petroski, Seattle, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 725 days.

(21) Appl. No.: 13/720,635

(22) Filed: Dec. 19, 2012

(65) Prior Publication Data

US 2014/0171749 A1    Jun. 19, 2014

(51) Int. Cl.
*A61B 5/00* (2006.01)
*A61B 5/0205* (2006.01)

(52) U.S. Cl.
CPC ........... *A61B 5/0015* (2013.01); *A61B 5/02055* (2013.01); *A61B 5/7221* (2013.01); *A61B 5/7275* (2013.01); *A61B 5/002* (2013.01); *A61B 5/0022* (2013.01)

(58) Field of Classification Search
CPC .... A61B 5/024; A61B 5/0402; A61B 5/0002; A61B 5/0245; A61B 5/0015; A61B 5/7221; A61B 5/02055; A61B 5/7275
USPC ......................................... 600/301, 509, 527
See application file for complete search history.

(56) References Cited

U.S. PATENT DOCUMENTS

| | | |
|---|---|---|
| 5,571,152 A | 11/1996 | Chen et al. |
| 6,210,326 B1 | 4/2001 | Ehwald |
| 6,234,973 B1 | 5/2001 | Meador et al. |
| 6,268,161 B1 | 7/2001 | Han et al. |
| 6,280,604 B1 | 8/2001 | Allen et al. |
| 6,514,689 B2 | 2/2003 | Han et al. |
| 6,823,717 B2 | 11/2004 | Porter et al. |

(Continued)

FOREIGN PATENT DOCUMENTS

| | | |
|---|---|---|
| WO | WO 03/048789 A2 | 6/2003 |
| WO | WO 2006/091123 A1 | 8/2006 |

OTHER PUBLICATIONS

PCT International Search Report; International App. No. PCT/US2013/075745; May 22, 2014; pp. 1-2.

(Continued)

*Primary Examiner* — Theodore Stigell
*Assistant Examiner* — Michael Carey

(57) ABSTRACT

Systems and methods are described for controlling acquisition of sensor information, including: one or more condition sensors, one or more physiological sensors, and a computing device including a processor programmed to query the condition sensors to initiate measurement of one or more conditions of an individual relative to the one or more physiological sensors; receive a set of condition sensor values from the condition sensors; assign a predictive value to the set of condition sensors values; query at least one of the one or more physiological sensors to measure one or more physiological parameters of the individual if the assigned predictive value of the set of condition sensor values meets or exceeds a minimum predictive value threshold; and re-query at least one of the one or more condition sensors if the assigned predictive value of the set of condition sensors fails to meet or exceed the minimum predictive value threshold.

39 Claims, 24 Drawing Sheets

(56) References Cited

U.S. PATENT DOCUMENTS

| | | | |
|---|---|---|---|
| 6,994,934 B2 | 2/2006 | Stanish et al. | |
| 7,168,294 B2 | 1/2007 | Porter et al. | |
| 7,173,437 B2 | 2/2007 | Hervieux et al. | |
| 7,189,471 B2 | 3/2007 | Jankowski et al. | |
| 7,194,801 B2 | 3/2007 | Jenson et al. | |
| 7,205,701 B2 | 4/2007 | Liu et al. | |
| 7,218,900 B2 | 5/2007 | Suzuki | |
| 7,227,956 B1 | 6/2007 | Onishi | |
| 7,236,595 B1 | 6/2007 | Bean et al. | |
| 7,238,628 B2 | 7/2007 | Demaray et al. | |
| 7,245,894 B2 | 7/2007 | Sekiguchi et al. | |
| 7,245,956 B2 | 7/2007 | Matthews et al. | |
| 7,254,160 B2 | 8/2007 | Kawamoto et al. | |
| 7,260,155 B2 | 8/2007 | Stonick et al. | |
| 7,272,431 B2 | 9/2007 | McGrath | |
| 7,294,105 B1 * | 11/2007 | Islam | A61B 5/0006 128/903 |
| 7,340,293 B2 | 3/2008 | McQuilkin | |
| 7,396,333 B2 | 7/2008 | Stahmann et al. | |
| 7,725,150 B2 | 5/2010 | Tupin, Jr. et al. | |
| 2006/0058694 A1 | 3/2006 | Clark et al. | |
| 2006/0190419 A1 | 8/2006 | Bunn et al. | |
| 2007/0167850 A1 * | 7/2007 | Russell | A61B 5/0205 600/513 |
| 2007/0265509 A1 | 11/2007 | Burch et al. | |
| 2008/0007445 A1 | 1/2008 | Leach, Jr. et al. | |
| 2008/0039698 A1 | 2/2008 | Burton | |
| 2008/0045832 A1 | 2/2008 | McGrath | |
| 2008/0221401 A1 | 9/2008 | Derchak et al. | |
| 2008/0246495 A1 | 10/2008 | Zarabadi et al. | |
| 2009/0118590 A1 * | 5/2009 | Teller | A61B 5/411 600/300 |
| 2010/0049045 A1 | 2/2010 | Matsumura et al. | |
| 2010/0174533 A1 | 7/2010 | Pakhomov | |
| 2010/0249541 A1 | 9/2010 | Geva et al. | |
| 2012/0179020 A1 | 7/2012 | Wekell | |
| 2012/0256769 A1 | 10/2012 | Satpathy | |

OTHER PUBLICATIONS

Avagyan et al.; "New Diagnostic Methods in Acupuncture"; Diagnostics in TCM; http://www.acutechinternational.com/html/diagnostics.html; May 1, 2012; pp. 1.

Franceschini et al.; "Near-infrared spiroximetry: noninvasive measurements of venous saturation in piglets and human subjects"; Journal of Applied Physiology; 2002; p. 372-384; vol. 92; American Physiological Society.

Ghaemmaghami et al.; "Normal Probability Testing of Snore Signals for Diagnosis of Obstructive Sleep Apnea", 31$^{st}$ Annual International Conference of the IEEE EMBS; Sep. 2-6, 2009; pp. 5551-5554; IEEE; Minneapolis, Minnesota.

Harland et al.; "High resolution ambulatory electrocardiographic monitoring using wrist-mounted electric potential sensors"; Measurement Science and Technology; 2003; pp. 923-928; vol. 14; IOP Publishing Ltd; UK.

Hunt et al.; "2009 Focused Update Incorporated Into the ACC/AHA 2005 Guidelines for the Diagnosis and Management of Heart Failure in Adults"; Circulation; 2009; pp. e390-e480; American Heart Association, Inc.; Dallas, TX.

Kedar et al.; "Non-line-of-sight optical wireless sensor network operating in multiscattering channel"; Applied Optics; Nov. 20, 2006; pp. 8454-8461; vol. 45; No. 33; Optical Society of America.

Michahelles et al.; "Less Contact: Heart-rate detection without even touching the user"; Proceedings of the Eighth International Symposium on Wearable Computers (ISWC'04); pp. 1-4; IEEE Computer Society.

Obeid et al.; "A Tunable System for Contact-less Heartbeat Detection and a Modeling Approach"; IEEE; 2009; pp. 1-4; IEEE.

Pathan et al.; "Security in Wireless Sensor Networks: Issues and Challenges"; ICACT; Feb. 20-22, 2006; pp. 1043-1048.

Prance et al.; "Adaptive Electric Potential Sensors for Smart Signal Acquisition and Processing"; Sensors and their Applications XIV (Sensors07), Journal of Physics: Conference Series 76; 2007; pp. 1-5; IOP Publishing Ltd.

Raja et al., "Changes in tissue water content measured with multiple-frequency bioimpedance and metabolism measured with $^{31}$P-MRS during progressive forearm exercise"; Journal of Applied Physiology; Jun. 22, 2006; pp. 1070-1075; vol. 101; 2006 the American Physiological Society.

Rivera et al.; "Multi-target estimation of heart and respiration rates using ultra wideband sensors"; printed on Nov. 29, 2012; pp. 1-6.

Shamsham et al.; "Essentials of the Diagnosis of Heart Failure"; Am Fam Physician, http://www.aafp.org/afp/2000/0301/p1319. html?printable=afp; Mar. 1, 2000; pp. 1319-1328, 15 pages total; vol. 61; No. 5.

Staderini, Enrico M.; "UWB Radars in Medicine"; IEEE AESS Systems Magazine; Jan. 2002; pp. 13-18; 2002 IEEE.

Thiel et al., "Ultra-Wideband Sensors for Improved Magnetic Resonance Imaging, Cardiovascular Monitoring and Tumour Diagnostics"; Sensors; 2010; pp. 10778-10802; vol. 10.

Tu et al.; "A Novel Electrochemical Microsensor for Nitric Oxide Based on Electropolymerized Film of o-Aminobenzaldehydethylene-diamine Nickel"; Electroanalysis; 1999; pp. 70-74; vol. 11; No. 1; WILEY-VCH; Weinheim, Germany.

* cited by examiner

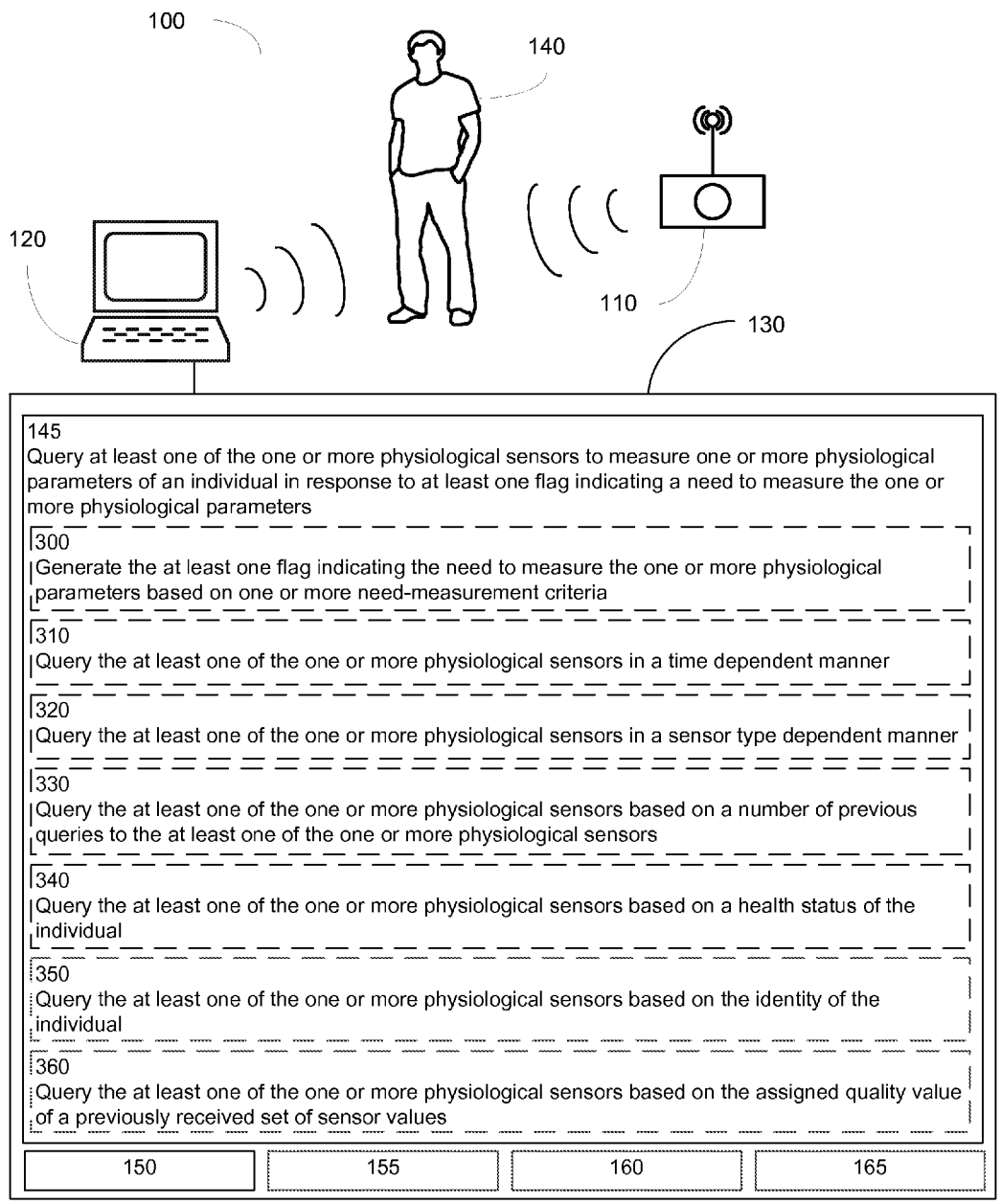

FIG. 4

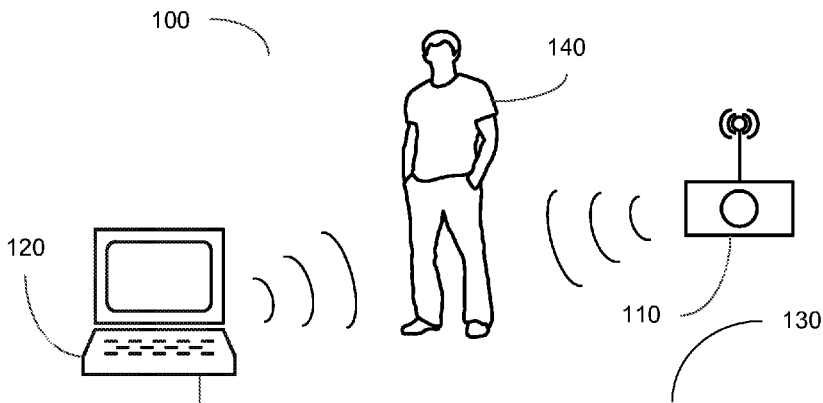

145

150
Receive a set of sensor values from the at least one of the one or more physiological sensors, the set of sensor values representative of the measured one or more physiological parameters 400
Receive the set of sensor values through a wireless transmission 410
Receive the set of sensor values through a wired transmission 155
Assign a quality value to the set of sensor values received from the at least one of the one or more physiological sensors 420
Assign the quality value to the set of physiological sensor values by comparing the set of physiological sensor values with a set standard values 430
A set of standard values with defined signal-to-noise ratio 440
A set of standard values representing a relevant range of values for a specific physiological parameter 450
A set of standard values specific for a physiological sensor type

| 160 | 165 |

FIG. 5

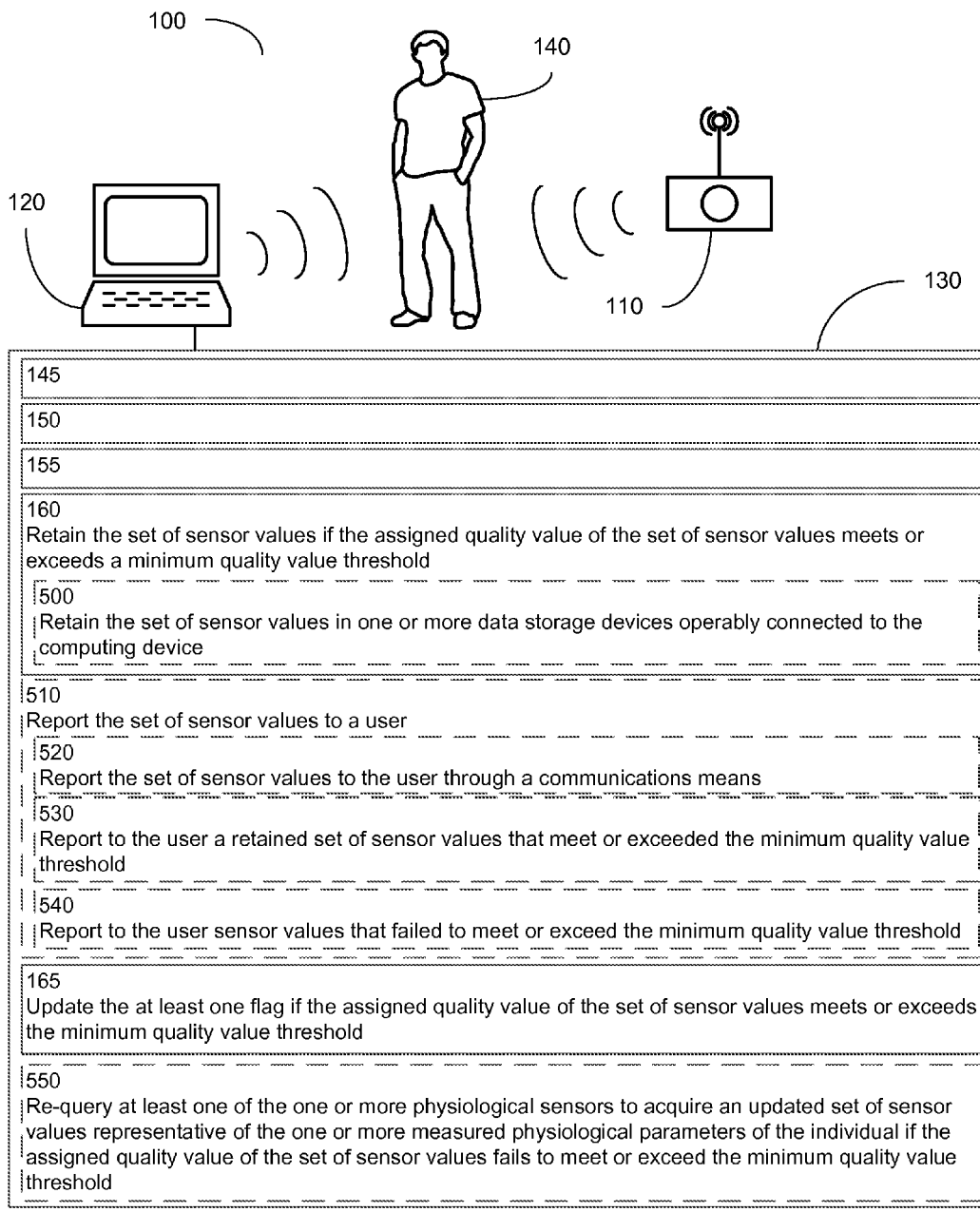

145

150

155

160
Retain the set of sensor values if the assigned quality value of the set of sensor values meets or exceeds a minimum quality value threshold 500
Retain the set of sensor values in one or more data storage devices operably connected to the computing device 510
Report the set of sensor values to a user 520
Report the set of sensor values to the user through a communications means 530
Report to the user a retained set of sensor values that meet or exceeded the minimum quality value threshold 540
Report to the user sensor values that failed to meet or exceed the minimum quality value threshold 165
Update the at least one flag if the assigned quality value of the set of sensor values meets or exceeds the minimum quality value threshold 550
Re-query at least one of the one or more physiological sensors to acquire an updated set of sensor values representative of the one or more measured physiological parameters of the individual if the assigned quality value of the set of sensor values fails to meet or exceed the minimum quality value threshold

700
Generating at least one flag indicating a need to measure one or more physiological parameters of an individual based on one or more need-measurement criteria 800
Wherein the one or more need-measurement criteria include a time of day 810
Wherein the one or more need-measurement criteria include a number of sensor values needed over a given time frame for a reliable diagnosis 820
Wherein the one or more need-measurement criteria include a number of sensor values with assigned quality values that meet the minimum quality value threshold 830
Wherein the one or more need-measurement criteria include a health status of the individual 840
Wherein the one or more need-measurement criteria are updateable 850
Wherein the one or more need-measurement criteria are part of a monitoring schedule 710
Querying one or more physiological sensors in response to the at least one flag 720
Receiving a set of sensor values from the one or more physiological sensors, the set of sensor values representative of one or more physiological parameters of an individual 730
Assigning a quality value to the set of sensor values received from the one or more physiological sensors 740
Retaining the set of sensor values if the assigned quality value of the set of sensor values meets or exceeds a minimum quality value threshold 750
Updating the at least one flag if the assigned quality value of the set of sensor values meets or exceeds the minimum quality value threshold

FIG. 9

| 700 |
|---|

| 710 Querying one or more physiological sensors in response to the at least one flag |
|---|
| 900 Querying the one or more physiological sensors through one or more wireless transmissions |
| 910 Querying the one or more physiological sensors in a time dependent manner |
| 920 Querying the one or more physiological sensors in a sensor type dependent manner |
| 930 Querying the one or more physiological sensors based on identity of the individual |
| 940 Querying the one or more physiological sensors based on a number of previous queries to at least one of the one or more physiological sensors |
| 950 Querying the one or more physiological sensors based on the assigned quality value of a previously received set of sensor values |
| 960 Querying the one or more physiological sensors based on a health status of the individual |
| 970 Querying one or more non-contact physiological sensors |
| 980 Querying one or more of an audio sensor, an image capture device, a micro impulse radar-based sensor, an ultra-wideband radar-based sensor, or a thermal sensor |
| 990 Querying one or more physiological sensors associated with one or more items in a residential space |

| 720 |
|---|

| 730 |
|---|

| 740 |
|---|

| 750 |
|---|

FIG. 10

| 700 |
|---|

| 710 |
|---|

720
Receiving a set of sensor values from the one or more physiological sensors, the set of sensor values representative of one or more physiological parameters of an individual > 1000
> Receiving the set of sensor values through one or more wireless transmissions > 1010
> Receiving the set of sensor values through one or more wired transmissions > 1020
> Receiving the set of sensor values from one or more non-contact physiological sensors > 1030
> Receiving the set of sensor values from one or more audio sensors > 1040
> Receiving the set of sensor values from one or more image capture devices > 1050
> Receiving the set of sensor values from one or more micro impulse radar-based sensors > 1060
> Receiving the set of sensor values from one or more thermal sensors > 1070
> Receiving the set of sensor values from one or more ultra-wideband radar-based sensors > 1080
> Receiving the set of sensor values from one or more physiological sensors associated with one or more items in a residential space

| 730 |
|---|

| 740 |
|---|

| 750 |
|---|

FIG. 13

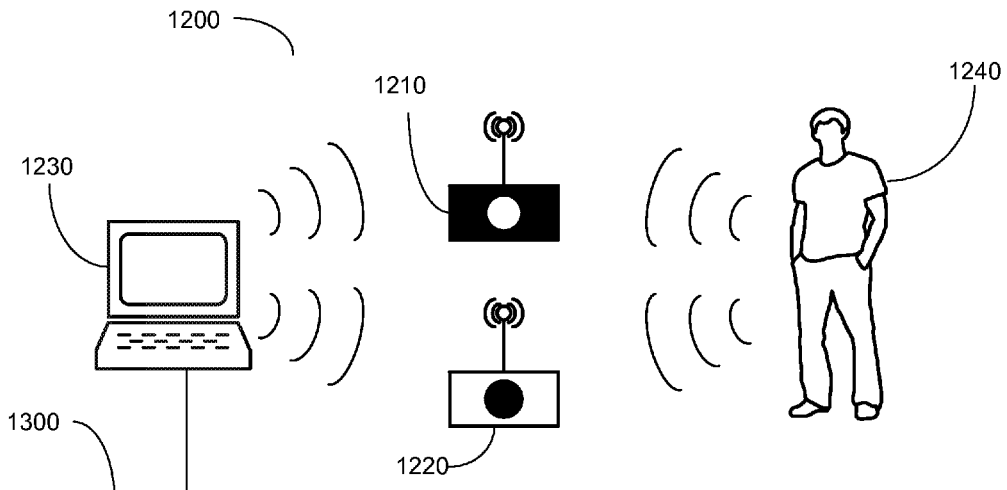

1310
Query at least one of the one or more condition sensors to initiate measurement of one or more conditions of an individual relative to the one or more physiological sensors 1320
Receive a set of condition sensor values from the at least one of one or more condition sensors, the set of condition sensor values representative of the one or more conditions of the individual relative to the one or more physiological sensors 1330
Assign a predictive value to the set of condition sensor values 1340
Query at least one of the one or more physiological sensors to measure one or more physiological parameters of the individual if the assigned predictive value of the set of condition sensor values meets or exceeds a minimum predictive value threshold 1350
Re-query at least one of the one or more condition sensors if the assigned predictive value of the set of condition sensors values fails to meet or exceed the minimum predictive value threshold

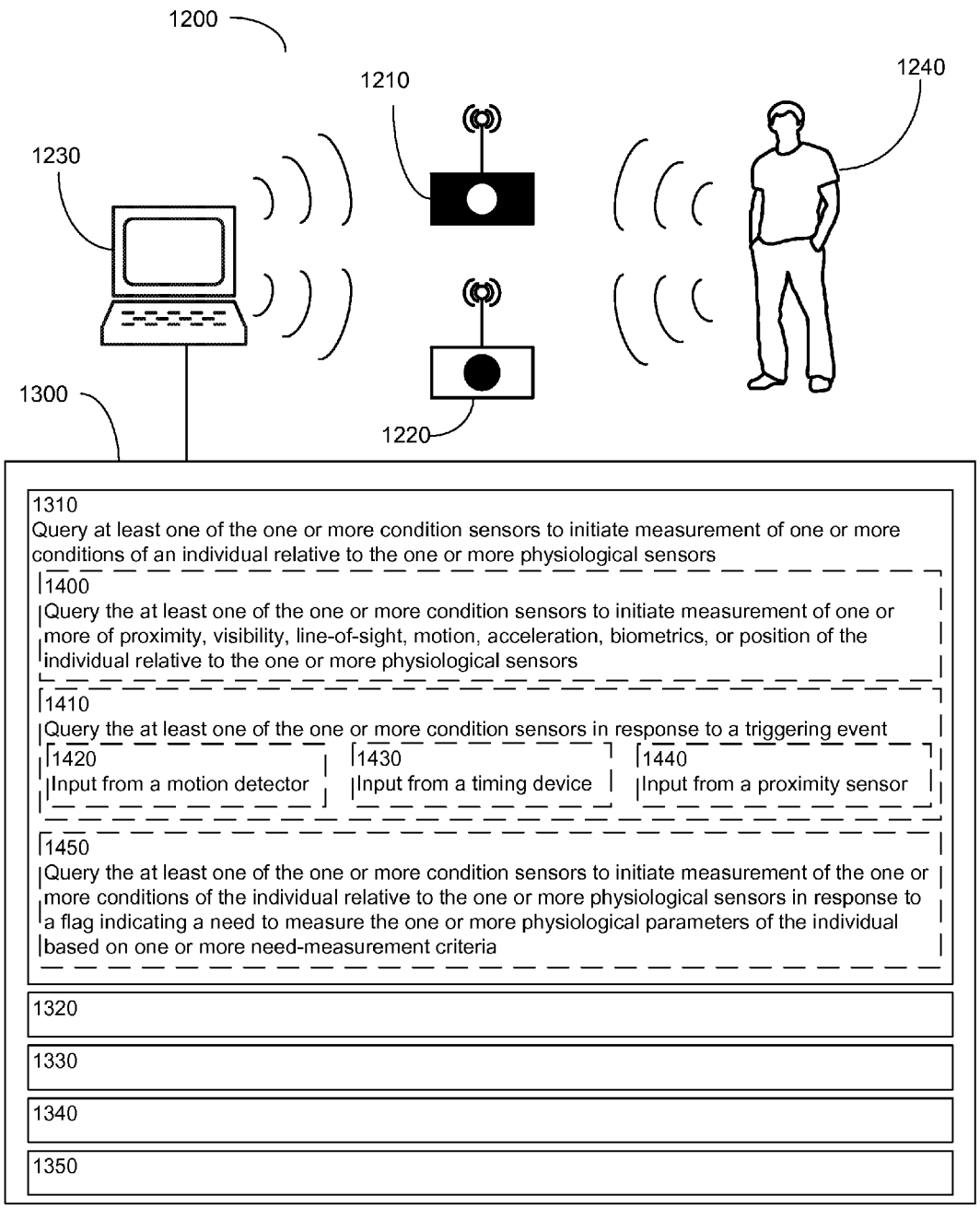

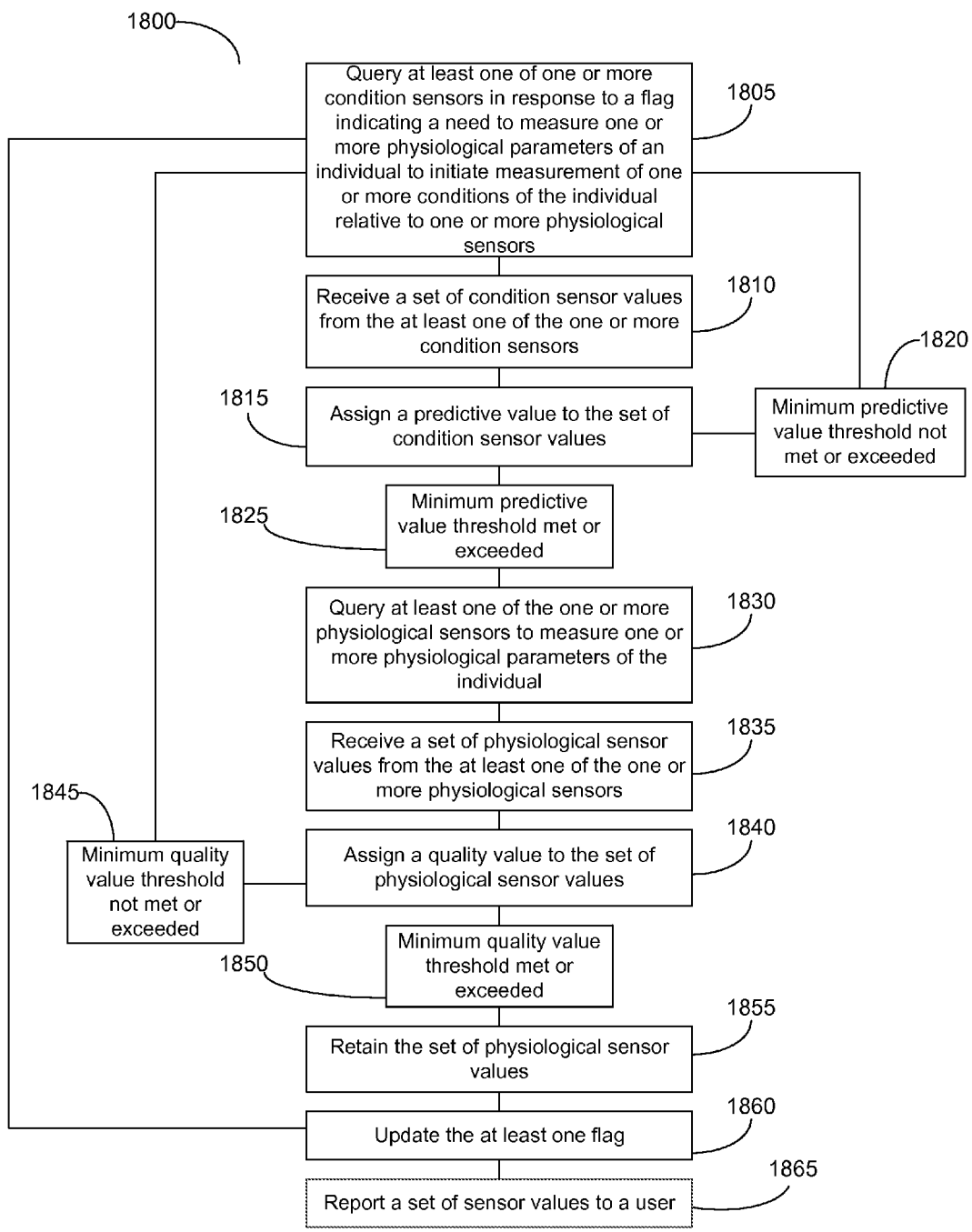

1900
Receiving a set of condition sensor values for an individual from at least one of one or more condition sensors in response to one or more queries, the set of condition sensor values representative of one or more conditions of the individual relative to one or more physiological sensors 1910
Assigning a predictive value to the set of condition sensor values 1920
Querying at least one of the one or more physiological sensors to measure one or more physiological parameters of the individual if the assigned predictive value of the set of condition sensor values meets or exceeds a minimum predictive value threshold 1930
Re-querying at least one of the one or more condition sensors if the assigned predictive value of the set of condition sensor values fails to meet or exceed the minimum predictive value threshold

FIG. 20

2000
Querying the at least one of the one or more condition sensors to measure one or more conditions of the individual relative to the one or more physiological sensors 2010
Querying the at least one of the one or more condition sensors in response to a triggering event 2020
Querying the at least one of the one or more condition sensors in response to at least one flag indicating a need to measure one or more physiological parameters of the individual 2030
The at least one flag indicating the need to measure the one or more physiological parameters of the individual is generated based on one or more need-measurement criteria 2040
Querying at least one of one or more motion sensors, one or more light sensors, one or more proximity sensors, or one or more biometric sensors 1900
Receiving a set of condition sensor values for an individual from at least one of one or more condition sensors in response to one or more queries, the set of condition sensor values representative of one or more conditions of the individual relative to one or more physiological sensors 2050
Receiving the set of condition sensor values for the individual from at least one of one or more motion sensors 2055
Receiving the set of condition sensor values for the individual from at least one of one or more light sensors 2060
Receiving the set of condition sensor values for the individual from at least one of one or more proximity sensors 2065
Receiving the set of condition sensor values for the individual from at least one of one or more contact sensors 2070
Receiving the set of condition sensor values for the individual from at least one of one or more biometric sensors 2075
Receiving the set of condition sensor values for the individual through one or more wireless transmissions

| 1900 |
| --- |
| Receiving a set of condition sensor values for an individual from at least one of one or more condition sensors in response to one or more queries, the set of condition sensor values representative of one or more conditions of the individual relative to one or more physiological sensors |

| 1910 |
| --- |
| Assigning a predictive value to the set of condition sensor values |
| 2100 Assigning a predictive value based on comparing the set of condition sensor values with a stored set of optimal condition values |
| 2110 Wherein the stored set of optimal condition values is stored in a computing device | 2120 Wherein the stored set of optimal condition values is part of a lookup table | 2130 Wherein the stored set of optimal condition values is specific for a condition sensor type |

| 1920 |
| --- |
| Querying at least one of the one or more physiological sensors to measure one or more physiological parameters of the individual if the assigned predictive value of the set of condition sensor values meets or exceeds a minimum predictive value threshold |
| 2150 Querying at least one of one or more non-contact physiological sensors | 2155 Querying at least one of one or more micro-impulse radar-based sensors | 2160 Querying at least one of one or more ultra-wideband radar-based sensors |
| 2165 Querying at least one of one or more of an audio sensor and/or an image capture device | 2170 Querying at least one of one or more thermal sensors | 2175 Querying the at least one of the one or more physiological sensors through one or more wireless transmissions |
| 2185 Querying the at least one of the one or more physiological sensors to measure one or more physiological parameters of the individual diagnostic for heart failure | 2180 Querying the at least one of the one or more physiological sensors through one or more wired transmissions |

| 1930 |
| --- |
| Re-querying at least one of the one or more condition sensors if the assigned predictive value of the set of condition sensor values fails to meet or exceed the minimum predictive value threshold |
| 2190 Re-querying the at least one of the one or more condition sensors until the assigned predictive value of the set of condition sensor values meets or exceeds the minimum predictive value threshold |

SYSTEMS AND METHODS FOR CONTROLLING ACQUISITION OF SENSOR INFORMATION

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None

RELATED APPLICATIONS

U.S. patent application Ser. No. 13/720,593, entitled SYSTEMS AND METHODS FOR CONTROLLING ACQUISITION OF SENSOR INFORMATION, naming Hon Wah Chin, Roderick A. Hyde, Robert C. Petroski, and Lowell L. Wood, Jr. as inventors, filed 19 Dec. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In an aspect, a system for controlling acquisition of sensor information includes, but is not limited to: one or more physiological sensors; and a computing device operably connected to the one or more physiological sensors, the computing device including a processor programmed to query at least one of the one or more physiological sensors to measure one or more physiological parameters of an individual in response to at least one flag indicating a need to measure the one or more physiological parameters; receive a set of sensor values from the at least one of the one or more physiological sensors, the set of sensor values representative of the measured one or more physiological parameters; assign a quality value to the set of sensor values received from the at least one of the one or more physiological sensors; retain the set of sensor values if the assigned quality value of the set of sensor values meets or exceeds a minimum quality value threshold; and update the at least one flag if the assigned quality value of the set of sensor values meets or exceeds the minimum quality value threshold. In addition to the foregoing, other system aspects are described in the claims, drawings, and text forming a part of the present disclosure.

In an aspect, a system for controlling acquisition of sensor information includes, but is not limited to: a computing device including a processor; and non-transitory signal-bearing medium bearing one or more instructions for controlling acquisition of information from one or more physiological sensors, the non-transitory signal-bearing medium including one or more instructions for generating at least one flag indicating a need to measure one or more physiological parameters of an individual based on one or more need-measurement criteria; one or more instructions for querying the one or more physiological sensors in response to the at least one flag; one or more instructions for receiving a set of sensor values from the one or more physiological sensor, the set of sensor values representative of one or more measured physiological parameters of an individual; one or more instructions for assigning a quality value to the set of sensor values received from the one or more physiological sensors; one or more instructions for retaining the set of sensor values if the assigned quality value of the set of sensor values meets or exceeds a minimum quality value threshold; one or more instructions for generating at least on updated flag if the assigned quality value of the set of sensor values meets or exceeds the minimum quality value threshold; and one or more instructions for re-querying the one or more physiological sensors to acquire an updated set of sensor values representative of the one or more measured physiological parameters of the individual if the assigned quality value of the set of sensor values fails to meet or exceed the minimum quality value threshold. In addition to the foregoing, other system aspects are described in the claims, drawings, and text forming a part of the present disclosure.

In an aspect, a method executed on a computing device for controlling acquisition of sensor information includes, but is not limited to: generating at least one flag indicating a need to measure one or more physiological parameters of an individual based on one or more need-measurement criteria; querying one or more physiological sensors in response to the at least one flag; receiving a set of sensor values from the one or more physiological sensors, the set of sensor values representative of the one or more measured physiological parameters of the individual; assigning a quality value to the set of sensor values received from the one or more physiological sensors; retaining the set of sensor values if the assigned quality value of the set of sensor values meets or exceeds a minimum quality value threshold; and updating the at least one flag if the assigned quality value of the set of sensor values meets or exceeds the minimum quality value threshold. In addition to the foregoing, other method aspects are described in the claims, drawings, and text forming a part of the present disclosure.

In an aspect, a system for controlling acquisition of sensor information includes, but is not limited to: one or more condition sensors; one or more physiological sensors; and computing device operably connected to the one or more condition sensors and the one or more physiological sensors, the computing device including a processor programmed to query at least one of the one or more condition sensors to initiate measurement of one or more conditions of an individual relative to the one or more physiological sensors; receive a set of condition sensor values from the at least one of the one or more condition sensors, the set of condition sensor values representative of the one or more conditions of the individual relative to the one or more physiological sensors; assign a predictive value to the set of condition sensor values; query at least one of the one or more physiological sensors to measure one or more parameters of the individual if the assigned predictive value of the set of condition sensor values meets or exceeds a minimum predictive value threshold; and re-query at least one of the one or more condition sensors if the assigned predictive value of the set of condition sensor values fails to meet or exceed the minimum predictive value threshold. In addition to the foregoing, other system aspects are described in the claims, drawings, and text forming a part of the present disclosure.

In an aspect, a method executed on a computing device for controlling acquisition of sensor information includes, but is not limited to: receiving a set of condition sensor values for an individual from at least one of one or more condition sensors in response to one or more queries, the set of condition sensor values representative of one or more conditions of the individual relative to one or more physiological sensors; assigning a predictive value to the set of condition sensor values; querying at least one of the one or more physiological sensors to measure one or more physiological parameters of the individual if the assigned predictive value of the set of condition sensor values meets or exceeds a minimum predictive value threshold; and re-querying at least one of the one or more condition sensors if the assigned predictive value of the set of condition sensor values fails to meet or exceed the minimum predictive value threshold. In addition to the foregoing, other method aspects are described in claims, drawings, and text forming a part of the present disclosure.

In an aspect, a system for controlling acquisition of sensor information includes, but is not limited to: a computing device including a processor and non-transitory signal-bearing medium bearing one or more instructions for controlling acquisition of information from one or more sensors, the non-transitory signal-bearing medium including one or more instructions for generating at least one flag indicating a need to measure one or more physiological parameters of an individual based on one or more need-measurement criteria; one or more instructions for querying at least one of one or more condition sensors to measure one or more conditions of the individual relative to one or more physiological sensors in response to the at least one flag; one or more instructions for receiving a set of condition sensor values from the at least one of the one or more condition sensors, the set of condition sensor values representative of the one or more conditions of the individual relative to the one or more physiological sensors; one or more instructions for assigning a predictive value to the set of condition sensor values; one or more instructions for re-querying at least one of the one or more condition sensors if the assigned predictive value of the set of condition sensor values fails to meet or exceed a minimum predictive value threshold; one or more instructions for querying at least one of the one or more physiological sensors to measure one or more physiological parameters of the individual if the assigned predictive value of the set of condition sensor values meets or exceeds the minimum predictive value threshold; one or more instructions for receiving a set of physiological sensor values from the at least one of the one or more physiological sensors, the set of physiological sensor values representative of the measured one or more physiological parameters; one or more instructions for assigning a quality value to the set of physiological sensor values received from the at least one of the one or more physiological sensors; one or more instructions for retaining the set of physiological sensor values if the assigned quality value of the set of physiological sensor values meets or exceed a minimum quality value threshold; and one or more instructions for updating the at least one flag indicating the need to measure the one or more physiological parameters of the individual if the assigned quality value of the set of physiological sensor values meets or exceeds the minimum quality value threshold. In addition to the foregoing, other system aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3 is a schematic of an embodiment of a system such as shown in FIG. 1.

FIG. 4 is a schematic of an embodiment of a system such as shown in FIG. 1.

FIG. 5 is a schematic of an embodiment of a system such as shown in FIG. 1.

FIG. 8 is a flowchart illustrating aspects of a method such as shown in FIG. 7.

FIG. 9 is a flowchart showing aspects of a method such as depicted in FIG. 7.

FIG. 10 is a flowchart depicting aspects of a method such as illustrated in FIG. 7.

FIG. 13 is a schematic of an embodiment of a system such as shown in FIG. 12.

FIG. 14 is a schematic of an embodiment of a system such as shown in FIG. 12.

FIG. 18 is a flow chart illustrating an embodiment of steps for controlling acquisition of information from physiological sensors.

FIG. 19 is a flow chart of a method of controlling acquisition of information from physiological sensors.

FIG. 20 is a flowchart illustrating aspects of a method such as shown in FIG. 19.

FIG. 21 is a flowchart showing aspects of a method such as depicted in FIG. 19.

DETAILED DESCRIPTION

Figure 1:
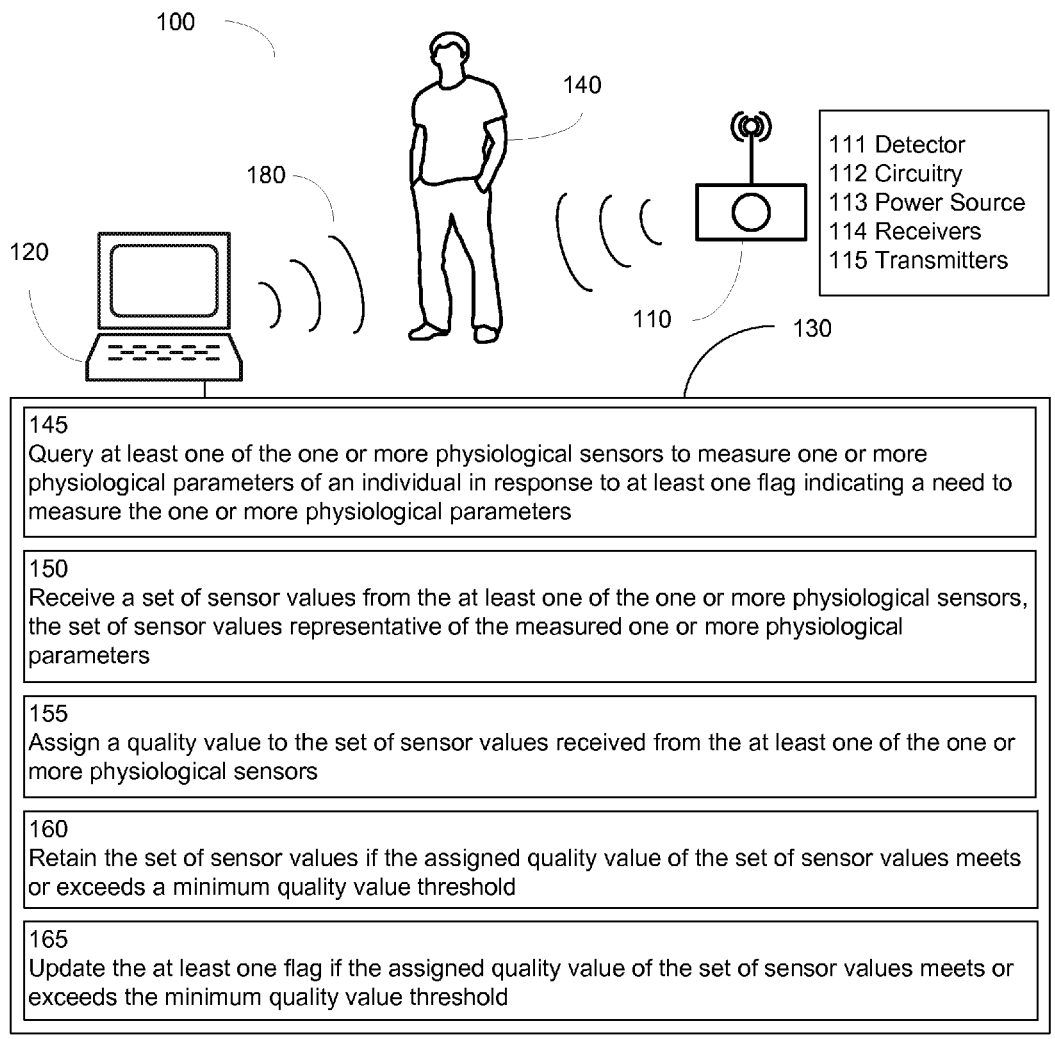
FIG. 1 is a schematic of a system for controlling acquisition of information from physiological sensors.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Systems and methods are described for controlling acquisition of information from one or more sensors. The systems and methods include controlling acquisition of information from one or more physiological sensors placed in a residential space. In a non-limiting example, the systems and methods described herein may be used to control acquisition of information from one or more physiological sensors configured to monitor one or more physiological parameters associated with a medical condition. The medical condition can include, but is not limited to, a pulmonary condition (e.g., asthma, chronic obstructive pulmonary disease), a metabolic condition (e.g., diabetes, obesity), a renal condition (e.g., kidney failure), a mental condition (e.g., schizophrenia, bipolar disorder), a neurodegenerative condition (e.g., Alzheimer's disease, Parkinson's, multiple sclerosis), a cardiovascular condition (e.g., heart failure, peripheral artery disease), or a cancer condition.

In a non-limiting example, the systems and methods described herein may be used to control acquisition of information from one or more physiological sensors configured to monitor an individual diagnosed with heart failure. Heart failure is a chronic, progressive condition in which the quantity of blood pumped by the heart each minute, i.e., cardiac output, is insufficient to meet an individual's normal requirements for oxygen and nutrients. The symptoms of heart failure include but are not limited to shortness of breath, fatigue, edema, rapid weight gain, a weak and often rapid heart rate, reduced blood pressure, exercise intolerance, certain abnormalities in heart sounds, an enlarged heart, swollen neck veins, fluid in the lungs, and enlarged liver. Heart failure can be caused by any of a number of conditions or diseases that affect the heart muscle and/or interfere with blood circulation, impairing the ability of the heart to contract and pump blood. The most common causes of heart failure include coronary artery disease, hypertension, and/or valvular heart diseases. Risk factors for developing heart failure include hypertension, atherosclerotic disease, diabetes, obesity, metabolic syndrome, previous myocardial infarction, smoking, excessive alcohol use, and use of certain drugs. Other non-limiting causes of heart failure include infections, pericardial diseases, connective tissue disease, infiltrative diseases, tachycardia, obstructive cardiomyopathy, neuromuscular disease, metabolic disorders, nutritional disorders, pheochromocytoma, radiation, endomyocardial fibrosis, eosinophilic endomyocardial disease, hyperthyroidism, anemia, Paget's disease, peripartum cardiomyopathy, and dilated idiopathic cardiomyopathy (see, e.g., Shamsham & Mitchell, *Am. Fam. Physician* 61:1319-1328, 2000, which is incorporated herein by reference). For an extensive review of heart failure from the American College of Cardiology Foundation and the American Heart Association Task Force, see, e.g., Hunt et al. *Circulation,* 119:e391-e479, 2009, which is incorporated herein by reference.

An individual who is able to manage the symptoms of heart failure through medication and life-style changes is said to have "compensated" heart failure. Sometimes the symptoms may suddenly get worse, indicating the onset of acute "decompensated" heart failure. Acute decompensated heart failure is defined as the sudden or gradual onset of the sign or symptoms of heart failure requiring unplanned office visits, emergency room visits, or hospitalization. It is important to monitor symptoms of initiation of heart failure in at-risk individuals and of worsening heart failure in those individuals who have been previously diagnosed with heart failure.

With reference to FIG. 1, shown is a schematic of a system for controlling acquisition of information from one or more sensors. System 100 includes one or more physiological sensors 110 and computing device 120. Computing device 120 includes a processor 130 programmed to query and receive from the one or more physiological sensors 110 information regarding one or more physiological parameters of an individual 140.

Computing device 120 of system 100 includes processor 130 programmed to query at least one of the one or more physiological sensors to measure one or more physiological parameters of an individual in response to at least one flag indicating a need to measure the one or more physiological parameters 145; receive a set of sensor values from the at least one of the one or more physiological sensors, the set of sensor values representative of the measured one or more physiological parameters 150; assign a quality value to the set of sensor values received from the at least one of the one or more physiological sensors 155; retain the set of sensor values if the assigned quality value of the set of sensors values meets or exceeds a minimum quality value threshold 160; update the at least one flag if the assigned quality value of the set of sensor values meets or exceeds the minimum quality value threshold 165.

System 100 includes one or more physiological sensors 110 configured to measure one or more physiological parameters of an individual. The one or more physiological parameters of an individual include, but are not limited to, height, weight, facial features, visible physical malformations, eye characteristic, appearance of skin, appearance of hair, appearance of nails, respiratory sounds, body temperature, blood gas level, heart rate, brain electrical activity, respiration rate, agitation, perspiration, tremor, facial expression, blood chemistries, blood cell counts, platelet counts, antibody titer, calcium level, blood antigen type, tissue antigen type, evidence of a pathogen exposure, lipid levels, perception of pain level, body movement, gait, stiffness, evidence of cognition state, dehydration, pain, malaise, injury, rigor, fever, light-headedness or dizziness, dry mouth, thirst, shortness of breath, nausea, weakness, sleepiness, hearing loss or problem, vision loss or problem, constipation, diarrhea, flatulence, urinary incontinence, loss of smell, loss of voice or problem, loss of ability to walk, to write, to use a limb. Generally, the one or more physiological parameters measured by the one or more physiological sensors 110 are diagnostic for an acute and/or chronic condition, e.g., heart failure, that is being monitored on a routine basis in a residential space.

In one embodiment, the one or more physiological sensors are configured to measure one or more physiological parameters of an individual diagnostic for heart failure. The one or more physiological parameters of the individual diagnostic for heart failure include, but are not limited to, one or more of tissue swelling, respiratory sounds, respiratory rate, heart rate, activity level, autonomic balance, weight, and/or blood oxygenation.

In one embodiment, one or more physiological sensors 110 are located in a residential space of an individual. In one embodiment, the residential space is a private residence, e.g., a single family home, townhouse, apartment, or condominium. In one embodiment, the residential space is a multi-individual residential space, e.g., a nursing or convalescent home, a group home, or other short or long-term care facility with multiple residents for whom individualized physiological monitoring of acute and/or chronic conditions may be appropriate.

In one embodiment, one or more physiological sensors 110 are located in a single room of a residential space, e.g., a living room or community room. In one embodiment, one or more physiological sensors are located throughout several rooms of a residential space, e.g., the living room, kitchen, bedroom, and/or bathroom, such that the one or more physiological sensors can monitor physiological parameters of an individual at various times during the day and during various activities, e.g., sitting, walking, eating, doing housework, toileting, sleeping, and the like.

In one embodiment, one or more physiological sensors 110 are located in an office space, e.g., an individual's office, a conference room, or a lunch room; a community space, e.g., a bus or train station or an airport, a theater, a classroom, or a gym; a clinical space, e.g., a hospital emergency room, a hospital room, a clinic waiting room. In general, the systems and methods described herein for controlling acquisition of information from sensors are applicable to physiological sensors and other sensor types arranged in a space so as to monitor a physiological parameter or condition of an individual.

In one embodiment, the one or more physiological sensors 110 are configured to physically contact an individual to measure a physiological parameter. In one embodiment, the one or more physiological sensors 110 are non-contact sensors, e.g., remote non-conductive sensors, configured to measure a physiological parameter of an individual without physically contacting the individual.

In one embodiment, the one or more physiological sensors 110 may be worn by the individual in or on clothing or jewelry or other accessory, such as in a garment, wrist band, or glasses, and may be in non-conductive contact with the body. In one embodiment, the one or more sensors 110 may be configured for use in an article of clothing or garment wearable by the individual and to sense a physiological parameter of the individual without physically contacting the individual (see, e.g., U.S. Patent Application Pub. No. 2006/0058694; WO 2003/048789; Harland, *Meas. Sci. Technol.* (2003) 14:923-928, each of which is incorporated herein by reference). In one embodiment, the one or more physiological sensors are incorporated into an accessory worn on the ankle and configured to measure ankle swelling, heart rate, and other physiological parameters (see, e.g., U.S. Patent Application Pub. No. 2012/0179020, which is incorporated herein by reference). In one embodiment, acquisition of information by the one or more physiological sensors worn on the individual is controlled by the computing device through one or more wireless transmissions.

In one embodiment, the one or more physiological sensors may be incorporated into a wearable or implantable monitor that is in wireless communication with the computing device. Non-limiting examples of wearable monitors include, but are not limited to, pace makers, Holter monitors, glucose monitoring devices, insulin delivery devices, infusion pumps, or smart clothing/fabrics. In one embodiment, system 100 may include one or more non-contact, unobtrusive physiological sensors located in the residential space, e.g., mounted on one or more walls of the residence, in addition to one or more wearable or implantable monitors. In one embodiment, the computing device is programmed to control information acquisition from the one or more non-contact, unobtrusive physiological sensors and the one or more wearable or implantable monitoring devices.

In one embodiment, the one or more physiological sensors 110, including one or more remote non-conductive sensors, are associated with items in the residential space. For example, the one or more physiological sensors may be located in one or more of furniture, walls, floors, doors, doorway, or window of the residential space. In one embodiment, one or more physiological sensors 110 are located in or proximal to one or more pieces of furniture in the residential space, non-limiting examples of which include chairs, bed, tables, computer, and/or a television set. In one embodiment, one or more physiological sensors 110 may be incorporated into a utensil or other household item used by the individual. For example, the one or more physiological sensors may be incorporated into an eating utensil, into a toilet, a bathroom scale, a handheld device (e.g., a cell phone or tablet device), or other household item that comes in direct or indirect contact with the individual on a regular/daily basis in a residential space. In one embodiment, the one or more physiological sensors 110 may be included in or associated with a piece of furniture, such as a desk or chair, or electronics such as a personal computer, or with some other remote item located at a specific distance, e.g., one meter, from the individual. In one embodiment, the one or more physiological sensors 110 are non-conductive physiological sensors embedded in objects, such as a bed or chair, and able to measure electric potentials by direct but non-conductive contact with the individual. For example, as described in U.S. Pat. No. 7,245,956, which is incorporated herein by reference.

In one embodiment, the one or more physiological sensors include at least one of a sensor type operable to measure tissue swelling. In general, tissue swelling and particularly rapid tissue swelling is an indicator of decompensated heart failure.

The degree and rapidity of retained fluids in the peripheral extremities, e.g., the lower extremities, correlate with the severity of heart failure. In some embodiments, the one or more physiological sensors are configured to measure changes in the "girth" or circumference of one or more portions of a lower extremity. In one embodiment, the one or more physiological sensor includes a sensor capable of measuring water content in tissue to detect increased fluid retention using, for example, multiple-frequency bioimpedance analysis (see, e.g., Raja et al., *J. Appl. Physics* (2006) 101: 1070-1075, which is incorporated herein by reference).

In one embodiment, the one or more physiological sensors are capable of measuring blood oxygenation. Sensors for assessing blood oxygenation include a pulse oximeter. A pulse oximeter detects and assesses changes in oxygen saturation. In one embodiment, a pulse oximeter includes a pair of small light-emitting diodes (LEDs) facing a photodiode through a translucent part of the patient's body, usually a fingertip or an earlobe. One LED is red, with wavelength of 660 nm and the other is infrared, 905, 910, or 940 nm. Absorption at these wavelengths differs significantly between oxyhemoglobin and its deoxygenated form and the oxy-deoxyhemoglobin ratio can be calculated from the ratio of the absorption of the red and infrared light. Monitored signal bounces in time with the heart beat because the arterial blood vessels expand and contract with each heartbeat. If oxygen transfer across the lungs or lung function is compromised and as tissue continue to metabolize oxygen, the percentage of oxyhemoglobin will decrease. In one embodiment, the one or more physiological sensors can include near-infrared spiroximetry for non-invasive measurements of venous saturation (see, e.g., Franceschini et al., *J. Appl. Physiol.* 92:372-384, 2002, which is incorporated herein by reference).

In one embodiment, the one or more physiological sensors include one or more image capture device, e.g., video cameras, or audio sensors, e.g., stand-alone microphones or microphones associated with an image capture device, for use in recording images and sounds, respectively of the individual or surroundings. In one embodiment, an audio sensor is used to measure coughing or wheezing, shortness of breath, confusion or impaired thinking as demonstrated in conversation with others, excessive snoring, or sleep apnea. In one embodiment, an image capture device is used to measure decrease in mobility, lack of appetite, e.g., eating less or not at all, or impaired thinking as observable odd behavior or confusion. In one embodiment, an image capture device is used to determine medication compliance, one of the common causes of decompensated heart failure. In one embodiment, an image capture device is used to measure jugular venous distension. In one embodiment, the information acquired by the image capture device and/or audio sensor are analyzed by the computing device using an algorithm. In one embodiment, the information acquired by the image capture device and/or audio sensor are analyzed by a physician or other caregiver.

In one embodiment, the one or more physiological sensors include an accelerometer to monitor movement, e.g., exercise or general mobility during waking hours. Similarly, the accelerometer or step counter in combination with a clock can be used to assess distance traveled in a specified period of time. For example, one measure of exercise tolerance is the distance traveled during a 6 minute walk. This can also be combined with measures of other physiological parameters such as heart rate, blood pressure, blood oxygenation, etc., to provide information regarding the cardiovascular fitness of an individual.

In one embodiment, the one or more physiological sensors 110 include at least one of ultrasound, bioimpedance, or infrared thermometry. In one embodiment, the one or more physiological sensors include audiovisual sensors (e.g., cameras that are audio and/or video recorders), eye trackers (e.g., images). See, for example, U.S Patent App. Pub Nos. 2010/0049045; 2006/0190419; 2008/0039698; or 2010/0174533, which are incorporated herein by reference.

In one embodiment, the one or more physiological sensors 110 may sense heart beat intervals and electrocardiographic information by examining physiological activity of the individual or its organs and may be operable to sense a physiological parameter of the individual in response to an electromagnetic signal sent at or illuminating the individual and reflected from the individual. In one embodiment, the illuminating may include exposing, subjecting, or directing energy at the subject. Systems using illuminating or reflected electromagnetic signals including radiofrequency (RF) or microwave signals, are described in U.S. Pat. No. 7,272,431; or U.S. Patent Application No. 2008/0045832; each of which is incorporated herein by reference. In one embodiment, the one or more physiological sensors 110 include one or more sensors incorporating ultra-wideband radar (see, e.g., Staderini *IEEE AESS Systems Magazine*, January 2002, pp. 13-18; which is incorporated herein by reference). An example of an ultra-wideband sensor for monitoring respiration, heart rate, and body movements is available from HOLUX Technology Inc., Hsinchu, Taiwan. In one embodiment, ultra-wideband sensors can be used to detect physiological parameters, e.g., heart rate and respiration, in the presence of multiple individuals (see, e.g., Rivera et al., "Multi-target estimation of heart and respiration rates using ultra wideband sensors," European Signal Processing Conference, Sep. 4-8, 2006, Florence, Italy, which is incorporated herein by reference). In one embodiment, the one or more physiological sensors 110 include one or more sensors incorporating micro impulse radar, a low-power form of ultra-wideband radar. For example, the heart rate of an individual can be monitored continuously using non-contact micro impulse radar (see, e.g., Michahelles et al., (2004) *Proceedings of the Eighth International Symposium on Wearable Computers* (ISWC'04) 1530-0811/04; U.S. Patent Application Pub. No. 2008/0007445; which are incorporated herein by reference). In one embodiment, the one or more physiological sensors 110 include one or more sensors incorporating microwave Doppler radar to remotely measure heart activity of an individual (see, e.g., Obeid et al., *International Conference on Communications Workshops* (2009), 10.1109/ICCW.2009.5208084, which is incorporated herein by reference).

In one embodiment, the one or more physiological sensors 110 include one or more capacitive-type sensor. In one embodiment, the one or more capacitive-type sensors are configured to sense bioelectric signals and/or bioelectric fields produced by an individual, for use in EEG, ECG, EOG and EMG. See, for example, U.S. Pat. No. 7,173,437, which is incorporated herein by reference.

In one embodiment, the one or more physiological sensors 110 include, for example, one or more acoustic sensors, optical sensors, electromagnetic energy sensors, image sensors, photodiode arrays, charge-coupled devices (CCDs), complementary metal-oxide-semiconductor (CMOS) sensors, transducers, optical recognition sensors, infrared sensors, radio frequency component sensors, thermo sensors, three-dimensional sensors (e.g., to assess the individual's facial expressions exhibiting pain or discomfort, flushing or redness, or an individual's gait or movements, etc.).

In one embodiment, one or more physiological sensors 110, which may be or include a sensor array, may be deployed, for example, throughout a room, perhaps as part of a smart room network, so as to monitor the individual at rest or in motion. For example, in one embodiment, the one or more physiological sensors 110 may include a sensor array configured to measure a physiological parameter of an individual without physically contacting the individual. In one embodiment, the sensor array may include at least two sensor heads, each of the at least two sensor heads measuring the same physiological parameter of the individual. In one embodiment, the sensor array may include at least two sensor heads, each of the at least two sensor heads measuring different physiological parameters of the individual. For example, one of the sensor heads may be configured to measure respiratory rate, another sensor head configured to measure respiratory sounds, and a further sensor head configured to measure blood pressure. In one embodiment, the one or more physiological sensors 110 include one or more physiological sensors responsive, without physically contacting the individual, to an impedance, capacitance, permittivity, reflectivity, absorption, or electrical activity of the individual.

In one embodiment, the one or more physiological sensors are part of a wireless sensor network (WSN). In one embodiment, the WSN consists of spatially distributed physiological sensors, the physiological sensors distributed in one or more rooms of a residential space. In one embodiment, the physiological sensors cooperatively pass data through the network to the computing device. In one embodiment, data is passed through the network to the computing device through one or more nodes. In one embodiment, the one or more physiological sensors in the WSN are in communication with one another and the computing device through a non-line-of-sight optical wireless communication (see, e.g., Kedar & Arnon, *Applied Optics* (2006) 45:8454-8461, which is incorporated herein by reference).

In one embodiment, the one or more physiological sensors 110 include a sensor device configured to sense a physiological parameter of the individual without physically touching the subject. In one embodiment, the sensor device includes a sensor device configured to sense a physiological parameter of an individual without resistive contact with the individual. In one embodiment, the sensor device includes a sensor device configured to sense a physiological parameter of an individual without electrically conductive contact with the individual. In one embodiment, the sensor device includes a sensor device configured to sense a physiological parameter of an individual across a non-electrically conductive gap with the individual.

In one embodiment, the one or more physiological sensors 110 include an electrodynamic sensor device configured to sense an electrical activity of the heart of an individual without physically contacting the individual. For example, the electrodynamic sensor may be configured to sense a heart rate, electrical activity of the heart, such as electrocardiography (ECG), or conductivity. An example of a high input impedance electrodynamic sensor device configured to sense an electrical activity of a heart of an individual without contacting the individual is described in U.S. Patent Application Pub. No. 2006/0058694; WO 2003/048789 which are incorporated herein by reference. In one embodiment, the physiological sensor includes an adaptive electric potential sensor device configured to sense a physiological parameter of an individual without physically contacting the individual. An example of an adaptive electric potential sensor device configured to sense a physiological parameter of an individual without physically contacting the individual is described in Prance et al., *J. Physics: Conference Series* (2007) 76:012025, which is incorporated herein by reference. In one embodiment, the physiological sensor includes an electric potential probe sensor device configured to sense a physiological parameter of an individual without physically contacting the individual. An example of an electric potential probe sensor device configured to sense a body's electrical activity or signals, such as for example arterial pulse or other body electrodynamics, of an individual without physically contacting the individual is described in Harland et al., *Meas. Sci. Tech.* (2002) 13:163-169, which is incorporated herein by reference.

In one embodiment, the one or more physiological sensors 110 include a sensor configured to sense at least one of an electrical, acoustic, thermal, absorption, reflection, gaseous emission, or transmissibility of an individual. In one embodiment, a thermal characteristic may include an infrared measured thermal physiological parameter of an individual, e.g., body temperature. In one embodiment, a thermal physiological parameter may include microwave length (3-30 cm) electromagnetic radiation naturally emitted by an individual. For example, a physiological sensor configured to sense a thermal physiological parameter of an individual includes a microwave radiometer operable to measure natural electromagnetic radiation from the individual's internal tissue in the microwave range. In one embodiment, the microwave radiometer may be combined with an infrared sensor (see, e.g., Avagyan et al., ICMART '99 International Medical Acupuncture Symposium 7, Riga, (May 21023, 1999; Pub. No. WO 2006/091123; which are incorporated herein by reference).

The one or more physiological sensors 110 may further include one or more detectors 111. In one embodiment, numerous different types of detectors 111 are operably coupled to one or more physiological sensors 110. Non-limiting examples of detectors include electrodes, surface plasmon resonance detectors, microelectromechanical systems detectors, microcantilever detectors, nitric oxide detectors, osmotic detectors, relativity-based detectors, chemical detectors, pressure detectors, electrochemical detectors, piezoelectric detectors, pH detectors, hydrogel detectors, enzymatic detectors, ball integrated circuit detectors, affinity viscosimetric detectors, blood pressure detectors, glucose detectors, and the like (see, e.g., U.S. Pat. Nos. 6,280,604; 7,168,294; 6,823,717; 7,205,701; 6,268,161; 6,210,326; 6,514,689; 6,234,973; Tu et al., *Electroanalysis*, 11:70-74 (1999), each of which is incorporated herein by reference).

The one or more physiological sensors 110 are operably coupled to computing device 120. Computing device 120 controls acquisition of information from one or more physiological sensors 110 based on a series of on/off flags (or activated/inactivated flags) stipulated by need-measurement criteria as part of a monitoring schedule. For example, in one embodiment, computing device 120 is programmed or operable to control one or more times when one or more physiological sensors 110 detect one or more signals related to one or more physiological parameters of individual 140. In one embodiment, the computing device 120 is programmed or operable to control one or more time periods when one or more physiological sensors 110 detect one or more signals from the individual that are related to one or more physiological parameters of the individual. In some embodiments, the one or more physiological sensors are operably connected to more than one computing device. For example, in a residence where more than one individual is being monitored, each individual's monitoring instructions or schedule, e.g., need-measurement criteria, may be stored in separate computing devices, each computing device separately programmed or operable to query the one or more physiological sensors in the residence to separately measure the physiological parameters of each individual according to individualized need-measurement criteria.

In one embodiment, one or more physiological sensors 110 include circuitry 112 that is operably coupled to one or more detectors 111. In one embodiment, one or more physiological sensors 110 include circuitry 112 that is configured to be operably coupled to computing device 120. In one embodiment, one or more physiological sensors 110 include circuitry 112 that is configured to be operably coupled to one or more sensor power sources 113. In one embodiment, one or more physiological sensors 110 include circuitry 112 that is configured to be operably coupled to one or more sensor receivers 114. In one embodiment, one or more physiological sensors 110 include circuitry 112 that is configured to be operably coupled to one or more sensor transmitters 115.

In one embodiment, a physiological sensor 110 includes one or more sensor power sources 113 (including but not limited to batteries). In one embodiment, a physiological sensor 110 is operably coupled to one or more sensor batteries. In one embodiment, the one or more sensor batteries include nickel-cadmium, nickel-zinc, nickel-metal hydride, and/or lithium ion batteries. In one embodiment, the power source energy is renewable, e.g., from solar sources, temperature differences, or vibration. In one embodiment, a sensor battery includes a thin-film fuel cell such as a solid oxide type (SOFC), a solid polymer type (SPFC), a proton exchange membrane type (PEMFC), and/or substantially any combination thereof. Methods to fabricate such thin-film fuel cells are known and have been described (see, e.g., U.S. Pat. No. 7,189,471, incorporated herein by reference). In one embodiment, one or more sensor batteries include one or more storage films that are configured for energy storage and energy conversion. Methods to fabricate such storage films are known and have been described (see, e.g., U.S. Pat. No. 7,238,628, incorporated herein by reference). In one embodiment, power source 113 is a bio-based battery (see, e.g., U.S. Pat. No. 6,994,934, incorporated herein by reference). In one embodiment, power source 113 include thin-film batteries. Methods to fabricate thin-film batteries, including thin film microbatteries, are known and have been described (see, e.g., U.S. Pat. No. 7,194,801, which is incorporated herein by reference). In one embodiment, one or more sensor electromagnetic receivers (not shown) are used to electromagnetically couple power to energize one or more sensors 110 from an external power source. Methods to construct electromagnetic receivers have been described (see, e.g., U.S. Pat. No. 5,571,152), which is incorporated herein by reference). In one embodiment, the receiver and/or transmitter are not part of the sensor.

In one embodiment, the system 100 includes one or more sensor transmitters 115. Numerous types of transmitters 115 can be used in association with system 100. Examples of such transmitters include, but are not limited to, transmitters that transmit one or more acoustic signals, optical signals, radio signals, wireless signals, hardwired signals, infrared signals, ultrasonic signals, and the like. In one embodiment, one or more sensor transmitters 115 may transmit one or more signals that are encrypted. Numerous types of transmitters are known and have been described (see, e.g., U.S. Pat. Nos. 7,236,595; 7,260,155; 7,227,956, which are incorporated herein by reference).

In one embodiment, the system 100 includes one or more sensor receivers 114. Numerous types of sensor receivers 114 may be used in association with system 100. Examples of such sensor receivers include, but are not limited to, receivers that receive one or more acoustic signals, optical signals, radio signals, wireless signals, hardwired signals, infrared signals, ultrasonic signals, and the like. Such receivers are known and have been described (see, e.g., U.S. Pat. Nos. 7,218,900; 7,254,160; 7,245,894; which are incorporated herein by reference).

In one embodiment, a signal can be an external signal 180. Examples of such signals include, but are not limited to, analog signals, digital signals, acoustic signals, optical signals, radio signals, wireless signals, hardwired signals, infrared signals, ultrasonic signals, and the like. In one embodiment, one or more signals may not be encrypted. In one embodiment, one or more signals may be encrypted (see, e.g., Pathan et al., *International Conference Advanced Communication Technology*, Feb. 2-22, 2006, pp. 1043-1048). In one embodiment, one or more signals may be sent through use of a secure mode of transmission. In one embodiment, one or more signals may be coded for receipt by a specific user. In one embodiment, such code may include anonymous code that is specific for a user. Accordingly, information included within one or more signals may be protected against being accessed by others who are not the intended recipient.

In one embodiment, the information gathered by the one or more sensors 110 is communicated to computing device 120. In one embodiment, the information received by computing device 120 from the one or more physiological sensors 110 has already been processed by the sensor to indicate a value, e.g., a heart rate or a temperature. In some embodiments, the information received by computing device 120 from one or more physiological sensors 110 is received as raw data, e.g., an electrical, electromagnetic, or optical signal, which the processor is able to transform into meaningful information or value point, e.g., a heart rate or a temperature. In one embodiment, information may be communicated to computing device 120 of system 100 electronically. In one embodiment, information may be communicated to computing device 120 wirelessly using, for example, Bluetooth technology.

Computing device 120 can take various forms or be part of an object, such as a limited resource computing device, a wireless communication device, a mobile wireless communication device, an electronic pen, a handheld electronic writing device, a tablet, a digital camera, a scanner, an ultrasound device, an x-ray machine, a non-invasive imaging device, a cell phone, a PDA, an electronic tablet device, a medical apparatus (implantable or otherwise), or a printer.

Figure 2:
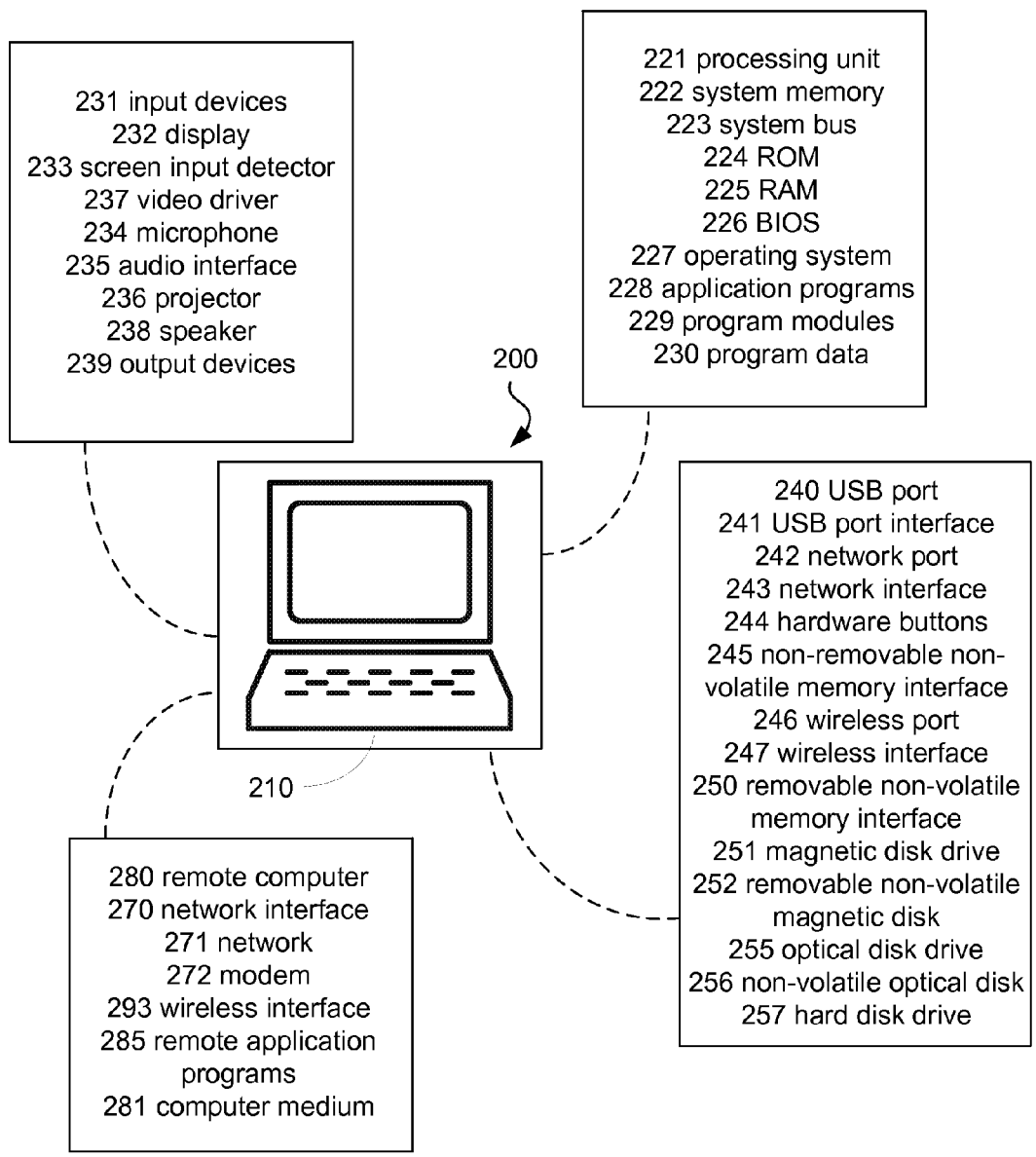
FIG. 2 is a schematic of a computing device.

FIG. 2 illustrates further embodiments of a computing device. Computing device 200 includes a processing unit 221, a system memory 222, and a system bus 223 that couples various system components including the system memory 222 to the processing unit 221. Processing unit 221 can include a microprocessor, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In one embodiment, the computing device includes one or more ASICs having a plurality of predefined logic components. In one embodiment, the computing device includes one or more FPGAs having a plurality of programmable logic commands.

The system bus 223 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device can include one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In some embodiments, one or more user input/output components are operably coupled to the computing device to control (electrical, electromechanical, software-implemented, firmware-implemented, or other control, or combinations thereof) entry of an individual's need-measurement criteria and monitoring schedule.

The system memory includes read-only memory (ROM) 224 and random access memory (RAM) 225. A basic input/output system (BIOS) 226, containing the basic routines that help to transfer information between sub-components within computing device 200, such as during start-up, is stored in the ROM 224. A number of program modules may be stored in the ROM 224 or RAM 225, including an operating system 227, one or more application programs 228, other program modules 229 and program data 230.

A user may enter commands and information into the computing device 200 through user input devices, such as a number of switches and buttons, illustrated as hardware buttons 244, connected to the system via a suitable interface 245. Input devices 231 may further include a touch-sensitive display with suitable input detection circuitry, illustrated as a display 232 and screen input detector 233. The output circuitry of the touch-sensitive display 232 is connected to the system bus 223 via a video driver 237. Other input devices may include a microphone 234 connected through a suitable audio interface 235, and a physical hardware keyboard 210. Output devices may include at least one the display 232, or a projector display 236.

In addition to the display 232, the computing device 200 may include other peripheral output devices, such as at least one speaker 238. Other external input or output devices 239, such as a joystick, game pad, satellite dish, scanner or the like may be connected to the processing unit 221 through a USB port 240 and USB port interface 241, to the system bus 223. Alternatively, the other external input devices 231 and output devices 239 may be connected by other interfaces, such as a parallel port, game port or other port. The computing device 200 may further include or be capable of connecting to a flash card memory (not shown) through an appropriate connection port (not shown). The computing device 200 may further include or be capable of connecting with a network through a network port 242 and network interface 243, and through wireless port 246 and corresponding wireless interface 247 may be provided to facilitate communication with other peripheral devices, including one or more condition sensors, one or more physiological sensors, other computers, printers, and so on (not shown). It will be appreciated that the various components and connections shown are examples and other components and means of establishing communication links may be used.

A user may enter commands and information into the computing device 200 through input device 231 such as a microphone, keyboard, or pointing device, commonly referred to as a mouse, trackball, or touch pad. Other input devices may include at least one of a touch sensitive display, joystick, game pad, satellite dish, and scanner. These and other input devices are often connected to the processing unit through a user input interface that is coupled to the system bus, but may be connected by other interface and bus structures, such as a parallel port, game port, or a universal serial bus (USB).

The computing device 200 may be designed to include a user interface. The user interface may include a character, a key-based, or another user data input via a keyboard or touch sensitive display. The user interface may include using a stylus (not shown). Moreover, the user interface is not limited to an actual touch-sensitive panel arranged for directly receiving input, but may alternatively or in addition respond to another input device such as the microphone 234. For example, spoken words may be received at the microphone 234 and recognized.

In certain instances, the computing system typically includes a variety of computer-readable media products. Computer-readable media may include any media that can be accessed by the computing device 200 and include both volatile and nonvolatile media, removable and non-removable media. By way of example, and not of limitation, computer-readable media may include non-transitory signal-bearing media. By way of example, and not of limitation, computer-readable media may include computer storage media. By way of further example, and not of limitation, computer-readable media may include a communication media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media may include wired media, such as a wired network and a direct-wired connection, and wireless media such as acoustic, RF, optical, and infrared media.

The computing device 200 may also include other removable/non-removable, volatile/nonvolatile computer storage media products. For example, such media includes a non-removable non-volatile memory interface (hard disk interface) 245 reads from and writes for example to non-removable, non-volatile magnetic media, or a removable non-volatile memory interface 250 that, for example, is coupled to a magnetic disk drive 251 that reads from and writes to a removable, non-volatile magnetic disk 252, or is coupled to an optical disk drive 255 that reads from and writes to a removable, non-volatile optical disk 256, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 257 is typically connected to the system bus 223 through a non-removable memory interface, such as the interface 245, and magnetic disk drive 251 and optical disk drive 255 are typically connected to the system bus 223 by a removable non-volatile memory interface, such as interface 250.

The drives and their associated computer storage media discussed above provide storage of computer-readable instructions, data structures, program modules, and other data for the computing device 200.

The computing device may operate in a networked environment using logical connections to one or more remote computers, such as a remote computer 280. The remote computer 280 may be a personal computer, a server, a router, a network PC, a peer device, or other common network node, and typically includes many or all of the elements described above relative to the computing device 200. The network logical connections include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing device is connected to the network 271 through a network interface, such as the network interface 270, the modem 272, or the wireless interface 293. The network may include a LAN network environment, or a WAN network environment, such as the Internet. In a networked environment, program modules depicted relative to the computing device 200, or portions thereof, may be stored in a remote memory storage device. By way of example, and not limitation, remote application programs 285 as residing on computer medium 281. It will be appreciated that the network connections shown are examples and other means of establishing communication link between the computers may be used.

In certain instances, one or more elements of the computing device 200 may be deemed not necessary and omitted. In other instances, one or more other components may be deemed necessary and added to the computing device 200.

In one embodiment, image-based applications such as viewers and/or toolkits (e.g., Insight Segmentation and Registration Toolkit (ITK)), are incorporated for further intake of information. In one embodiment, CAD implementations or image segmentation may allow processing of received digital images.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 200. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

In one embodiment, the computing device includes a computer-readable media drive or memory slot that is configured to accept non-transitory signal-bearing medium (e.g., computer-readable memory media, computer-readable recording media, or the like). In one embodiment, a program for causing a system to execute any of the disclosed methods can be stored on, for example, a computer-readable recording medium (CRMM), a non-transitory signal-bearing medium, or the like. Non-limiting examples of signal-bearing media include a recordable type medium such as magnetic tape, floppy disk, a hard disk drive, Compact Disc (CD), a Digital Video Disk (DVD), Blu-Ray Disc, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINI-DISC, non-volatile memory card, EEPROM, optical disk, optical storage, RAM, ROM, system memory, web server, cloud, or the like.

In some embodiments, the computing device includes one or more modules optionally operable for communication with one or more input/output components that are configured to relay user output/input. In one embodiment, a module includes one or more instances of electrical, electromechanical, software-implemented, firmware-implemented, or other control devices. Such devices include one or more instances of memory, computing devices, antennas, power or other supplies, logic modules or other signaling modules, gauges or other such active or passive detection components, piezoelectric transducers, shape memory elements, micro-electro-mechanical systems (MEMS) elements, or other actuators.

FIG. 3 illustrates further aspects of system 100 depicted in FIG. 1. Computing device 120 of system 100 includes processor 130 programmed to query at least one of the one or more physiological sensor to measure one or more physiological parameters of an individual in response to at least one flag indicating a need to measure the one or more physiological parameters, as shown in block 145. In one embodiment, computing device 120 including processor 130 is programmed to generate the at least one flag indicating the need to measure the one or more physiological parameters based on one or more need-measurement criteria, as shown in block 300. In one embodiment, the one or more need-measurement criteria include a time of day. For example, measurement of a specific physiological parameter, e.g., resting heart rate, might be best measured at a specific time in the morning after waking. For example, measuring physiological parameters associated with sleep apnea might be best measured during specific hours of the night, e.g., when the individual is anticipated to be sleeping. For example, measuring the individual's weight might be best done at a specific time every 24 hours, e.g., every morning before showering. In one embodiment, the one or more need-measurement criteria include an interval of time since a previous measurement. For example, the one or more need-measurement criteria may include intervals of time over which a specific physiological parameter is measured. For example, the one or more need-measurement criteria may include measuring an individual's weight every 24 hours. For example, the one or more need-measurement criteria may include measuring an individual's heart rate every hour. In one embodiment, the one or more need-measurement criteria include the number of sensor values needed over time for a reliable diagnosis. For example, generating a reliable heart rate may require measuring an individual's heart rate for a set period of time, e.g., a minute or longer, to get an accurate or reliable heart rate. For example, multiple sensor values over a given period of time may be needed to overcome inherent noise in the sensor/computing device transmitting and receiving functions. For example, a sensor which transmits a signal marginally above noise may need to transmit multiple signals to allow for improved signal-to-noise. In one embodiment, the one or more need-measurement criteria include a number of sensor values with assigned quality values that meet the minimum quality value threshold. For example, the computing device may continue to collect data from a given sensor type until the sensor values achieve assigned quality values that meet and/or exceed the minimum quality value threshold, e.g., have sufficient signal-to-noise to be considered quality data and useful for a reliable diagnosis. In one embodiment, the one or more need-measurement criteria include a health status of the individual. For example, if the health status of the individual is relatively good, e.g., stable, then the number of queries may be reduced. If the health status of the individual is deteriorating, the number of queries may be increased to more tightly monitor the condition. In one embodiment, information regarding an individual's health status and any associated changes to the need-measurement criteria are received by the computing device from the individual's physician or other caregiver. In one embodiment, the computing device may be programmed to automatically update the need-measurement criteria, e.g., increase the number of queries to one or more of the physiological sensors if the received sensor values indicate that a health status is deteriorating. For example, if the sensor values received from an audio/video sensor indicates that the individual's breathing has become more labored, the computing device automatically increases the frequency of querying the audio/video sensor to monitor the potentially deteriorating situation. Conversely, if it appears that the sensor values are indicating an improvement trend, e.g., a return to more normal breathing, the computing device automatically decreases the number of queries to the one or more physiological sensors.

In one embodiment, the need-measurement criteria are provided to the computing device. In one embodiment, the need-measurement criteria are part of a monitoring schedule prescribed by a physician or other caregiver to monitor physiological parameters of the individual associated with a medical condition. In one embodiment, an individual receives a "prescription" from a physician or other caregiver in the form of a monitoring schedule with need-measurement criteria that are loaded onto a computing device through a portable data storage device, the Internet, or through an input device, e.g., a keyboard or touchpad. In one embodiment, the "prescription" is placed onto a portable computing device, e.g., a laptop computer, in a physician's office and subsequently taken home for use in controlling one or more physiological sensors in the individual's residence.

In one embodiment, the computing device which includes a processor and is programmed to control acquisition of information from one or more sensors is located in the residence of the individual. In one embodiment, the computing device including a processor and programmed to control acquisition of information from one or more sensors is located in a location remote from the individual's residence, e.g., a physician's office, clinic, hospital, or other offsite location. The computing device in a remote location communicates with the one or more physiological sensors through a wired or wireless transmission means.

In some embodiments, the need-measurement criteria received by the computing device are updatable. In one embodiment, updates to the need-measurement criteria are carried out by downloading the updated need-measurement criteria from a data storage device, e.g., a memory stick or USB drive. In one embodiment, the updates to the need-measurement criteria can be received by the computing device through the Internet. In one embodiment, the need-measurement criteria can be manually entered into the computing device using a user input or interface device, e.g., a keyboard or touchpad, associated with the computing device. The updates to the need-measurement criteria can be made by a physician or other caregiver either on site or at a remote location. In one embodiment, the updates to the need-measurement criteria are made by the individual. In some embodiments, the need-measurement criteria are updated to accommodate changes in the health of the individual. For example, an improvement in an individual's health status may decrease the number of times a specific sensor type is queried over the course of a day. For example, deterioration in an individual's health status may increase the number of times and/or the number of types of sensors that are queried over the course of a day. In some embodiments, the need-measurement criteria are updated to accommodate changes in the number and/or identity of individuals residing in a particular residence.

Returning to FIG. 3, computing device 120 including processor 130 is optionally programmed to query the at least one of the one or more physiological sensors in a time dependent manner, as illustrated in block 310. In one embodiment, the computing device is programmed to query the one or more physiological sensors in a time dependent manner 310 in response to a flag indicating a need to measure one or more physiological parameters generated based on a need-measurement criteria.

In one embodiment, computing device 120 including processor 130 is optionally programmed to query the at least one of the one or more physiological sensors in a sensor dependent manner, as illustrated in block 320. In one embodiment, the computing device is programmed to query a physiological sensor in a sensor dependent manner in response to a flag indicating a need to measure one or more physiological parameters generated based on a need-measurement criteria. For example, a first sensor type may provide more reliable information then a second sensor type and consequently fewer data points are required from the first sensor type relative to the second sensor type to acquire data sufficient for a reliable diagnosis. For example, a first sensor type may be queried 3 times over a given period of time while a second sensor type is queried 10 times over the same period of time.

In one embodiment, computing device 120 including processor 130 is optionally programmed to query the at least one of the one or more physiological sensors based on a number of previous queries to the at least one of the one or more physiological sensors, as illustrated in block 330. For example, if a specific sensor type has been queried 7 times and the need-measurement criteria include querying this specific sensor type 10 times, the computing device is programmed to query the sensor until it has been queried 10 times.

In one embodiment, computing device 120 including processor 130 is optionally programmed to query the at least one of the one or more physiological sensors based on a health status of the individual, as illustrated in block 340. In one embodiment, the computing device is programmed to query the one or more physiological sensors based on the health status of the individual in response to at least one flag indicating a need to measure one or more physiological parameters generated based on a need-measurement criteria. In one embodiment, the computing device may be programmed to query at least one of the one or more physiological sensors based on the individual's medical condition. For example, in a residential space with a variety of sensor types, monitoring an individual with heart failure can involve querying a micro impulse radar-based sensor and an audio/video sensor to monitor heart rate/respiratory rate and breathing while monitoring an individual with schizophrenia, for example, may involve audio/video monitoring. In one embodiment, the computing device may be programmed to query at least one of the one or more physiological sensors based on the severity of the individual's medical condition. For example, the more severe the condition, the more frequently the one or more physiological sensors may be queried. For example, the more severe the condition, the more different types of physiological sensors may be queried to monitor different physiological parameters associated with the condition.

In one embodiment, computing device 120 including processor 130 is optionally programmed to query the at least one of the one or more physiological sensors based on the identity of the individual, as illustrated in block 350. For example, in a multi-individual residence, the one or more physiological sensors can be queried at different times using individualized need-measurement criteria resulting in a monitoring schedule of queries specific for each individual. For example, each of the individuals requiring monitoring may have a separate set of need-measurement criteria that informs the computing device as to when to generate a flag for querying the one or more physiological sensors. The timing and types of sensor queries may vary from one individual to the next. In one embodiment, biometric information is obtained to determine which individual has entered a specific room. In one embodiment, sensors may be queried on a set schedule and biometric information attained at the same time to determine which individual has been monitored.

In one embodiment, computing device 120 including processor 130 is optionally programmed to query the one or more physiological sensors based on the assigned quality value of a previously received set of sensor values, as illustrated in block 360. For example, if the assigned quality value of a previously received set of sensor values fails to meet or exceed the minimum quality value threshold, the flag indicating a need for a measurement remains active and the one or more physiological sensors are queried. For example, if the assigned quality value of a previously received set of sensor values meets or exceeds the minimum quality value threshold, but higher quality and/or quantity of sensor information is needed, e.g., at a higher minimum quality value threshold, the one or more physiological sensors are queried.

FIG. 4 illustrates further aspects of system 100 depicted in FIG. 1. Computing device 120 of system 100 includes processor 130 programmed to receive a set of sensor values from the at least one of the one or more physiological sensors, the set of sensor values representative of the measured one or more physiological parameters, as shown in block 150. In one embodiment, computing device 120 with processor 130 is optionally programmed to receive the set of sensor values through a wireless transmission 400, e.g., a radiofrequency transmission. Wireless transmission can further include, but is not limited to, one or more radio transmission, microwave transmission (e.g., wireless LAN, Wi-Fi, wireless PAN, Bluetooth, wireless WAN, 2G/3G, broadband, MAN, WiMAX, radar and satellite communications), infrared transmission (e.g., point-to-point or broadcast communication), or other optical transmission means (e.g., laser diodes, laser beams). In one embodiment, computing device 120 with processor 130 is optionally programmed to receive the set of sensor values through a wired transmission 410, e.g., an electrical connection. Wired transmission can further include, but is not limited to, transmission through one or more telephone line, cable line, internet line, fiber optic line, coaxial cable, UPT/STP or any other like wired communication line.

Returning to FIG. 4, computing device 120 of system 100 including processor 130 is programmed to assign a quality value to the set of sensor values received from the at least one of the one or more physiological sensors, as shown in block 155. In one embodiment, the assigned quality value is an indicator of whether or not the sensor values are of high enough quality to contribute to a reliable medical diagnosis. In one embodiment, the assigned quality value is an arbitrary number between 0 and 100. The quality value is assigned based on the quality of the information received from the at least one of the one or more physiological sensors. In one embodiment, the assessment of the quality of the information received is dependent upon the type of sensor being used and the allowable variability. For example, with ultra-wideband radar, the quality of a measured impulse response function is mainly determined by the ability to separate closely located peaks and to avoid the masking of smaller peaks due to noise or saturation effects caused by larger signal (see, e.g., Thiel et al., *Sensors* (2010) 10:10778-10802, which is incorporated herein by reference).

In one embodiment, computing device 120 including processor 130 is optionally programmed to assign the quality value to the set of physiological sensor values by comparing the set of physiological sensor values with a set of standard values, as shown in block 420. The set of standard values is a set of physiological sensor values adequate enough to provide a reliable medical diagnosis.

In one embodiment, the set of standard values is a set of standard values with defined signal-to-noise ratio, as shown in block 430. Noise can arise from the process being measured itself or introduced by the sensor. If the noise is mostly random with a zero mean, multiple measurements can achieve a better estimate of the actual value being measured. Another form of noise is from other events or influences that couple into the process being measured. For example, a microphone on a telephone will pick up background sounds. For example, when sensing audio associated with an individual's breathing, multiple microphones can be used at varying distances from the individual to distinguish audio signals from the individual from background audio signals in the individual's setting. For example, in some embodiments, a signal-to-noise ratio above 1 may provide sufficient information. In some embodiments, a signal-to-noise ratio significantly above 1 may be needed to provide sufficient information. Signal-to-noise ratio compares the level of desired signal to the level of background noise. In one embodiment, the signal-to-noise ratio is the ratio of signal power to noise power. A signal-to-noise ratio higher than 1:1 indicates more signal than noise. In one embodiment, the sensor itself may be capable of subtracting noise from the sensed information and subsequently sends sensor values to the computing device from which noise associated with the sensor has already been subtracted. In one embodiment, it may still be necessary to determine a signal-to-noise ratio or to subtract noise associated with transmitting and receiving the sensor values from the one or more sensors.

In one embodiment, the set of standard values is a set of standard values with acceptable levels of error, e.g., noise. In one embodiment, the error can include a transducer error. A transducer responds to some physical condition, e.g., temperature, pressure, or movement, and generates a signal. In some embodiments, the reporting signal is an electrical signal, initially an analog signal which is converted to a digital representation. Rules associated with the analog-digital conversion may be calibrated. For precision instruments, e.g., each transducer is tested and calibrated against a physical standard and may be repeated periodically to maintain high confidence. While typical transducers are sufficiently linear in some region of interest, high precision measurements would be dependent on multiple calibration points within the range of measurements to reduce the errors from non-linearities in the transducer. In one embodiment, calibration may also depend on other ambient conditions, e.g., temperature. Depending on the sensitivity of the measurement, the measurement process might include measuring the temperature and applying a temperature based calibration or correction.

In some embodiments, the errors can include errors in processing the signal, e.g., due to failures in a transducer or processing equipment. For example, a shorted thermocouple or stress wire-connector to a strain gauge may give bad values. For example, an analog to digital converter might also include errors, e.g., a software error. For example, one part of a processor/controller may introduce crosstalk into another part, especially into low amplitude signals received from a transducer. The sensor/transducer might not be in the correct position to measure the desired process. In one embodiment, redundancy techniques used in high reliability control systems can be used to address these eventualities. In one embodiment, multiple sensors in different locations can be used for cross checking information. In one embodiment, a consistency check built into the controller can be used to detect failures in control processors.

In one embodiment, the set of standard values is a set of standard values representing a relevant range of values for a specific physiological parameter, as illustrated in block 440. In one embodiment, the relevant range of values for a specific physiological parameter includes values that are physiologically possible. For example, the relevant range of values for a specific physiological parameter, e.g., heart rate, ranges from 0 beats/min to 300 beats/min. A sensor value of 400 beats/min, for example, would be outside the range of expected heart rates, even under pathological conditions, and as such the set of sensor values would fall outside standard values, i.e., not meet the minimum quality value threshold, and trigger a re-query of the one or more physiological sensors for a higher quality set of sensor values. For example, a sensor value from a scale indicating a remarkable change in weight, e.g., 10 pounds, in a 24 hour period would fall outside standard values for probable weight change in a 24 hour period and trigger a re-query of the one or more physiological sensors for a higher quality set of sensor values.

In one embodiment, the set of standard values is specific for a physiological sensor type, as shown in block 450. For example, each sensor type may have more or less sensitivity to background "noise" or inherent noise in the system. For example, each sensor type may have specific range of values that are physiologically relevant.

In one embodiment, sets of sensor values from two or more sensor types may be compared with one another to assign quality values to each set of sensor values. For example, a set of sensor values from a heart rate monitor indicating a heart rate of 10 beats/min in combination with an otherwise normal respiration rate or a video image of the individual walking around normally might indicate an issue with the heart rate sensor values, resulting in a low quality value being assigned to the heart rate sensor values, thus triggering re-query of the heart rate monitor.

In one embodiment, the set of standard values for use in comparing with the set of sensor values are stored in the computing device, e.g., using any of the data storage medium described herein. In one embodiment, the set of standard values are stored in one or more lookup tables. In one embodiment, the one or more lookup tables including sets of standard values are precalculated and stored in the computing device, e.g., in static program storage or in hardware. In one embodiment, the one or more lookup tables including sets of standard values are calculated as part of programs or algorithms run on the computing device. In one embodiment, the set of standard values are specific for a given physiological parameter, e.g., a physiologically relevant range. In one embodiment, the set of standard values are specific to a given sensor type, e.g., the amount of noise and the value of data or information above the noise may be specific to a sensor type.

FIG. 5 illustrates further aspects of system 100 depicted in FIG. 1. Computing device 120 of system 100 includes processor 130 and is programmed to retain the set of sensor values if the assigned quality value of the set of sensor values meets or exceeds a minimum quality value threshold 160. In one embodiment, only sensor values able to contribute to a reliable medical diagnosis are retained. In one embodiment, the minimum quality value threshold represents a quality value of sensor values that ensures that the value will contribute to a reliable medical diagnosis. For example, the assigned quality value may arbitrarily range from 1 to 100. The minimum quality value threshold may be a single cutoff value, e.g., 50, in which case sensors values with an assigned quality value less than 50 will not be retained while sensor values with an assigned quality value of 50 or more will be retained. In one embodiment, the minimum quality value threshold is determined by the type of sensor and the type of data or information collected. For example, a first type of physiological sensor may be very accurate such that low quality data or information is still very useful while a second type of sensor may be considerably less accurate such that only high quality data or information is useful for a reliable medical diagnosis. In one embodiment, the minimum quality value threshold may be determined by a physician or other care provider. For example, the physician or other care provider may choose to put more weight on one type of sensor value relative to another sensor value and as such adjust the minimum quality value threshold for each sensor type accordingly to ensure a reliable medical diagnosis. In one embodiment, the minimum quality value threshold is a single value for a given sensor type. In one embodiment, the minimum quality value threshold may shift over time. For example, a first minimum quality value threshold may be set at 20, sensor values with an assigned quality value of at least 20 are retained and in subsequent queries, the minimum quality value threshold is increased to 30 or 40 to see if better data or information can be collected. In this example, the sensor values with assigned quality values of 20 are good enough for diagnosis, but sensor values with assigned quality values of 30 or 40 would be better, if obtainable.

In one embodiment, computing device 120 with processor 130 is programmed to retain the set of sensor values in one or more data storage devices operably connected to the computing device, as shown in block 500. Non-limiting examples of data storage devices including removable disks, ROM, flash memory devices, hard disk drive, and volatile and non-volatile RAM have been discussed above herein.

In one embodiment, computing device 120 with processor 130 is programmed to update the at least one flag if the assigned quality value of the set of sensor values meets or exceeds the minimum quality value threshold, as shown in block 165. In one embodiment, the computing device is programmed to update the at least one flag by pulling the at least one flag down, e.g., turning off or inactivating the flag. In one embodiment, the computing device is programmed to update the at least one flag by resetting the flag. In one embodiment, resetting the flag includes proceeding to the next step in the schedule of need-measurement criteria. In one embodiment, resetting the flag includes switching on or activating the flag to be ready to query the physiological sensors as part of the next step in the schedule of need-measurement criteria.

In one embodiment, the computing device 120 including processor 130 is programmed to report the set of sensor values to a user, as illustrated in block 510. In one embodiment, the user is the individual. In one embodiment, the user is a third party, e.g., a physician, nurse, family member, or other caregiver. In one embodiment, the user is a third party associated with a system maintenance service configured to set up and maintain the physiological sensors and/or computing device. In one embodiment, the computing device is programmed to report the set of sensor values to the user through a communications means, as shown in block 520. In one embodiment, the communications means includes a wired transmission, e.g., through a telephone line, cable, or optical fiber. In one embodiment, the communications means includes a wireless transmission, e.g., an audible report from a speaker associated with the computing device, a Bluetooth transmission, a radio transmission, and the like. In one embodiment, the computing device is programmed to report a set of sensor values by transmitting the set of sensor values through a transmission means, e.g., a telephone or the Internet. In one embodiment, the computing device is programmed to produce an audible alert or transmit an alert to a handheld device, e.g., a cell phone or pager, indicating that a set of sensor values is available for viewing on a local device, e.g., a computing device. In one embodiment, the computing device is programmed to report a set of sensor values to the individual or a healthcare provider by sending the information to a handheld device, e.g., a cell phone. In one embodiment, the computing device is programmed to report the set of sensor values through an e-mail message or alert. In one embodiment, the computing device is operable to report a set of sensor values by generating a printout of the set of sensor values. For example, the computing device, if set up in the residence of the individual, may be programmed to generate an onscreen report accessible by the individual.

In one embodiment, the computing device is programmed to report to the user the retained set of sensor values that met or exceeded the minimum quality value threshold, as illustrated in block 530. In one embodiment, the retained set of sensor values is used to diagnose or monitor a diagnosis of an individual. For example, the retained set of sensor values may be used to monitor various parameters, e.g., tissue swelling, weight gain, and/or labored breathing, to determine whether or not the individual is developing decompensated heart failure and needs medical attention. In one embodiment, the computing device is programmed to only report the retained set of sensor values. In one embodiment, the computing device is programmed to report to the user sensor values that failed to meet or exceed the minimum quality value threshold, as shown in block 540. In one embodiment, reporting the sensor values that failed to meet or exceed the minimum quality value threshold may allow a physician, caregiver, the individual, system maintenance service, or others to monitor issues with the sensors and/or the processing. For example, repeated reports containing sets of sensor values that failed to meet or exceed the minimum quality value threshold may indicate to a system maintenance service that a service call is warranted to check and/or replace the sensors.

Returning to FIG. 5, computing device 120 including processor 130 is optionally programmed to re-query at least one of the one or more physiological sensors to acquire an updated set of sensor values representative of the one or more measured physiological parameters of the individual if the assigned quality value of the set of sensor values fails to meet or exceed the minimum quality value threshold, as shown in block 550. In one embodiment, computing device 120 is programmed to query at least one of the one or more physiological sensors until the assigned quality value of the sensor values meets or exceeds the minimum quality value threshold and satisfies the need-measurement criteria. In one embodiment, it may become apparent that one sensor of a sensor type is malfunctioning as indicated by routinely sending low quality data or information that fails to meet or exceed the minimum quality value threshold. As such, a second sensor of the sensor type may be queried to improve the data quality. In one embodiment, a message is sent to the individual, a physician, a caregiver, a facility manager, a system maintenance service, and/or other entity to indicate that one or more of the physiological sensors is malfunctioning or not properly placed in the residence, e.g., routinely not meeting the minimum quality value threshold.

Figure 6:
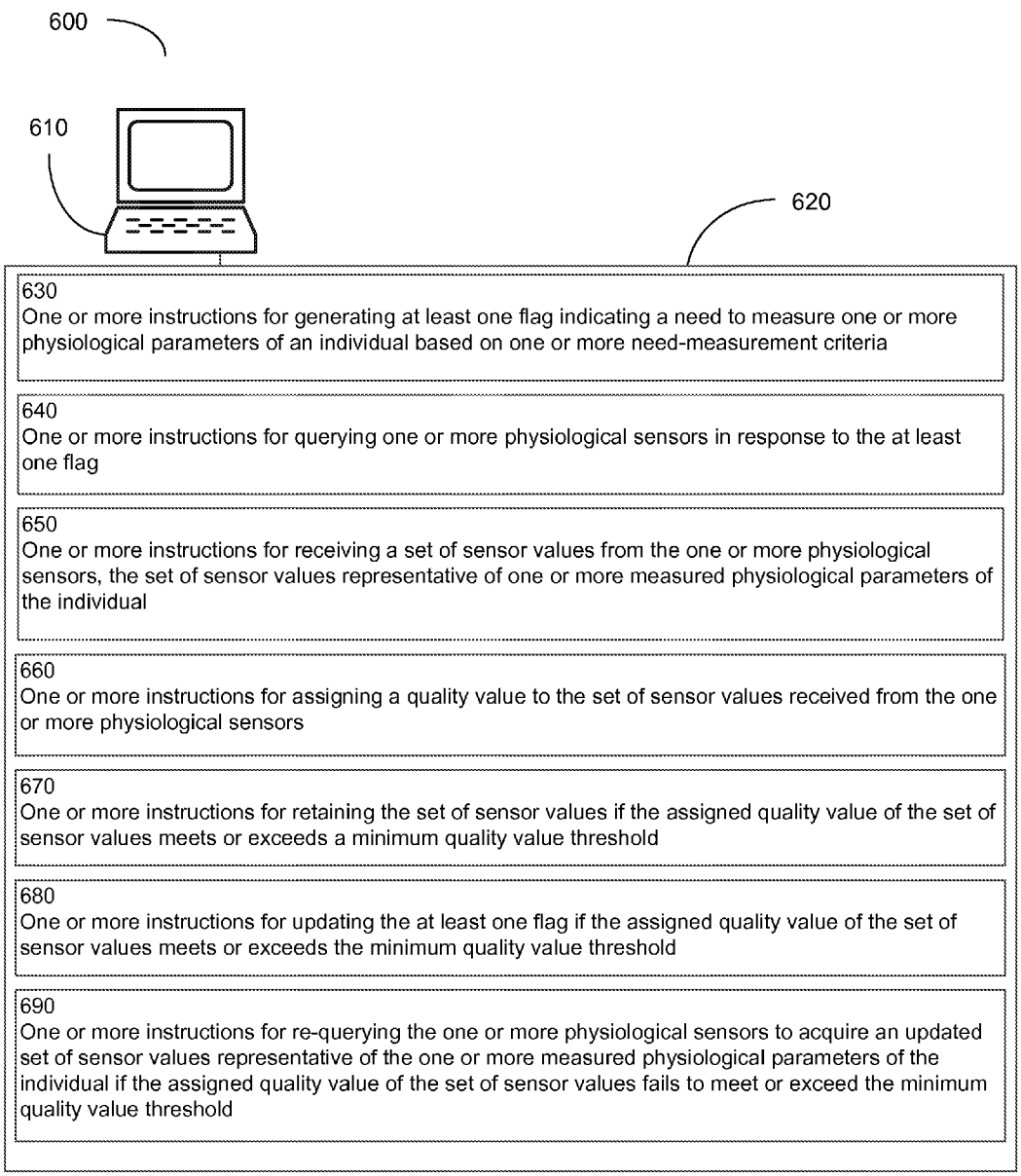
FIG. 6 is a schematic of a system.

FIG. 6 illustrates aspects of a system for controlling acquisition of information from one or more sensors. System 600 includes computing processor 610 and non-transitory signal-bearing medium 620 bearing one or more instructions for controlling acquisition of information from one or more sensors. Non-transitory signal-bearing medium 620 further includes one or more instructions 630 for generating at least one flag indicating a need to measure one or more physiological parameters of an individual based on one or more need-measurement criteria; one or more instructions 640 for querying one or more physiological sensors in response to the at least one flag; one or more instructions 650 for receiving a set of sensor values from the one or more physiological sensors, the set of sensor values representative of one or more measured physiological parameters of the individual; one or more instructions 660 for assigning a quality value to the set of sensor values received from the one or more physiological sensors; one or more instructions 670 for retaining the set of sensor values if the assigned quality value of the set of sensor values meets or exceeds a minimum quality value threshold; one or more instructions 680 for updating the at least one flag if the assigned quality value of the set of sensor values meets or exceeds the minimum quality value threshold; and one or more instructions 690 for re-querying the one or more physiological sensors to acquire an updated set of sensor values representative of the one or more measured physiological parameters of the individual if the assigned quality value of the set of sensor values fails to meet or exceed the minimum quality value threshold.

Non-transitory signal-bearing medium 620 stores instructions and/or data for use in controlling acquisition of information from one or more sensors. In an embodiment, non-transitory signal-bearing medium 620 can be computer readable media. In an embodiment, non-transitory signal-bearing medium 620 can be recordable-type media. Computer readable media may also be recordable-type media, and the qualities of being "computer readable" and "recordable-type" should not be construed as being mutually exclusive, though in some cases a computer readable media may not be a recordable-type media, and vice versa. Machine readable media include volatile and nonvolatile, removable and non-removable media implemented in any method or technology for storage of information such as machine readable instructions, data structures, program modules, or other data. Non-transitory signal-bearing media include, but are not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other media which can be used to store the desired information and which can be accessed by computing device 610. In a further embodiment, computer storage media may include a group of computer storage media devices. In an embodiment, machine readable media may include an information store. In an embodiment, an information store may include a quantum memory, a photonic quantum memory, or atomic quantum memory. Combinations of any of the above may also be included within the scope of non-transitory machine readable media.

Figure 7:
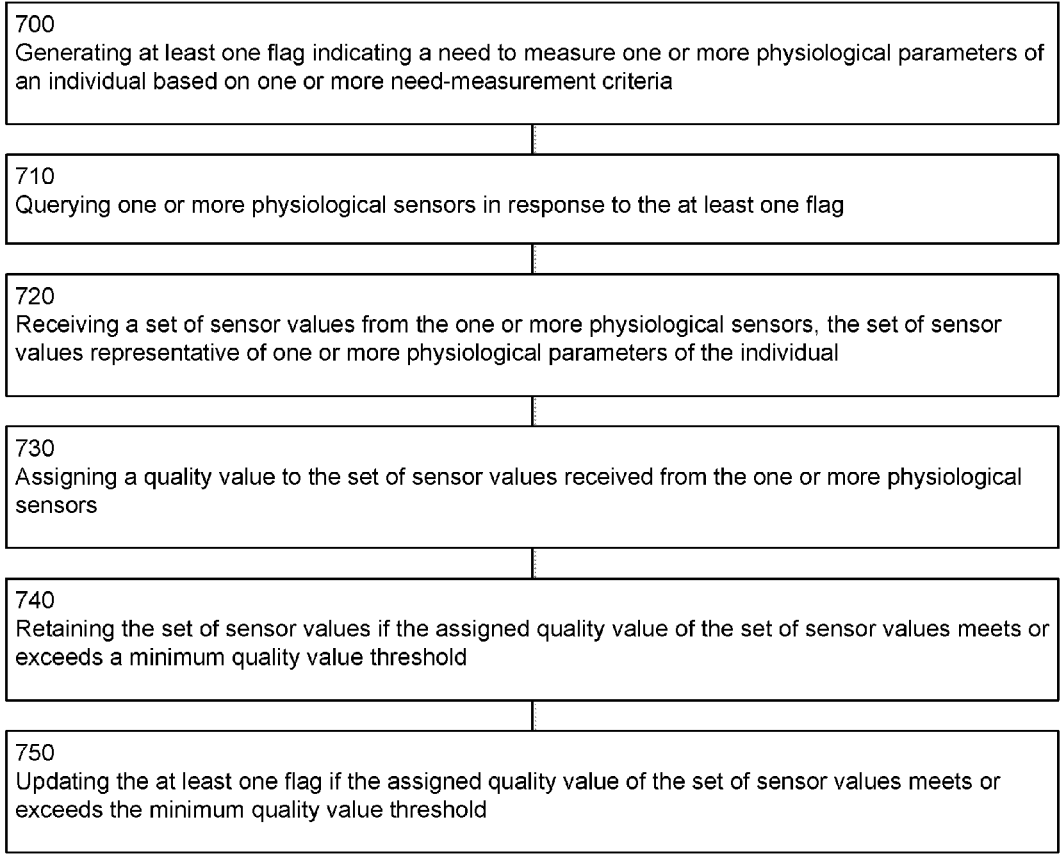
FIG. 7 is a flowchart of a method of controlling acquisition of information from physiological sensors.

FIG. 7 illustrates a method for controlling acquisition of information from one or more sensors. The embodiment of the method illustrated in FIG. 7 shows generating at least one flag indicating a need to measure one or more physiological parameters of an individual based one or more need-measurement criteria in block 700; querying one or more physiological sensors in response to the at least one flag in block 710; receiving a set of sensor values from the one or more physiological sensors, the set of sensor values representative of one or more physiological parameters of the individual in block 720; assigning a quality value to the set of sensor values received from the one or more physiological sensors in block 730; retaining the set of sensor values if the assigned quality value of the set of sensor values meets or exceeds a minimum quality value threshold in block 740; and updating the at least one flag if the assigned quality value of the set of sensor values meets or exceeds the minimum quality value threshold in block 750. In one embodiment, the method for controlling acquisition of information from one or more sensors is implemented on a computing device, non-limiting examples of which have been described herein.

In one embodiment, the method for controlling acquisition of information from one or more sensors is performed electronically and/or automatically using a computing device operably connected to one or more physiological sensors and includes, but is not limited to, electronically and/or automatically generating at least one flag indicating a need to measure one or more physiological parameters of an individual based on one or more need-measurement criteria; electronically and/or automatically querying one or more physiological sensors in response to the at least one flag; electronically and/or automatically receiving a set of sensor values from the one or more physiological sensors, the set of sensor values representative of one or more physiological parameters of the individual; electronically and/or automatically assigning a quality value to the set of sensor values received from the one or more physiological sensors; electronically and/or automatically retaining the set of sensor values if the assigned quality value of the set of sensor values meets or exceeds a minimum quality value threshold; and electronically and/or automatically updating the at least one flag if the assigned quality value of the set of sensor values meets or exceeds the minimum quality value threshold.

FIG. 8 depicts further aspects of a method such as illustrated in FIG. 7 for controlling acquisition of information from one or more sensors. Block 700 shows generating at least one flag indicating a need to measure one or more physiological parameters of an individual based on one or more need-measurement criteria and includes optional blocks 800, 810, 820, and 830. In one embodiment, generating at least one flag includes activating a pre-existing flag that is part of a monitoring schedule that includes one or more need-measurement criteria. In one embodiment, generating at least one flag includes adding a new flag to a pre-existing monitoring schedule. In an embodiment shown in block 800, the method optionally includes generating the at least one flag indicating a need to measure one or more physiological parameters of an individual based on a time of day. For example, the method may include generating a flag every hour to measure an average heart rate or a flag every 24 hours to measure a weight. In an embodiment shown in block 810, the method optionally includes generating the at least one flag indicating a need to measure one or more physiological parameters of an individual based on a number of sensor values needed over time for a reliable diagnosis. In an embodiment shown in block 820, the method optionally includes generating the at least one flag indicating a need to measure one or more physiological parameters of an individual based on a number of sensor values with assigned quality values that meet the minimum quality value threshold. For example, at least one flag may be repeatedly generated/activated until sufficient quality data or information is acquired. In an embodiment shown in block 830, the method optionally includes generating the at least one flag indicating a need to measure one or more physiological parameters of an individual based on the health status of the individual. For example, flags may be generated more or less frequently, depending upon the individual's medical condition and/or the severity of the medical condition. For example, flags that are part of a monitoring schedule may be activated/inactivated, depending upon the individual's medical condition and/or severity of the medical condition. In an embodiment shown in block 840, the one or more need-measurement criteria are updateable. For example, as an individual's condition improves or deteriorates, a physician or other caregiver may change the need-measurement criteria, e.g., the types of physiological sensors queried and/or the frequency of query. In an embodiment shown in block 850, the one or more need-measurement criteria are part of a monitoring schedule. For example, a physician or caregiver may prescribe a schedule for monitoring a medical condition of an individual, the schedule including need-measurement criteria, e.g., time and frequencies of sensor queries.

FIG. 9 depicts further aspects of the method illustrated in FIG. 7 for controlling acquisition of information from one or more sensors. Block 710 shows querying one or more physiological sensors in response to the at least one flag and includes optional blocks 900, 910, 920, 930, 940, 950, and 960. In an embodiment shown in block 900, the method optionally includes querying the one or more physiological sensors through one or more wireless transmissions, e.g., through a radio, microwave, or optical transmission from the computing device or parts thereof and received by the one or more physiological sensors. In one embodiment, the method optionally includes querying the one or more physiological sensors through one or more wired transmissions, e.g., through an electrical connection. In some embodiments, both wireless and wired transmissions may be used to query the one or more physiological sensors.

In an embodiment shown in block 910 of FIG. 9, the method optionally includes querying the one or more physiological sensors in a time dependent manner. In an embodiment shown in block 920, the method optionally includes querying the one or more physiological sensors in a sensor type dependent manner. In an embodiment shown in block 930, the method optionally includes querying the one or more physiological sensors based on the identity of the individual. In one embodiment, the method includes querying the one or more physiological sensors in a time and sensor dependent manner. For example, a first sensor type may be queried every hour while a second sensor type is queried every 30 minutes. In an embodiment shown in block 940, the method optionally includes querying the one or more physiological sensors based on a number of previous queries to at least one of the one or more physiological sensor. In an embodiment shown in block 950, the method optionally include querying the one or more physiological sensors based on the assigned quality value of a previously received set of sensor values. In an embodiment shown in block 960, the method optionally includes querying the one or more physiological sensors based on a health status of the individual.

In an embodiment shown in block 970 of FIG. 9, the method optionally includes querying one or more non-contact physiological sensors. In one embodiment, the method includes querying one or more of an audio sensor, an image capture device, a micro impulse radar-based sensors, an ultra-wideband radar-based sensor, or a thermal sensor, as illustrated in block 980. Non-limiting examples of sensors have been described above herein. In an embodiment shown in block 990, the method optionally includes querying one or more physiological sensors associated with one or more items in a residential space, e.g., walls, doors, furniture, utensils, and the like.

FIG. 10 depicts further aspects of the method illustrated in FIG. 7 for controlling acquisition of information from one or more sensors. Block 720 shows receiving a set of sensor values from the one or more physiological sensors, the set of sensor values representative of one or more physiological parameters of the individual and optionally includes receiving the set of sensor values through one or more wireless transmissions in block 1000 and/or receiving the set of sensor values through one or more wired transmissions in block 1010. Non-limiting examples of physiological sensors have been described above herein.

In one embodiment, the method includes receiving a set of sensor values from the one or more physiological sensors, the set of sensor values representative of one or more physiological parameter of the individual diagnostic for heart failure, non-limiting examples of which include tissue swelling, respiratory sounds (e.g., labored breathing), respiratory rate, heart rate, activity level, autonomic balance, weight, and/or blood oxygenation.

In one embodiment, as illustrated in block 1020, the method optionally includes receiving the set of sensor values from one or more non-contact physiological sensors. In one embodiment, as illustrated in block 1030, the method optionally includes receiving the set of sensor values from one or more audio sensors. In one embodiment, as illustrated in block 1040, the method optionally includes receiving the set of sensor values from one or more image capture devices. In one embodiment, as illustrated in block 1050, the method optionally includes receiving the set of sensor values from one or more micro impulse radar-based sensors. In one embodiment, as illustrated in block 1060, the method optionally includes receiving the set of sensor values from one or more thermal sensors. In one embodiment, as illustrated in block 1070, the method optionally includes receiving the set of sensor values from one or more ultra-wideband radar-based sensors. In one embodiment, as illustrated in block 1080, the method optionally includes receiving the set of sensor values from one or more physiological sensors associated with one or more items in a residential space. In general, the method can include receiving a set of sensor values from one or more of a single type of physiological sensors or from various types of physiological sensors, depending upon the physiological parameters being measured and the need-measurement criteria.

Figure 11:
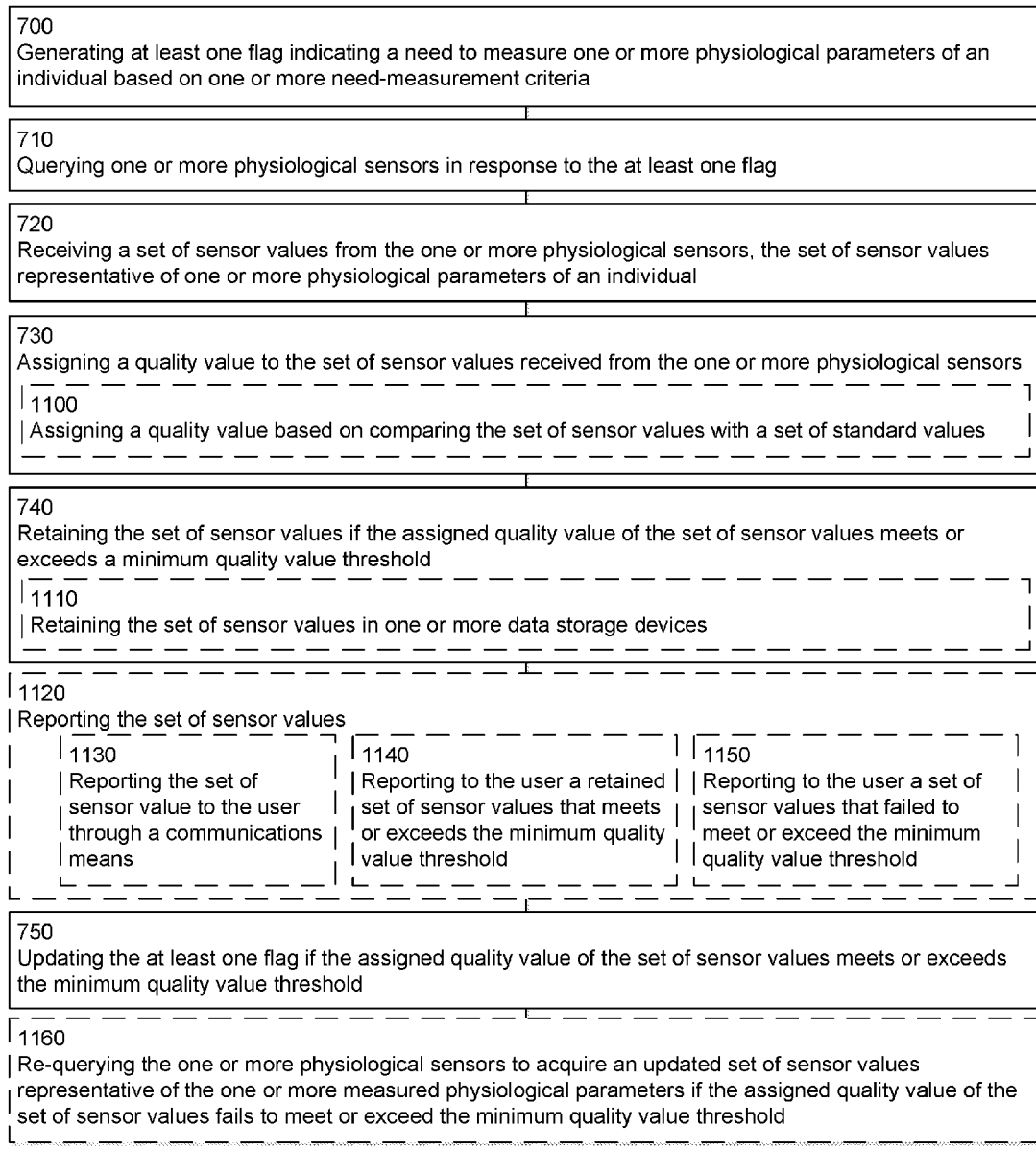
FIG. 11 is a flowchart illustrating aspects of a method such as shown in FIG. 7.

FIG. 11 depicts further aspects of the method illustrated in FIG. 7 for controlling acquisition of information from one or more sensors. Block 730 shows assigning a quality value to the set of sensor values received from the one or more physiological sensors. Block 730 optionally includes block 1100. Block 1100 illustrates optionally assigning a quality value based on comparing the set of sensor values with a set of standard values. In one embodiment, the set of standard values includes sensor values with sufficient signal-to-noise to provide reliable date for medical diagnosis. In one embodiment, the set of standard values includes a set of standard values representing a relevant range of values for a specific physiological, e.g., sensor values that are physiologically possible. In one embodiment, the set of standard values is stored on a computing device. In one embodiment, the set of standard values is part of a lookup table. In one embodiment, the set of standard values is specific for a physiological sensor type.

Block 740 of FIG. 11 shows retaining the set of sensor values if the quality value of the set of sensor values meets or exceeds a minimum quality value threshold and optionally includes block 1110. Block 1110 illustrates retaining the set of sensor values in one or more data storage devices operably connected to the computing device. Non-limiting examples of data storage devices have been described above herein.

Returning to FIG. 11, the method optionally includes reporting the set of sensor values to a user, as illustrated in block 1120. In one embodiment, the user is the individual. In one embodiment, the user is a third party, e.g., a physician, nurse, family member, or other caregiver. In one embodiment, the user is a third party associated with a system maintenance service configured to set up and maintain the physiological sensors and/or computing device. In one embodiment, reporting the set of sensor values to the user includes reporting the sensor values to the user through a communications means, as shown in block 1130. In one embodiment, the communications means includes a wired transmission, e.g., through a telephone line, cable, or optical fiber. In one embodiment, the communications means includes a wireless transmission, e.g., an audible report from a speaker associated with the computing device, a Bluetooth transmission, a radio transmission, and the like. In one embodiment, reporting the set of sensor values to the user includes transmitting the set of sensor values through a transmission means, e.g., a telephone or the Internet. In one embodiment, reporting the set of sensor values to the user includes producing an audible alert or transmitting an alert to a handheld device, e.g., a cell phone or pager, indicating that a set of sensor values is available for viewing on a local device, e.g., a computing device. In one embodiment, reporting the set of sensor values to the individual and/or a third party includes sending the information to a handheld device, e.g., a cell phone. In one embodiment, reporting the set of sensor values to a user includes sending an e-mail message or alert. In one embodiment, reporting the set of sensor values to a user includes generating a printout of the set of sensor values. In one embodiment, reporting the set of sensor values to a user includes generating an onscreen report accessible by the user.

In one embodiment, the reporting the set of sensor values to the user includes reporting to the user a retained set of sensor values that meets or exceeds the minimum quality value threshold, as illustrated in block 1140. In one embodiment, the retained set of sensor values is used to diagnose or monitor a diagnosis of an individual. For example, the retained set of sensor values may be used to monitor various parameters, e.g., tissue swelling, weight gain, and/or labored breathing, to determine whether or not the individual is developing decompensated heart failure and needs medical attention. In one embodiment, reporting the set of sensor values includes only reporting the retained set of sensor values. In one embodiment, reporting the set of sensor values to the user includes reporting sets of sensor values that failed to meet or exceed the minimum quality value threshold, as shown in block 1150. In one embodiment, reporting the sensor values that failed to meet or exceed the minimum quality value threshold may allow a physician, caregiver, the individual, system maintenance service, or others to monitor issues with the sensors and/or the processing. For example, repeated reports containing sets of sensor values that failed to meet or exceed the minimum quality value threshold may indicate to a system maintenance service that a service call is warranted to check and/or replace the sensors.

In an embodiment illustrated in block 1160 of FIG. 11, the method optionally includes re-querying the one or more physiological sensors to acquire an updated set of sensor values representative of the one or more measured physiological parameters if the assigned quality value of the set of sensor values fails to meet or exceed the minimum quality value threshold.

Figure 12:
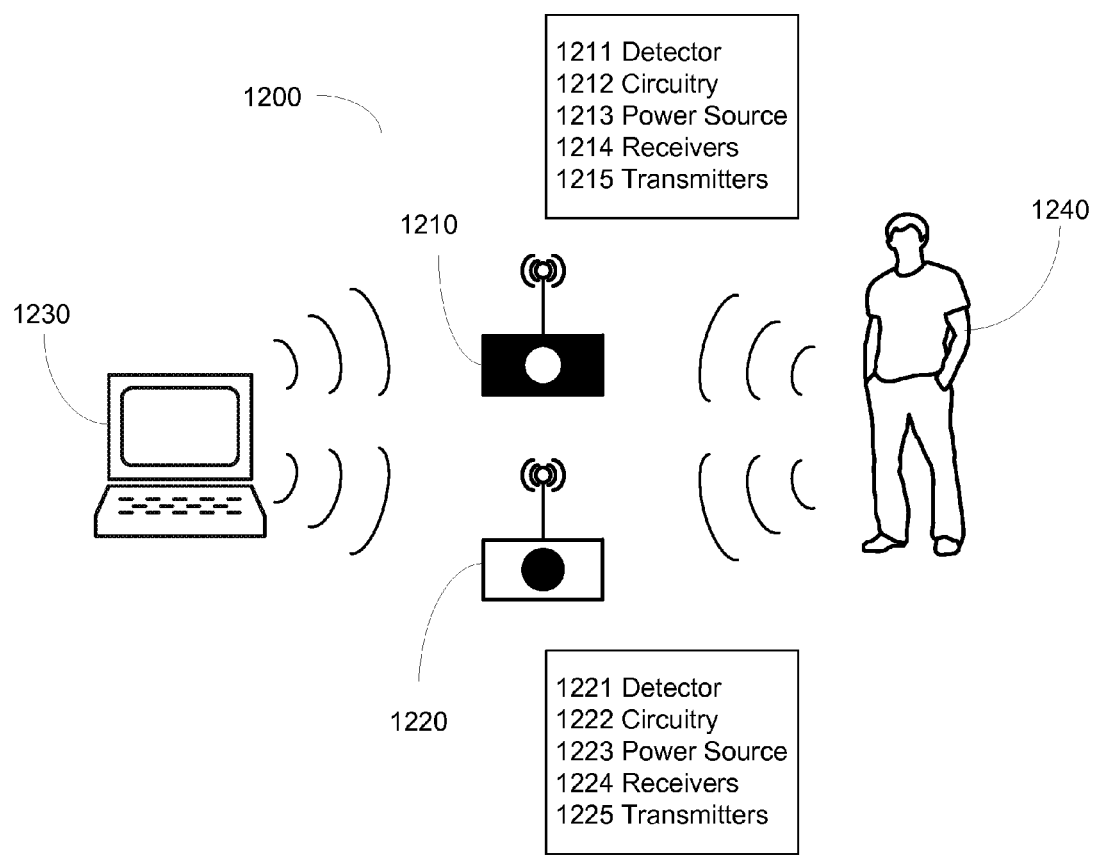
FIG. 12 is a schematic of a system for controlling acquisition of information from physiological sensors.

With reference to FIG. 12, shown is a schematic of a system for controlling acquisition of information from one or more sensors. System 1200 includes one or more condition sensors 1210 and one or more physiological sensors 1220. The one or more condition sensors 1210 and the one or more physiological sensors 1220 are operably connected to computing device 1230. In one embodiment, as shown in FIG. 12, the one or more condition sensors 1210 and the one or more physiological sensors 1220 are in wireless communication with computing device 1230. In one embodiment, one or more of the one or more condition sensors 1210 and/or one or more of the one or more physiological sensors 1220 are connected to computing device 1230 through one or more wires, e.g., electrical wires or fiber optic cables.

The one or more condition sensors 1210 are configured to measure one or more conditions of individual 1240 relative to the one or more physiological sensors 1220. In one embodiment, the one or more conditions of the individual relative to the one or more physiological sensors include at least one of proximity, visibility, movement, or position of the individual relative to the one or more physiological sensors. In one embodiment, the one or more conditions of the individual relative to the one or more physiological sensors include one or more individual biometrics including, but not limited to, facial recognition, retinal scan, finger prints, or speech recognition.

In one embodiment, the one or more condition sensors can include one or more proximity sensors configured to measure the proximity of individual 1240 to the one or more physiological sensors 1220. The one or more proximity sensors can include one or more sensors configured to detect the presence of the individual relative to the one or more physiological sensors. For example, the one or more proximity sensors may be used to assess how close the individual is to one or more physiological sensors. The proximity of the individual to a physiological sensor may dictate the quality of the information received from the physiological sensor (see, e.g., Michahelles et al., (2004) *Proceedings of the Eighth International Symposium on Wearable Computers* (ISWC'04) 1530-0811/04, which is incorporated herein by reference). The one or more proximity sensors can include one or more inductive, capacitive, or optical proximity sensors. Other non-limiting examples of proximity sensors include capacitive displacement, Doppler sensors, laser rangefinder, magnetic, passive optical, passive thermal infrared, photocell, radar, or ultrasonic sensors.

In one embodiment, the one or more condition sensors 1210 include one or more sensors responsive, without physically contacting the individual, to an impedance, capacitance, permittivity, reflectivity, absorption, or electrical activity of the individual. For example, a sensor including a capacitive proximity sensor element configured to sense a condition of an individual without physically contacting the individual is described in U.S. Patent Application Pub. No. 2008/0246495, which is incorporated herein by reference. In one embodiment, a reflection or reflectivity may include an acoustic, light, or radio wave reflectivity.

In one embodiment, the one or more condition sensors 1210 can include one or more biometric sensors configured to measure one or more biometric parameters of individual 1240 to determine if individual 1240 is the object of query by the one or more physiological sensors 1220. For example, in a residence in which more than one individual resides, the one or more biometric sensors can be used to identify a given individual in a given area of the residential space and query the one or more physiological sensors appropriately. For example, one or more biometric sensors may be used to confirm the identity of an individual prior to querying one or more physiological sensors. In one embodiment, the type and timing of which physiological sensor type is queried can be conditioned based on which individual has entered a room or is scheduled for a measurement. This is of particular use in a multi-individual residence in which either only one individual in the residence is being monitored or in which multiple individuals in the residence are being monitored. In the first instance, it is optimal to only take measurements of the individual who needs monitoring. In the second instance, it is optimal to perform individual-specific monitoring for each of the individuals needing monitoring in the residence. Non-limiting examples of biometric methods include fingerprint recognition, facial recognition, signature recognition, voice recognition, vein matching, retinal scan, iris recognition, keystroke dynamics, DNA, and the like. For example, a facial recognition sensor can include an image capture device to capture a facial image and one or more facial recognition algorithms (e.g., principal component analysis, linear discriminate analysis, elastic bunch graph matching, hidden Markov model, and/or dynamic link matching or a three-dimensional matching technique) to identify facial features and compare with a database of known facial features, e.g., facial features of the individual(s) residing in the residence and being medically monitored. In one embodiment, the one or more condition sensors 1210 can include one or more biometric sensors configured to assess the identity of an individual 1240 relative to the one or more physiological sensors 1220.

In one embodiment, the one or more condition sensors 1210 can include one or more line-of-sight sensors configured to determine if individual 1240 is in a clear line-of-sight relative to one or more physiological sensors 1220. For example, certain physiological sensor types, e.g., micro impulse radar for measuring heart rate, require a clear line of site between the sensor and the individual.

In one embodiment, the one or more condition sensors 1210 can include one or more motion sensors configured to measure movement relative to one or more physiological sensors 1220. For example, a motion sensor can sense that individual 1240 has entered a specific portion of a residential space and is in sufficient range for measurement by one of the one or more physiological sensors. For example, a motion sensor can sense how fast individual 1240 is moving through a specific portion of a residential space and whether the speed of the individual is too fast or slow for reliable measurement by one of the one or more physiological sensors. Non-limiting examples of motion sensors include passive infrared sensors, ultrasonic sensors, microwave sensors, or tomographic detectors (for measuring disturbances in radio waves). In one embodiment, the motion sensor is activated when the individual is within range, wherein the range can include an optimal range for measuring one or more physiological parameter with the one or more physiological sensors. In one embodiment, the motion sensor can be used to determine if an individual is present, i.e., has entered a room or other space in the residence containing one or more physiological sensors.

In one embodiment, the one or more condition sensors 1210 include one or more contact sensors. The one or more contact sensors can be incorporated into one or more items in the residential space or other space occupied by the individual. For example, contact sensors can be incorporated into a computer mouse, a chair, a toilet seat, a mat associated with a bathroom or kitchen sink, a bed, or any other item that an individual might come in contact with during the course of a day. In one embodiment, the one or more contact sensors include touch sensors, e.g., a force sensor, capacitive sensor, or piezoelectric sensor (from, e.g., RobotShop Distribution Inc., Swanton, Vt.).

In one embodiment, the system actively monitors (e.g., detects, tracks, etc.) individual 1240 by using at least one of computerized axial tomography, fiber optic thermometry, infrared thermography, magnetic resonance imaging, magnetic resonance spectroscopy, microwave thermography, microwave dielectric spectroscopy, positron emission tomography, ultrasound reflectometry, spectroscopic imaging, visual imaging, infrared imaging, single photon emission computed tomography, or the like.

In one embodiment, the system includes a subject tracking system (not shown in figures). For example, in one embodiment, the system includes a subject tracking system for updating in real time an individual's virtual location in a virtual space corresponding to the physical location of the individual in a physical space, such as a living room, community room, bedroom, or other physical space within a residence.

In one embodiment, the one or more condition sensors 1210 can include one or more time sensors configured to measure a time relative to an individual and one or more physiological sensors 1220. For example, a clock may be used to time when one or more physiological sensors are queried. This information may be combined with one or more other conditions of the individual, e.g., proximity or motion relative to a specific physiological sensor. In other words, a need-measurement criteria, e.g., a specific time of day, and associated flag may indicate a need for a measurement, but if the individual is not in the vicinity of the physiological sensor at the specific time of day, the query to the sensor is not completed. In one embodiment, the time sensor is a clock. In one embodiment, the time sensor is a sensor configured to measure time intervals, e.g., seconds, minutes, or hours between measurements.

In one embodiment, the one or more condition sensors 1210 can include one or more light sensors configured to measure the amount of light in the vicinity of individual 1240 relative to the one or more physiological sensors 1220. For example, a light sensor may be used to sense that a light has been switched on in a specific room of a residential space and as such individual 1240 is in sufficient range for one of the one or more physiological sensors. For example, a light sensor may be used to measure whether there is sufficient light available to take measurements with one of the one or more physiological sensors, for example, an image capture device or video camera requiring a certain amount of ambient light to capture useful image data from the individual. Non-limiting examples of light sensors include photocells (e.g., photo-emissive cells, photo-conductive cells, or photo-voltaic cells), photodiode, photoresistors (e.g., light dependent resistor (LDR)), charge-coupled devices, photomultipliers, and the like.

In one embodiment, the one or more condition sensors 1210 can include one or more accelerometers configured to measure the acceleration of individual 1240 relative to the one or more physiological sensors 1220.

In one embodiment, the one or more condition sensors 1210 can include one or more image capture devices configured to measure an image of the individual relative to the one or more physiological sensors 1220. In one embodiment, the one or more image capture devices can be incorporated into one or more motion detectors, one or more proximity detectors, one or more biometric sensors, etc. The one or more image capture devices can include one or more of a camera, passive or active scanner, a video camera, and the like.

The one or more condition sensors 1210 further include at least one detector 1211, circuitry 1212, power source 1213, one or more receivers 1214, and one or more transmitters 1215, non-limiting examples of which have been described above herein.

In one embodiment, the one or more condition sensors comprise at least one transmission unit including an antenna configured for wireless communication with the computing device. In one embodiment, the one or more condition sensors are in optical communication with the computing device.

System 1200 further includes one or more physiological sensors 1220. In one embodiment, the one or more physiological sensors 1220 include one or more non-contact physiological sensors, configured to sense one or more physiological parameters of an individual without directly contacting the individual. Non-limiting examples of non-contact physiological sensors have been described above herein. In one embodiment, the one or more physiological sensors are incorporated into or associated with one or more residential items. For example, the one or more physiological sensors may be incorporated into or associated with walls, windows, doors, or furniture of a residential space. For example, the one or more physiological sensors may be incorporated into or associated with furniture, appliances, utensils, bathroom scales, toilets, and the like. In one embodiment, the one or more physiological sensors include one or more wearable or implantable physiological sensors.

The one or more physiological sensors 1220 further include at least one detector 1221, circuitry 1222, power source 1223, one or more receivers 1224, and one or more transmitters 1225, non-limiting examples of which have been described above herein.

The one or more physiological sensors 1220 are configured to detect one or more physiological parameters of an individual, e.g., tissue swelling, respiratory sounds, respiratory rate, heart rate, activity level, autonomic balance, weight, blood oxygenation. The one or more physiological parameters of an individual can further include, but are not limited to, height, facial features, visible physical malformations, eye characteristic, appearance of skin, appearance of hair, appearance of nails, respiratory sounds, body temperature, blood gas level, brain electrical activity, agitation, perspiration, tremor, facial expression, blood chemistries, blood cell counts, platelet counts, antibody titer, calcium level, blood antigen type, tissue antigen type, evidence of a pathogen exposure, lipid levels, perception of pain level, body movement, gait, stiffness, evidence of cognition state, dehydration, pain, malaise, injury, rigor, fever, light-headedness or dizziness, dry mouth, thirst, shortness of breath, nausea, weakness, sleepiness, hearing loss or problem, vision loss or problem, constipation, diarrhea, flatulence, urinary incontinence, loss of smell, loss of voice or problem, loss of ability to walk, to write, or to use a limb. Generally, the one or more physiological parameters measured by the one or more physiological sensors 1220 are diagnostic for an acute and/or chronic condition, e.g., heart failure, that is being monitored on a routine basis in a space occupied by the individual, e.g., a residential space.

In one embodiment, the one or more physiological sensors comprise at least one transmission unit including an antenna configured for wireless communication with the computing device. In one embodiment, the one or more physiological sensors are in optical communication with the computing device.

In one embodiment, at least one of the one or more condition sensors is also a physiological sensor. For example, at least one of the one or more condition sensors can include an image capture device configured to capture an image of an individual relative to a physiological sensor but also configured to capture an image of an individual that has diagnostic value.

In one embodiment, the one or more condition sensors are incorporated into the one or more physiological sensors. For example, one or more proximity sensors may be incorporated into a physiological sensor to detect the distance between an individual and the physiological sensor. Similarly, the one or more condition sensors may be incorporated proximal to the one or more physiological sensors. In one embodiment, the one or more condition sensors are not necessarily in the same location as the one or more physiological sensors. For example, a light sensor detecting a light coming on in a room may be in one part of a room while the one or more physiological sensors that operate optimally in the presence of light may be in another part of the room. In one embodiment, the one or more condition sensors are associated with items in a residential space, e.g., mounted on walls, incorporated into doors, installed in a light-switch, or incorporated into furniture or other residential items.

FIG. 13 illustrates further aspects of a system such as shown in FIG. 12. System 1200 includes computing device 1230 including processor 1300. Computing device 1230 including processor 1300 is programmed to query at least one of the one or more condition sensors to initiate measurement of one or more conditions of an individual relative to the one or more physiological sensors in block 1310; receive a set of condition sensor value from the at least one of the one or more condition sensors, the set of condition sensor values representative of the one or more conditions of the individual relative to the one or more physiological sensors in block 1320; assign a predictive value to the set of condition sensor values in block 1330; query at least one of the one or more physiological sensors to measure one or more physiological parameters of the individual if the assigned predictive value of the set of condition sensor values meets or exceeds a minimum predictive value threshold in block 1340; and re-query at least one of the one or more condition sensors if the assigned predictive value of the set of condition sensors values fails to meet or exceed the minimum predictive value threshold in block 1350.

In one embodiment, condition sensor values from a first type of one or more condition sensors are combined with condition sensor values from a second type of one or more condition sensors to determine a predictive value. For example, a time condition may be combined with a proximity condition, such that the one or more physiological sensors are queried only at a specific time and when the individual is in appropriate proximity. For example, a time condition may be combined with a light condition and a motion condition, such that the one or more physiological sensors are queried only at a specific time and when there is sufficient lighting and the individual is motionless, for example, relative to the one or more physiological sensors. For example, measurements from one or more motion sensors can be used to indicate that someone has entered a particular room while a biometric sensor can be used to determine if the individual who has entered the room is the appropriate target of query by the one or more physiological sensors.

FIG. 14 illustrates further aspects of a system such as that shown in FIG. 12. In some embodiments, computing device 1230 including processor 1300 is optionally programmable to query the one or more condition sensors 1210 to initiate measurement of one or more of proximity, visibility, line-of-sight, motion, acceleration, biometrics, or position of the individual relative to the one or more physiological sensors, as illustrated in block 1400.

In one embodiment, computing device 1230 including processor 1300 is optionally programmed to query the one or more condition sensors in response to a triggering event, as illustrated in block 1410. In an embodiment shown in block 1420, the triggering event includes input from a motion detector. For example, the one or more condition sensors may be queried in response to an individual walking into a portion of a residential space monitored by a motion detector. For example, a motion detector may be used to trigger measurement from one or more biometric sensors. For example, a motion detector may be used to trigger measurement from one or more accelerometers. For example, turning on a room light and consequently activating a light sensor can be used to trigger measurement from one or more proximity, biometric, or image capture devices. In an embodiment shown in block 1430, the triggering event includes input from a timing device. For example, the one or more condition sensors may be queried periodically on a schedule, e.g., every minute, every few minutes, every hour, every day at a certain time, and the like, depending upon the need-measurement criteria, e.g., how often a measurement is needed from a specific physiological sensor. In an embodiment shown in block 1440, the triggering event includes input from a proximity sensor. For example, the one or more condition sensors may be queried only when the individual is an appropriate distance from the one or more condition sensors.

In one embodiment, computing device 1230 including processor 1300 is optionally programmed to query the at least one of the one or more condition sensors to initiate measurement of the one or more conditions of the individual relative to the one or more physiological sensors in response to a flag indicating a need to measure the one or more physiological parameters of the individual based on one or more need-measurement criteria, as illustrated in block 1450. The need-measurement criteria include, but are not limited to, a time of day, a sensor type, an interval of time since a previous measurement, a number of sensor values with assigned quality values that meet the minimum quality value threshold, and/or a health status of the individual. The need-measurement criteria can be updateable and/or part of a monitoring schedule as described above herein.

Figure 15:
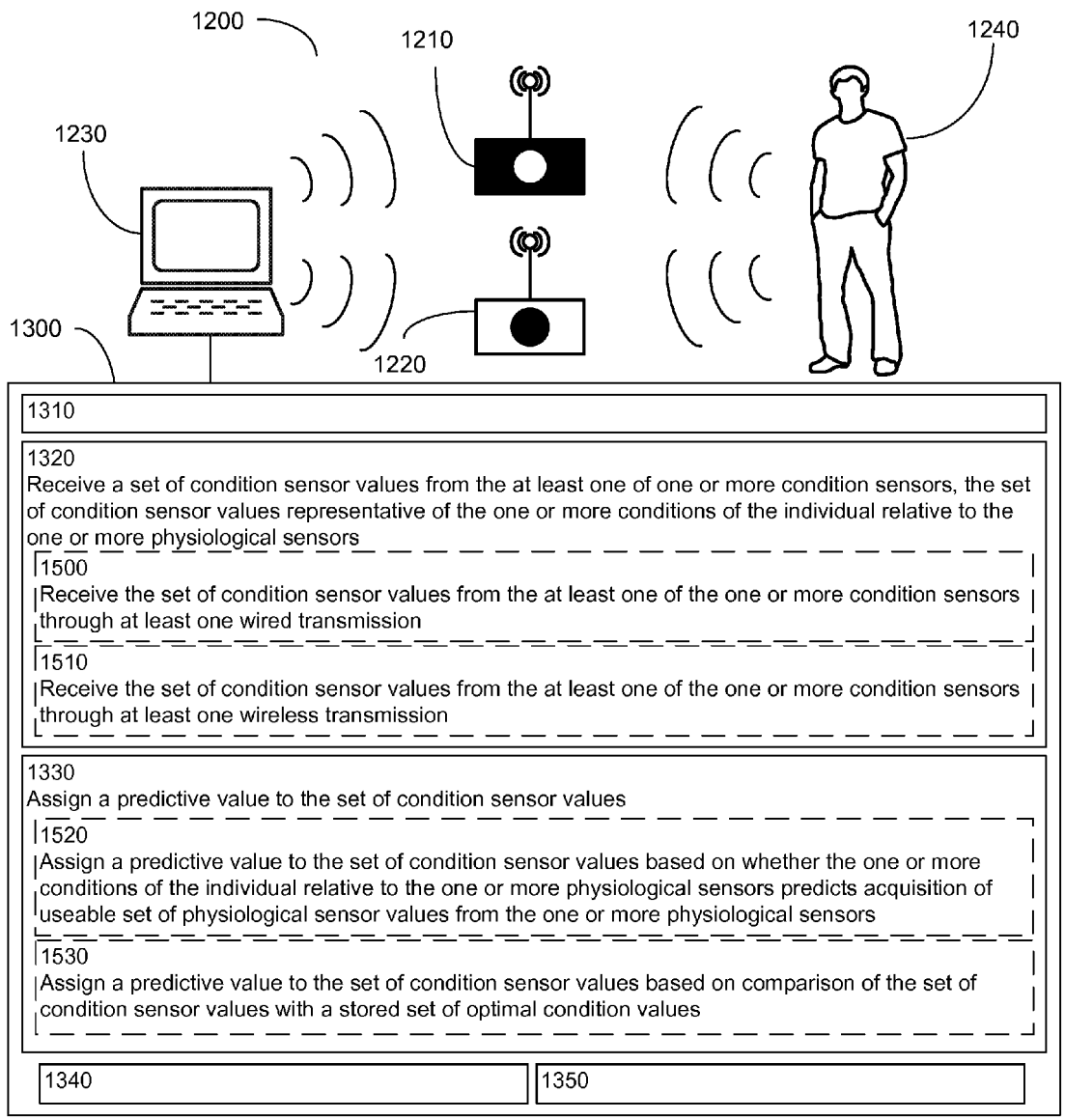
FIG. 15 is a schematic of an embodiment of a system such as shown in FIG. 12.

FIG. 15 shows further aspects of a system such as that shown in FIG. 12. Computing device 1230 including processor 1300 is programmed to receive a set of condition sensor values from the at least one of the one or more condition sensors, the set of condition sensor values representative of the one or more conditions of the individual relative to the one or more physiological sensors, as shown in block 1320. Block 1320 further optionally includes block 1500 and 1510. Block 1500 shows computing device 1230 optionally programmed to receive the set of condition sensor values from the at least one of the one or more condition sensors through at least one wired transmission. Block 1510 shows computing device 1230 optionally programmed to receive the set of condition sensor values from the at least one of the one or more condition sensors through at least one wireless transmission.

FIG. 15 further illustrates computing device 1230 programmed to assign a predictive value to the set of condition sensor values in block 1330. Block 1330 further includes optional blocks 1520 and 1530. Block 1520 shows computing device 1230 optionally programmed to assign a predictive value to the set of condition sensor values based on whether the one or more conditions of the individual relative to the one or more physiological sensors predicts acquisition of useable set of physiological sensor values from the one or more physiological sensors, e.g., a set of physiological sensor values with a quality value that meets a minimum quality value threshold. For example, is the individual in close enough proximity to the one or more physiological sensors to acquire useable data? For example, is there sufficient lighting for the one or more physiological sensors to acquire useable data? For example, is the individual motionless enough for the one or more physiological sensors to acquire useable data?

In one embodiment, as shown in block 1530, the predictive value is assigned to the set of condition sensor values based on comparison of the set of condition sensor values with a stored set of optimal condition values. The optical condition values can include a range of condition values predicted to allow for acquisition of useable information from the one or more physiological sensors. For example, the set of condition sensor values can include a range of distances between the individual and a given type of physiological sensor for which quality information can be obtained. For example, the set of condition sensor values can include a range of lighting conditions under which a given physiological sensor can acquire quality information. For example, the set of condition sensor values can include one or more biometric parameters of an individual, e.g., facial features, finger prints, voice pattern, retinal pattern, etc. For example, the set of condition sensor values can include a range of movement of the individual relative to a given type of physiological sensor for which quality information can be obtained. In one embodiment, the stored set of optimal condition values is stored in the computing device. In one embodiment, the stored set of optimal condition values is part of a lookup table. In one embodiment, the stored set of optimal condition values is specific for a condition sensor type.

Figure 16:
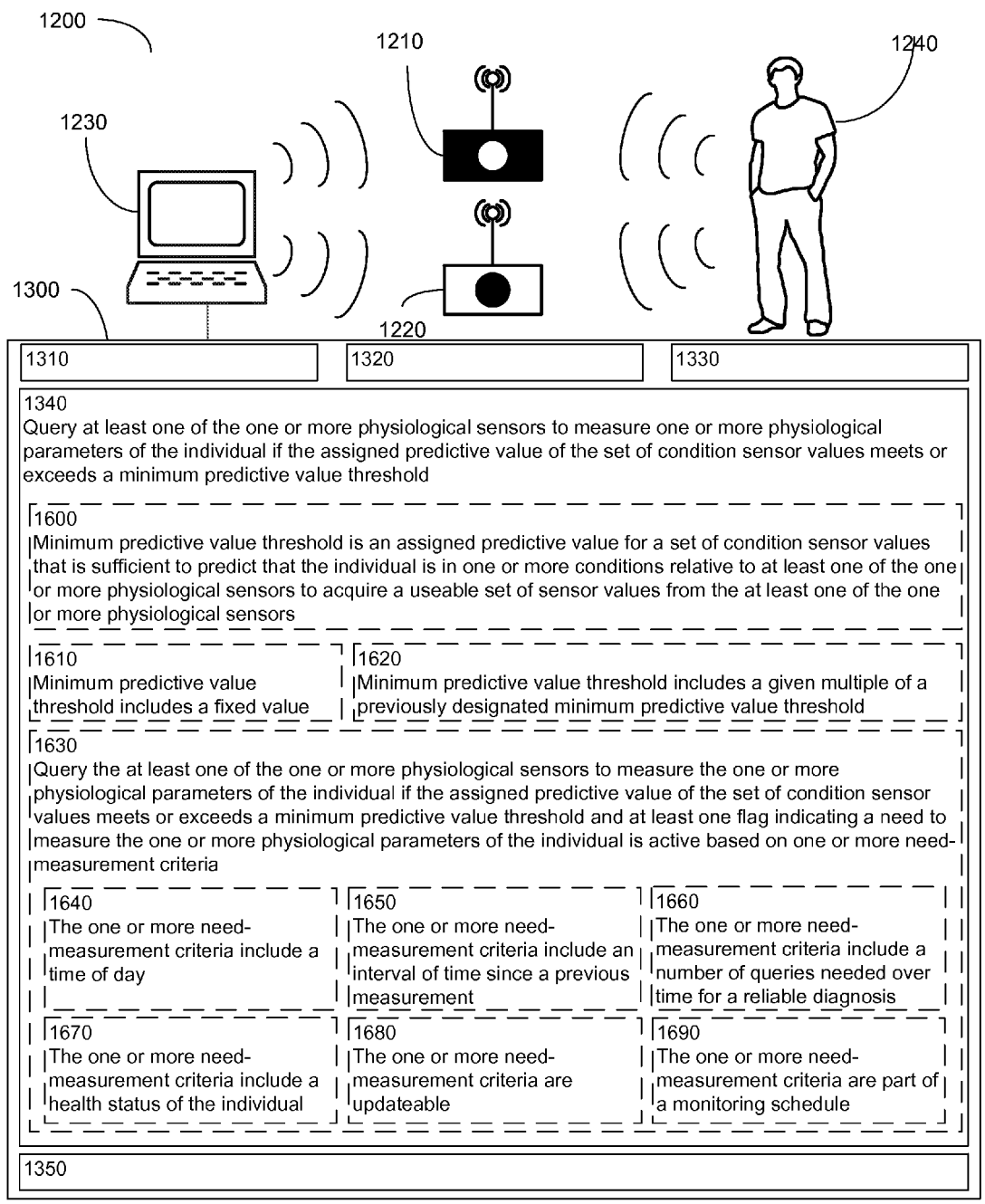
FIG. 16 is a schematic of an embodiment of a system such as shown in FIG. 12.

FIG. 16 illustrate further aspects of a system such as that shown in FIG. 12. Computing device 1230 including processor 1300 is programmed to query at least one of the one or more physiological sensors to measure one or more physiological parameters of the individual if the assigned predictive value of the set of condition sensor values meets or exceeds a minimum predictive value threshold, as shown in block 1340. In one embodiment, as shown in block 1600, the minimum predictive value threshold is an assigned predictive value for a set of condition sensor values that is sufficient to predict that the individual is in one or more conditions relative to at least one of the one or more physiological sensors to acquire a useable set of sensor values from the at least one of the one or more physiological sensors. For example, the assigned predictive value may arbitrarily range from 1 to 100. In one embodiment, as shown in block 1610, the minimum predictive value threshold includes a fixed value, e.g., a value of 50. In this instance, a set of condition sensor values with an assigned predictive value less than 50 would indicate that the individual is in a condition, e.g., poor lighting or proximity, that would predict poor quality data or information from a physiological sensor and as such, the physiological sensor is not queried. Conversely, a set of condition sensor values with an assigned predictive value equal to or greater than 50 would indicate that the individual is in a condition, e.g., adequate lighting or proximity, that predicts good quality data or information from a physiological sensor and as such, the physiological sensor is queried. In one embodiment, the minimum predictive value threshold is determined by the condition relative to the type of physiological sensor and the type of data or information collected. For example, a first type of physiological sensor, e.g., a microphone, would be predicted to acquire high quality data or information under the condition of low lighting while a second type of physiological sensor, e.g., an image capture device, would be predicted to acquire lesser quality data or information under the same condition of low lighting. In one embodiment, the minimum predictive value threshold may be determined by a physician or other care provider. For example, the physician or other care provider may choose to put more weight on one type of condition sensor value relative to another condition sensor value and as such adjust the minimum predictive value threshold for each sensor type accordingly to ensure appropriate prediction of quality data or information from a queried physiological sensor. In one embodiment, as illustrated in block 1620, the minimum predictive value threshold includes a given multiple of a previously designated minimum predictive value threshold. For example, a first minimum predictive value threshold may be 20, while a second minimum predictive value is 1.2 times the previous minimum predictive value threshold of 24. For example, a first minimum predictive value threshold may be set at 20, condition sensor values with an assigned predictive value of at least 20 result in querying the one or more physiological sensors. With subsequent queries of the one or more condition sensors, the minimum predictive value threshold is increased to 30 or 40 to see if better data or information, e.g., condition of the individual relative to one or more physiological sensors, can be attained. In this example, the condition sensor values with assigned predictive values of 20 indicate that the individual is in an adequate condition, e.g., close enough, to query a physiological sensor, but condition sensor values with assigned quality values of 30 or 40 indicate that the individual is in a better condition, e.g., optimal distance, to query the physiological sensor.

Returning to FIG. 16, block 1630 illustrates computing device 1230 with processor 1300 optionally programmed to query the at least one of the one or more physiological sensors to measure the one or more physiological parameters of the individual is the assigned predictive value of the set of condition sensor values meets or exceeds the minimum predictive value threshold and at least one flag indicating a need to measure the one or more physiological parameters of the individual is active based on one or more need-measurement criteria. For example, the condition sensors may indicate that the individual is in an optimal condition to acquire information from the physiological sensors, if there is no need to acquire information, e.g., no flag is currently active, then the physiological sensors are not queried. In one embodiment, the one or more need-measurement criteria include a time of day, as illustrated in block 1640. In one embodiment, the one or more need-measurement criteria include an interval of time since a previous measurement, as illustrated in block 1650. In one embodiment, the one or more need-measurement criteria include a number of queries needed over time for a reliable diagnosis, as illustrated in block 1660. In one embodiment, the one or more need-measurement criteria include a health status of the individual, as illustrated in block 1670. In one embodiment, the one or more need-measurement criteria are updateable, as illustrated in block 1680. In one embodiment, the one or more need measurement criteria are part of a monitoring schedule, as illustrated in block 1690.

Figure 17:
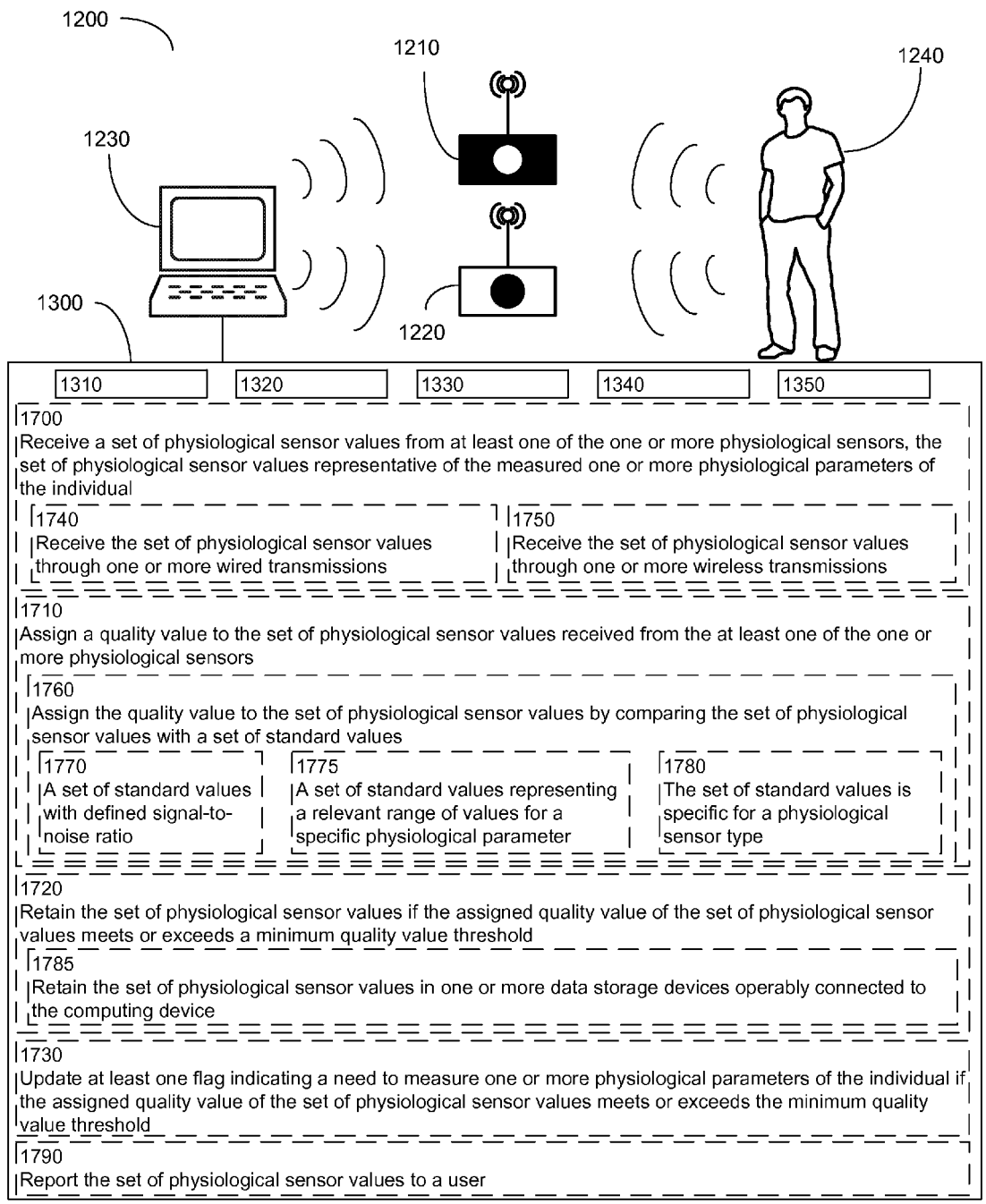
FIG. 17 is a schematic of an embodiment of a system such as shown in FIG. 12.

FIG. 17 illustrates further aspects of a system such as that shown in FIG. 12. In one embodiment, computing device

1230 of system 1200 is programmed to receive a set of physiological sensor values from at least one of the one or more physiological sensors, the set of physiological sensor values representative of the measured one or more physiological parameters of the individual, in block 1700; assign a quality value to the set of physiological sensor values received from the at least one of the one or more physiological sensors, in block 1710; retain the set of physiological sensor values if the assigned quality value of the set of physiological sensor values meets or exceeds a minimum quality value threshold, in block 1720; and update at least one flag indicating a need to measure one or more physiological parameters of the individual if the assigned quality value of the set of physiological sensor values meets or exceeds the minimum quality value threshold, in block 1730.

In one embodiment, computing device 1230 is optionally programmed to receive the set of physiological sensor values from at least one of the one or more physiological sensors through one or more wired transmissions, as illustrated in block 1740. For example, the one or more physiological sensors may be directly wired to the computing device. For example, the one or more physiological sensors may be wired to an amplifier which is then connected to the computing device. In one embodiment, the computing device is operable to receive the set of physiological sensor values from at least one of the one or more physiological sensors through one or more wireless transmissions, as illustrated in block 1750. For example, the one or more physiological sensors may be in radio or optical communication with the computing device. For example, the one or more physiological sensors may be in radio communication with an amplifier, which in turn is in wired or wireless communication with the computing device.

In one embodiment, computing device 1230 is programmed to assign a quality value to the set of physiological sensor values received from the at least one of the one or more physiological sensors by comparing the set of physiological sensor values with a set of standard values, as illustrated in block 1760. In one embodiment, as described above herein, the quality value is an indicator of whether or not the physiological sensor values are of high enough quality to contribute to a reliable medical diagnosis. In one embodiment, the quality value is an arbitrary number between 0 and 100. The quality value is assigned based on the quality of the data or information received from the at least one of the one or more physiological sensors. In one embodiment, the assessment of the quality of the data or information received is dependent upon the type of sensor being used and the allowable variability.

In one embodiment, the set of standard values is a set of physiological sensor values adequate enough to provide a reliable medical diagnosis. In one embodiment, the set of standard values is a set of standard values with defined signal-to-noise ratio, as illustrated in block 1770. For example, in some embodiments, a signal-to-noise ratio above 1 may provide sufficient information. In some embodiments, a signal-to-noise ratio significantly above 1 may be needed to provide sufficient information. In one embodiment, the sensor itself may be capable of subtracting noise from the physiological sensor values before transmitting them to the computing device. In one embodiment, it may still be necessary to determine a signal-to-noise ratio or to subtract noise associated with transmitting and receiving the physiological sensor values from the one or more physiological sensors.

In one embodiment, the set of standard values is a set of standard values representing a relevant range of values for a specific physiological parameter, as illustrated in block 1775. In one embodiment, the relevant range of values for a specific physiological parameter includes values that are physiologically possible, e.g., a physiologically possible heart rate or respiration rate or 24 hour weight change. In one embodiment, the set of standard values is specific for a physiological sensor type, as illustrated in block 1780. For example, the amount of noise inherent in the sensor and the value of data above the noise may be specific to a physiological sensor type.

In one embodiment, sets of physiological sensor values from two or more physiological sensor types may be compared with one another to assign quality values to each set of physiological sensor values. For example, a set of physiological sensor values from a heart rate monitor indicating a heart rate of 10 beats/min in combination with an otherwise normal respiratory rate or video image of the individual might indicate an issue with the heart rate sensor values, resulting in a low quality value being assigned to the heart rate sensor values.

In one embodiment, the set of standard values for use in comparing with the set of physiological sensor values are stored in the computing device. In one embodiment, the set of standard values are stored in one or more lookup tables. In one embodiment, the one or more lookup tables including sets of standard values are precalculated and stored in the computing device, e.g., in static program storage or in hardware. In one embodiment, the one or more lookup tables including sets of standard values are calculated as part of programs or algorithms run on the computing device. In one embodiment, the set of standard values are specific for a given physiological parameters, e.g., a physiologically relevant range.

Block 1720 of FIG. 17 shows computing device 1230 optionally programmed to retain the set of physiological sensor values if the assigned quality value of the set of physiological sensor values meets or exceeds a minimum quality value threshold. Block 1785 shows that computing device 1230 is optionally programmed to retain the set of physiological sensor values in one or more data storage devices operably connected to the computing device. Non-limiting examples of one or more data storage devices have been described above herein.

Block 1790 of FIG. 17 illustrates computing device 1230 optionally programmed to report the set of physiological sensor values to a user, e.g., to the individual, a physician, a caregiver, a system maintenance service, and/or other interested parties. In one embodiment, the computing device including the processor is programmed to report to the user only retained sets of physiological sensor values, i.e., sets of physiological sensor values that meet or exceed the minimum quality value threshold. In one embodiment, the computing device including the processor is programmed to report to the user sets of physiological sensor values that failed to meet or exceed the minimum quality value threshold. For example, in some embodiments, information regarding physiological sensor values that routinely failed to meet or exceed the minimum quality value threshold may indicate operational or technical issues with the one or more physiological sensors and/or their placement. In one embodiment, the computing device including the processor is programmed to report the set of physiological sensor values to the user through a wireless communication, examples of which have been described above herein.

FIG. 18 shows a flow diagram 1800 for controlling acquisition of information from one or more sensors. In some embodiments, the steps of flow diagram 1800 are carried out by a computing device that includes a processor, the computing device operable to perform a series of operations configured to control acquisition of information from one or more sensors. At block 1805, query at least one of one or more condition sensors in response to a flag indicating a need to measure one or more physiological parameters of an individual to initiate measurement of one or more conditions of the individual relative to one or more physiological sensors. At block 1810, receive a set of condition sensor values from the at least one of the one or more condition sensors. At block 1815, assign a predictive value to the set of condition sensor values. If a minimum predictive value threshold is not met or exceeded at block 1820, return to block 1805 to again query at least one of one or more conditions sensors. If the minimum predictive value threshold is met or exceeded at block 1825, proceed to block 1830 and query at least one of the one or more physiological sensors to measure one or more physiological parameters of the individual. At block 1835, receive a set of physiological sensor values from the at least one of the one or more physiological sensors. At block 1840, assign a quality value to the set of physiological sensor values. If a minimum quality value threshold is not met or exceeded at block 1845, return to block 1805 to again query at least one of the one or more condition sensors to ensure that one or more conditions of the individual are still optimal to query the one or more physiological sensors and if so, proceed with re-querying the one or more physiological sensors. If the minimum quality value threshold is met or exceeded at block 1850, proceed to block 1855 and retain the set of physiological sensor values. At block 1860, update the at least one flag and as appropriate return to block 1805 to query the one or more condition sensors. At block 1865, report a set of sensor values to a user, wherein the set of sensor values can include sensor values received from the one or more condition sensors and/or the one or more physiological sensors.

FIG. 19 illustrates a method for controlling acquisition of information from one or more sensors. The method includes receiving a set of condition sensor values for an individual from at least one of one or more condition sensors in response to one or more queries, the set of condition sensor values representative of one or more conditions of the individual relative to one or more physiological sensors at block 1900; assigning a predictive value to the set of condition sensor values at block 1910; querying at least one of the one or more physiological sensors to measure one or more physiological parameters of the individual if the assigned predictive value of the set of condition values meets or exceeds a minimum predictive value threshold at block 1920; and re-querying at least one of the one or more condition sensors if the assigned predictive value of the set of condition sensor values fails to meet or exceed the minimum predictive value threshold at block 1930.

FIG. 20 illustrates further aspects of the method shown in FIG. 19. In one embodiment, the method includes querying the at least one of the one or more condition sensors to measure one or more conditions of the individual relative to the one or more physiological sensors, as shown in block 2000. In one embodiment, the method includes querying the at least one of the one or more condition sensors in response to a triggering event, as shown in block 2010. In one embodiment, the triggering event includes input from a motion detector. For example, the one or more condition sensors may be queried in response to an individual walking into a portion of a residential space monitored by a motion detector. For example, a motion detector may be used to trigger measurement from one or more biometric sensors. For example, a motion detector may be used to trigger measurement from one or more accelerometers. For example, turning on a room light and consequently activating a light sensor can be used to trigger measurement from one or more proximity, biometric, or image capture devices. In one embodiment, the triggering event includes input from a timing device. For example, the one or more condition sensors may be queried periodically on a schedule, e.g., every minute, every few minutes, every hour, every day at a certain time, and the like, depending upon the need-measurement criteria, e.g., how often a measurement is needed from a specific physiological sensor. In one embodiment, the triggering event includes input from a proximity sensor indicating that the individual is positioned in appropriate proximity for sensing with the one or more condition sensors. In one embodiment, the triggering event includes input from a contact sensor indicating that the individual is in a particular position, e.g., touching a computer mouse at a desk, sitting in a chair or on the toilet, standing on a mat associated with a bathroom or kitchen sink, and the like.

In one embodiment, the method optionally includes querying the at least one of the one or more conditions sensors in response to at least one flag indicating a need to measure one or more physiological parameters of the individual, as shown in block 2020. In one embodiment, the at least one flag indicating the need to measure the one or more physiological parameters of the individual is generated based on one or more need-measurement criteria, as illustrated in block 2030. The need-measurement criteria can include, but are not limited to, a time of day, a sensor type, an interval of time since a previous measurement, a number of sensor values with assigned quality values that meet the minimum quality value threshold, and/or a health status of the individual. The need-measurement criteria can be updateable and/or part of a monitoring schedule as described above herein.

In one embodiment, querying the at least one of the one or more condition sensors to measure one or more conditions of the individual relative to the one or more physiological sensors includes, but is not limited to, querying at least one of one or more motion sensors, one or more light sensors, one or more proximity sensors, and/or one or more biometric sensors, as illustrated in block 2040.

Returning to FIG. 20, the method includes receiving a set of condition sensor values for an individual from at least one of one or more condition sensors in response to one or more queries. In one embodiment, the method includes receiving the set of condition sensor values for the individual from at least one of one or more motion sensors, as shown in block 2050. In one embodiment, the method includes receiving the set of condition sensor values for the individual from at least one of one or more light sensors, as shown in block 2055. In one embodiment, the method includes receiving the set of condition sensor values for the individual from at least one of one or more proximity sensors, as shown in block 2060. In one embodiment, the method includes receiving the set of condition sensor values for the individual from at least one of one or more contact sensors, as shown in block 2065. In one embodiment, the method includes receiving the set of condition sensor values for the individual from at least one of one or more biometric sensors, as shown in block 2070. In one embodiment, the method includes receiving the set of condition sensor values for the individual from one or more wireless transmissions, as shown in block 2075. Non-limiting examples of condition sensors and means for wireless (and wired) transmission have been described above herein.

FIG. 21 illustrates further aspects of the method of FIG. 19. The method includes assigning a predictive value to the set of condition sensor values and optionally includes block 2100 assigning a predictive value based on comparing the set of condition sensor values with a stored set of optimal condition values. The method including block 2100 optionally includes blocks 2110, 2120, and 2130. Block 2110 shows wherein the stored set of optimal condition values is stored in a computing device. Block 2120 shows wherein the stored set of optimal condition values is part of a lookup table. In one embodiment, the lookup table including sets of optimal condition values is pre-calculated and stored in the computing device, e.g., in static program storage or in hardware. In one embodiment, the lookup table including sets of optimal condition values calculated as part of programs or algorithms run on the computing device. Block 2130 shows wherein the stored set of optimal condition values is specific for a condition sensor type.

The method further includes querying at least one of the one or more physiological sensors to measure one or more physiological parameters of the individual if the assigned predictive value of the set of condition sensor values meets or exceeds a minimum predictive value threshold. The method including querying at least one of one or more physiological sensors can include querying at least one of one or more non-contact physiological sensors 2150, querying at least one of one or more micro impulse radar-based sensors 2155, querying at least one of one or more ultra-wideband radar-based sensors 2160, querying at least one of one or more of an audio sensor or an image capture device 2165, and/or querying at least one of one or more thermal sensors 2170. In one embodiment, the method includes querying the at least one of the one or more physiological sensors through one or more wireless transmissions 2175. In one embodiment, the method includes querying the at least one of the one or more physiological sensors through one or more wired transmissions 2180.

In one embodiment, the method includes querying the at least one of the one or more physiological sensors to measure one or more physiological parameters of the individual diagnostic for heart failure, as illustrated in block 2185. Non-limiting examples of physiological parameters diagnostic for heart failure include, but are not limited to, tissue swelling, respiratory sounds, respiratory rate, heart rate, activity level, autonomic balance, weight, or blood oxygenation. In one embodiment, the method includes re-querying the at least one of the one or more condition sensors until the assigned predictive value of the set of condition sensor values meets or exceeds the minimum predictive value threshold, as shown in block 2190.

Figure 22:
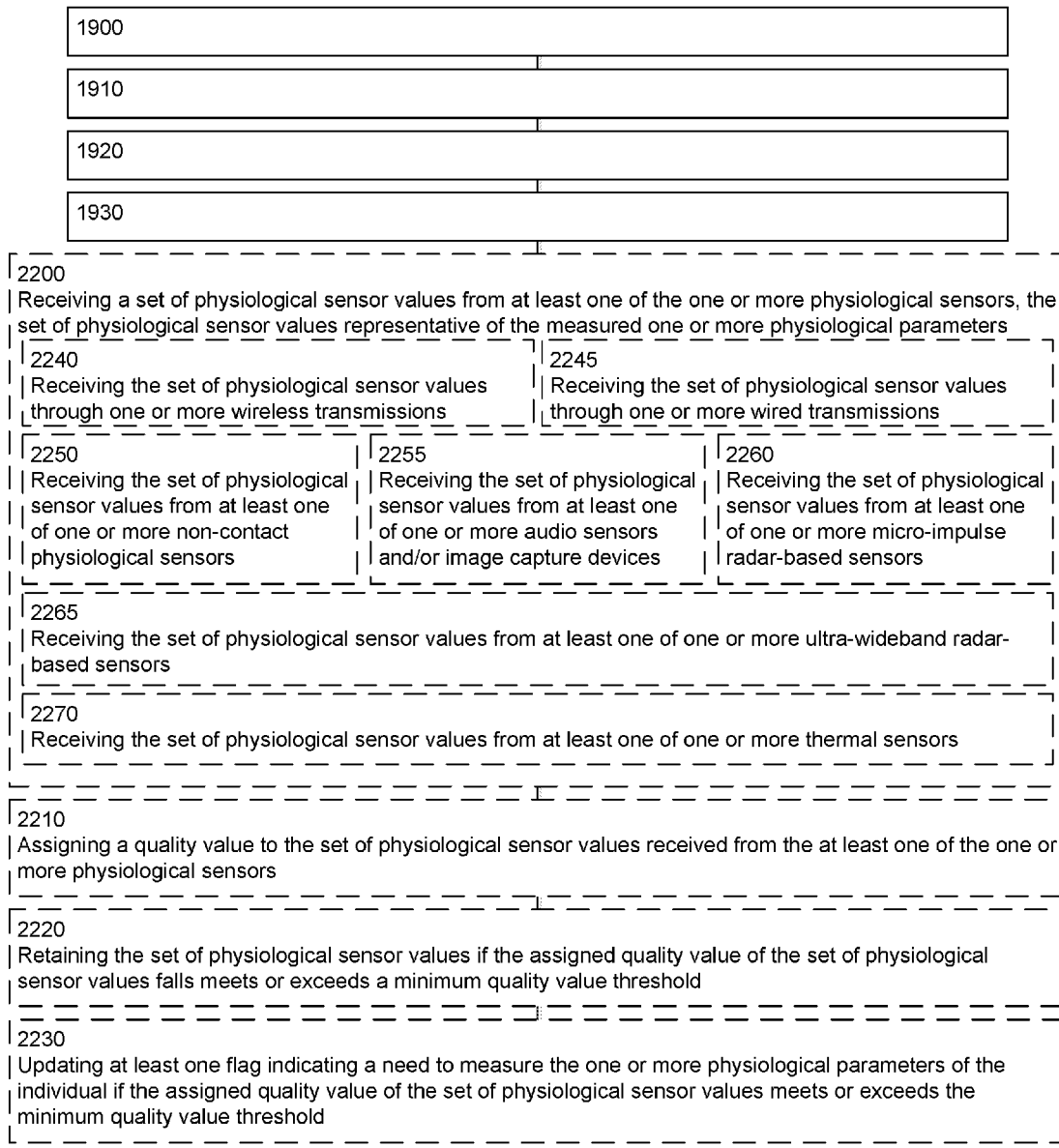
FIG. 22 is a flowchart depicting aspects of a method such as illustrated in FIG. 19.

FIG. 22 shows further aspects of the method shown in FIG. 19. In one embodiment, the method includes in block 2200 receiving a set of physiological sensor values from at least one of the one or more physiological sensors, the set of physiological sensor values representative of the measured one or more physiological parameters; block 2210 assigning a quality value to the set of physiological sensor values received from the at least one of the one or more physiological sensors; block 2220 retaining the set of physiological sensor values if the assigned quality value of the set of physiological sensor values meets or exceeds a minimum quality value threshold; and block 2230 updating at least one flag indicating a need to measure one or more physiological parameters of the individual if the assigned quality value of the set of physiological sensor values meets or exceeds the minimum quality value threshold. The method including block 2200 for receiving a set of physiological sensor values from at least one of one or more physiological sensors further optionally includes one or more of receiving the set of physiological sensor values through one or more wireless transmissions in block 2240; receiving the set of physiological sensor values through one or more wired transmissions in block 2245; receiving the set of physiological sensor values from at least one of one or more non-contract physiological sensors in block 2250; receiving the set of physiological sensor values from at least one of one or more audio sensors and/or image capture devices in block 2255; receiving the set of physiological sensor values from at least one of one or more micro impulse radar-based sensors in block 2260; receiving the set of physiological sensor values from at least one of one or more ultra-wideband radar-based sensors in block 2265; and/or receiving the set of physiological sensor values from at least one of one or more thermal sensors in block 2270.

Figure 23:
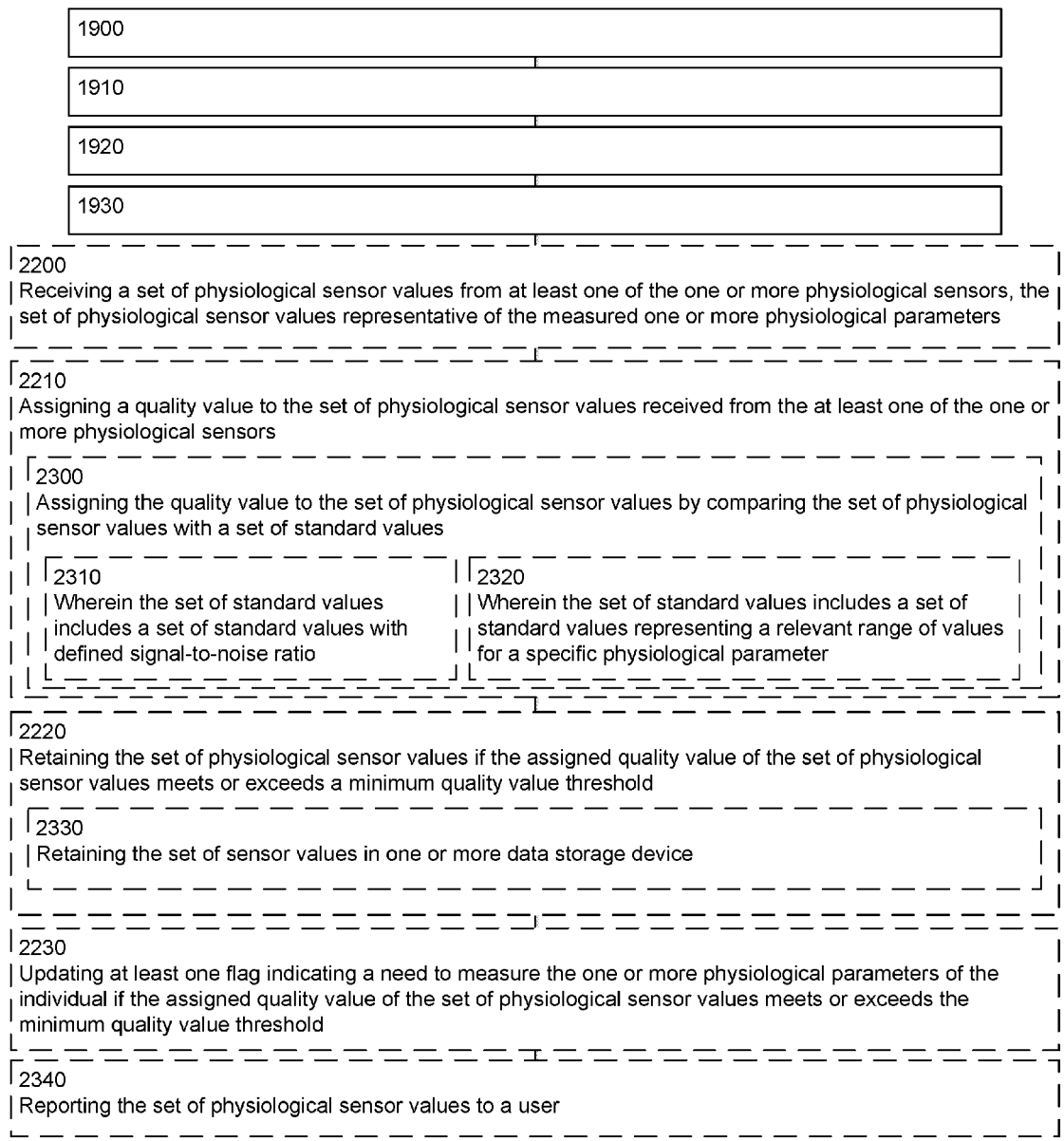
FIG. 23 is a flowchart illustrating aspects of a method such as shown in FIG. 19.

FIG. 23 illustrates further aspects of a method such as illustrated in FIG. 21. The method includes block 2210 assigning a quality value to the set of physiological sensor values received from the at least one of the one or more physiological sensors and optionally includes block 2300 assigning the quality value to the set of physiological sensor values by comparing the set of physiological sensor values with a set of standard values. In one embodiment, the set of standard values includes a set of standard values with defined signal-to-noise ratio, as illustrated in block 2310. In one embodiment, the set of standard values includes a set of standard values representing a relevant range of values for a specific physiological parameter, as illustrated in block 2320. In one embodiment, the set of standard values for use in comparing with the set of sensor values are stored in a computing device. In one embodiment, the set of standard values are stored in one or more lookup tables. In one embodiment, the one or more lookup tables including sets of standard values are pre-calculated and stored in a computing device, e.g., in static program storage or in hardware. In one embodiment, the one or more lookup tables including sets of standard values are calculated as part of programs or algorithms run on a computing device. In one embodiment, the set of standard values are specific for a given physiological parameter, e.g., a physiologically relevant range. In one embodiment, the set of standard values are specific to a given sensor type, e.g., the amount of noise and the value of data above the noise may be specific to a sensor type.

The method includes block 2220 retaining the set of physiological sensor values if the assigned quality value of the set of physiological sensor values meets or exceeds a minimum quality value threshold and optionally includes block 2330 retaining the set of sensor values in one or more data storage devices. Non-limiting examples of data storage devices have been described above herein. In one embodiment, the method further includes re-querying the one of more physiological sensors if the assigned quality value of the set of physiological sensor values fails to meet or exceed the minimum quality value threshold. In one embodiment, the method further includes re-querying the one or more physiological sensors until the assigned quality value of the set of physiological sensor values meets or exceeds the minimum quality value threshold.

Returning to FIG. 23, in one embodiment, a method such as shown in FIG. 21, optionally includes reporting the set of physiological sensor values to a user, as illustrated in block 2340. In one embodiment, reporting the set of sensor values to a user includes reporting the retained set of sensor values, i.e., sets of sensor values that meet or exceeded the minimum quality value threshold. In one embodiment, reporting the set of sensor values to the user includes reporting rejected sensor values, i.e., sets of sensor values that failed to meet or exceed the minimum quality value threshold. In one embodiment, reporting the set of sensor values to the user includes reporting the set of physiological sensor values to the user through a wireless communications means. In one embodiment, reporting the set of sensor values includes reporting the set of sensor values to the individual and/or a third party, e.g., a physician, nurse, clinic, or other caregiver. In one embodiment, reporting the set of sensor values includes reporting rejected sensor values to a system maintenance service. In one embodiment, the set of sensor values can be reported through a computing device accessible to the individual and/or third party. For example, the computing device, if set up in the residence of the individual, may be programmed to generate an onscreen report accessible by the individual. In one embodiment, the computing device is programmed to report a set of sensor values to a third party, e.g., physician, nurse, clinic, or other care provider. In one embodiment, reporting the set of sensor values includes transmitting the set of sensor values through a transmission means, e.g., a telephone or the Internet. In one embodiment, reporting the set of sensor values includes sending an audible alert or transmitting an alert to a handheld device, e.g., a cell phone or pager, indicating that a set of sensor values is available for viewing on a local device, e.g., a computing device. In one embodiment, reporting the set of sensor values includes sending the information to a handheld device, e.g., a cell phone. In one embodiment, reporting the set of sensor values includes reporting the set of sensor values through an e-mail message or alert. In one embodiment, reporting the set of sensor values includes generating a printout, e.g., a table or other graphic display, of the set of sensor values.

Figure 24:
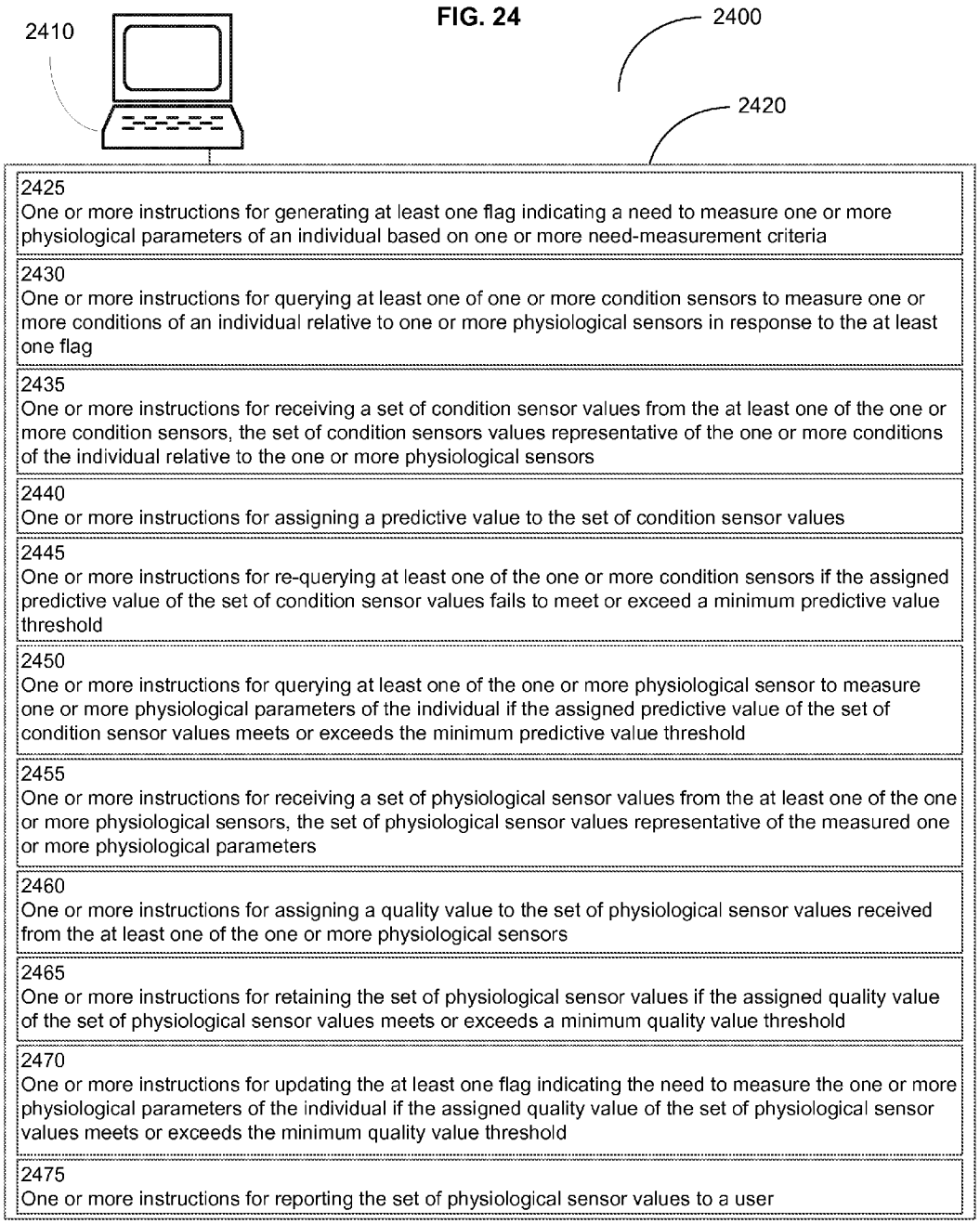
FIG. 24 is a schematic of a system for controlling acquisition of information from physiological sensors.

FIG. 24 illustrates a system for controlling acquisition of information from one or more physiological sensors. System 2400 includes computing device 2410 and non-transitory signal-bearing medium 2420. Non-transitory signal-bearing medium 2420 includes one or more instructions for controlling acquisition of information from one or more physiological sensors. Non-transitory signal-bearing medium 2420 includes one or more instructions 2425 for generating at least one flag indicating a need to measure one or more physiological parameter of an individual based on one or more need-measurement criteria; one or more instructions 2430 for querying at least one of one or more condition sensors to measure one or more conditions of the individual relative to one or more physiological sensors in response to the at least one flag; one or more instructions 2435 for receiving a set of condition sensor values from the at least one of one or more condition sensors, the set of condition sensor values representative of the one or more conditions of the individual relative to the one or more physiological sensors; one or more instructions 2440 for assigning a predictive value to the set of condition sensor values; one or more instructions 2445 for re-querying at least one of the one or more condition sensors if the assigned predictive value of the set of condition sensor values fails to meet or exceed a minimum predictive value threshold; one or more instructions 2450 for querying at least one of the one or more physiological sensors to measure the one or more physiological parameters of the individual if the assigned predictive value of the set of condition sensor values meets or exceeds the minimum predictive value threshold; one or more instructions 2455 for receiving a set of physiological sensor values from the at least one of the one or more physiological sensors, the set of physiological sensor values representative of the measured one or more physiological parameters; one or more instructions 2460 for assigning a quality value to the set of physiological sensor values received from the at least one of the one or more physiological sensors; one or more instructions 2465 for retaining the set of physiological sensor values if the assigned quality value of the set of physiological sensor values meets or exceeds a minimum quality value threshold; one or more instructions 2470 for updating the at least one flag indicating a need to measure the one or more physiological parameters of the individual if the assigned quality value of the set of physiological sensor values meets or exceeds the minimum quality value threshold; and one or more instructions 2475 for reporting the set of physiological sensor values to a user.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations can include software or other control structures. Electronic circuitry, for example, may have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

Those skilled in the art will recognize that at least a portion of the systems and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

Those skilled in the art will recognize that at least a portion of the systems and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

Those skilled in the art will recognize that at least a portion of the systems and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1

System and Method for Controllably Acquiring Information from Sensors in an Individual's Residence A system is described for controllably monitoring physiological parameters of an individual with heart failure unobtrusively in the individual's residence, e.g., an apartment in an assisted living facility. The system includes a computing device programmed to control operation of physiological sensors strategically placed in the individual's residence. In this example, the sensors are placed in the bedroom and in a room of the residence where the individual spends most of his or her waking hours, e.g., a living room/sitting room/TV room. The individual's physician develops a need-measurement criteria profile with a monitoring schedule to instruct acquisition of information from the various sensors in the individual's residence. The need-measurement criteria profile includes the types of sensors to be used and the timing of acquisition of information from each sensor type. The need-measurement criteria are either provided to the individual on a disk or USB drive or are automatically sent and loaded onto the individual's personal computer. In some instances, a caregiver, e.g., a home nurse who periodically visits the individual, may provide the need-measurement criteria for uploading on a portable data storage device. The sensors are configured to monitor weight, respiration sounds, gait, and snoring (associated with sleep apnea).

The computing device is a personal computer (e.g., Dell desktop computer from Dell Inc., Round Rock, Tex.) connected to the Internet and including a computer-controlled Wi-Fi relay switching system (e.g., ProXR Expandable Relay Controller with Wi-Fi Interface from National Control Devices, LLC, Oscelola, Mo.) for wirelessly switching the physiological sensors on and off in accordance with the monitoring schedule.

The system further includes a wireless audio/video camera mounted on the wall of the living room (e.g., Pan/Tilt Network Camera BB-HCM371A from Panasonic Panasonic Systems Communications Company of North America, Secaucus, N.J.). The audio/video camera is configured to capture information regarding respiration sounds, e.g., labored breathing, made by the individual. In some instances, the combination of audio and video may be useful for diagnosis, e.g., measuring labored breathing while the individual is walking and/or at rest. The audio/video camera is further configured to capture physical information regarding the individual, e.g., walking gait, stability, pallor/erythema, swelling, and general overall appearance.

The need-measurement criteria for the individual include flags that periodically activate the audio/video camera over the course of the individual's waking hours, e.g., from approximately 8 am to 8 pm. The flags are activated every 30-60 minutes and record data for 5 minutes. The audio/video data is assigned a quality value based on the signal-to-noise, e.g., audio resembling breathing recorded above background noise. If no breathing sound at all is detected in the recording, this may indicate that the individual is not present in the room, indicating that the quality value of the recorded data is low. The presence or absence of the individual in the room can be confirmed with the video recording. If the background sound is too loud, e.g., breathing sounds cannot be detected over the sound of a television, the data will be assigned a low quality value. Any given flag will remain active until audio recordings with quality values that meet or exceed the minimum quality value threshold are acquired.

The system further includes a scale for measuring the individual's weight. The scale is incorporated into and/or under a chair frequented by the individual and is automatically activated when the individual sits in the chair. However, the weight measurement is only processed by the computer if a flag indicating a need to take a weight measurement is activated. For weight, the flag is active first thing in the morning, e.g., the first time the individual sits down in the chair. The flag will remain active until a measurement is recorded and retained by the computer, assuming the measurement has a quality value that meets or exceeds the minimum quality value threshold (e.g., representing no change in weight or a physiologically feasible weight change for the individual since the last measurement approximately 24 hours before). In this way, if another individual of different weight, e.g., a spouse or a family pet, sits in the chair, the weight measurement will be deemed of low quality and not recorded and the flag will remain active until a weight measurement that meets or exceeds the minimum quality value threshold is acquired.

Another series of sensors are included in the sleeping area of the individual. The sensors include audio sensors for measuring snoring during sleep. Snoring is correlated with sleep apnea and can be monitored/assessed using audio recordings (see, e.g., Ghaemmaghami et al, *Conf Proc. IEEE Eng. Med. Biol. Soc.* (2009) 2009:5551-5554, which is incorporated herein by reference). Snoring detected in an individual who is using continuous positive airway pressure (CPAP) as therapy for sleep apnea may indicate a need to adjust the pressure on the CPAP equipment. One or more audio sensors (e.g., low noise microphones from Nady Systems, Emeryville, Calif.) are wirelessly connected to the personal computer. The computer is programmed to periodically activate the one or more microphones during the course of the night based on activation flags in the individual's schedule of need-measurement criteria. For analysis, at least ten 30 second audio clips are needed, requiring at least 10 activation flags during the course of the night. Each 30 second audio clip is given a quality value ranging from 0 to 100, where 100 is optimal. The assignment of the quality value is based on comparison of the recorded audio clip with a set of standard values. The assigned quality value is dependent on the volume of the recorded audio clip (e.g., too much noise or complete silence) or unrelated noise (e.g., the family pet barking or a siren passing by). A minimum quality value threshold is set at 50. If the quality of the audio clip is below 50, the flag remains activated and additional 30 seconds of audio are recorded. Repeated recording continues until 10 sets of 30 second audio clips with a quality value of 50 or higher are acquired.

The information from the various sensors that have assigned quality values that meet or exceed the minimum quality value threshold is retained. The retained set of sensor values is automatically reported to the individual's physician or other caregiver for analysis. Based on the information, the individual's physician may choose to alter the need-measurement criteria to acquire data more or less often or to alter the types of sensors that are being queried.

Prophetic Example 2

System and Method of Controllably Acquiring Sensor Information from an Individual Based on Condition of Individual Relative to the Sensors A system is described for controllably acquiring physiological sensor information from an individual in a residence based on the condition of the individual (e.g., movement and/or proximity) relative to the physiological sensors. The system includes a computing device, e.g., the individual's personal computer, programmed to control operation of condition sensors and physiological sensors strategically placed in the individual's residence. In this example, the sensors are placed in a room of the residence where the individual spends most of his or her waking hours, e.g., a living room/sitting room/TV room. The individual's physician or other caregiver develops a need-measurement criteria profile with a monitoring schedule to instruct acquisition of information from the various sensors in the individual's residence. The need-measurement criteria profile includes the types of sensors to be used, the timing of acquisition of information from each sensor type, and the minimum quality value thresholds for each sensor type. The need-measurement criteria are either provided to the individual on a disk or USB drive or are automatically sent and loaded onto the individual's personal computer. The computing device is programmed to control the physiological sensors based on feedback from the condition sensors. Acquisition of physiological sensor values is further dictated by the need-measurement criteria prescribed by the individual's physician or other caregiver.

The system includes a motion detector (e.g., MS13 RF Motion Detector from Marmitek BV, Eindhoven, The Netherlands) configured to wirelessly send a signal to a receiver, e.g., associated with the computing device, to indicate movement in the monitored region. The motion detector detects whether an individual has entered a room. If a flag is active indicating a need to measure a physiological parameter, e.g., breathing sounds, a physiological sensor, e.g., a stand-alone microphone or microphone associated with a video camera is queried. A sensor system for detecting disordered breathing is described (see, e.g., U.S. Pat. No. 7,396,333, which is incorporated herein by reference). If a flag is not active, then the physiological sensor is not queried in response to the trigger from the motion detector.

In some instances, the physiological sensor may only be activated if the individual is close enough to the physiological sensor. The motion detector detects that the individual has entered the room and sends a wireless signal to activate a proximity sensor (e.g., ULTRA-U ultrasonic proximity sensor from Senix Corp., Hinesburg, Vt.). The proximity sensor in turn measures the distance between the individual and the physiological sensor and transmits this information to the computer. The computer includes programming to assign a predictive value to the measurement based on the predicted quality of data from the physiological sensor relative to the distance to the individual. For example, the best data may be obtained at 1 meter from the physiological sensor, with lesser quality data as the distance gets larger, such that a relative predictive value of 100 is given to proximity sensor value indicating the individual is 1 meter from the physiological sensor, a relative predictive value of 80 if the individual is 2 meters from the physiological sensor, a relative predictive value of 60 if the individual is 3 meters from the physiological sensor, and so on. A minimum predictive value threshold is set, e.g., at 50, based on the sensor type and the needs of the individual. If the minimum predictive value threshold is met or exceeded, i.e., the individual is an appropriate distance from a given physiological sensor, the sensor is triggered, assuming that a flag indicating a need to do so is active. If the minimum predictive value threshold is not met, i.e., the individual is not an appropriate distance from a given physiological sensor, the sensor is not triggered, even if a flag to do so is active. The computer is programmed to re-query the condition sensor to update information on where the individual is relative to the physiological sensor.

A micro impulse radar-based sensor is queried in response to a flag indicating a need to unobtrusively measure the heart rate of the individual. The micro impulse radar-based sensor is incorporated into a wall or piece of furniture in the individual's residence, preferably in a location that the individual frequents on a daily basis and remains relatively still, e.g., a favorite chair or in front of a bathroom mirror. The micro impulse radar-based sensor is only queried if the predictive value of the condition sensor values related to proximity and motion meet the minimum predictive value threshold. For example, a proximity value of 1 meter may be given a predictive value of 20 for this particular sensor type, while a proximity value of 15 centimeters may be given a predictive value of 100. A predictive value threshold of 50 would indicate that if the individual is standing 1 meter away from the micro impulse radar-based sensor, the sensor would not be queried until the individual moved closer so as to optimize data acquired from the sensor. In addition, radar senses body movement in general in addition to movement of the heart. As such, more movement would predict lower quality data from the radar-based sensor. In addition, multiple queries to the micro impulse radar-based sensor may be needed to acquire sensor values that meet the minimum quality value threshold, e.g., interpretable heart rate data, because different distances and placements may require adjustments to the delay-line. A micro impulse radar system for detecting heart rate and a discussion of parameter tuning are described (see, e.g., Michahelles et al., (2004) *Proceedings of the Eighth International Symposium on Wearable Computers* (ISWC'04) 1530-0811/04, which is incorporated herein by reference).

The retained physiological sensor values are reported to both the individual and the individual's physician on a daily basis. The individual's personal computer emits an audible alert indicating that a report including the physiological sensor values are available for viewing. The reporting may include a graphic that shows the trend of physiological sensor values over a given time frame, e.g., a 24 hour period or a 7 day period. Similar information is also transmitted through the Internet to the individual's physician. The physician may also receive a report of how often any given sensor in the system failed to acquire physiological sensor values that met the minimum quality value threshold as an indication of how well the system is working and whether repair or replacement of sensors is needed.

Prophetic Example 3

System and Method for Controllably Acquiring Sensor Information from Multiple Individuals in a Group Home Setting A system is described for controlling acquisition of sensor information from multiple individuals in a residential space, e.g., a group home. The system includes a centralized desktop computer in a secure portion of the group home, e.g., in an office of the group home, that is monitored by group home staff. The centralized desktop computer is operably connected to sensors throughout the common rooms of the group home, e.g., a sitting room/TV room and/or a dining room. The connection between the computer and the sensors is facilitated through both wireless and/or wired communication to a central control box, e.g., a switch box, connected to and controlled by the computing device. The physiological sensors include sensors imbedded or mounted on the walls and incorporated into furniture in the common rooms.

Each individual in the group home has his or her individual monitoring schedule including need-measurement criteria. The monitoring schedules including the need-measurement criteria for each individual are downloaded into the centralized desktop computer, either from a portable data means, e.g., a USB drive, or from an Internet communication between the computer and one or more prescribing physicians and/or caregivers. Each of the need-measurement criteria include the types of sensors that need to be queried, the frequency at which each sensor type needs to be queried over a given time frame, and the minimum quality value thresholds for each sensor type. Individualized flags indicating a need to measure a specific physiological parameter are generated based on each individual's need-measurement criteria.

The system includes at least one video camera for use in real-time identification of each individual residing in the group home (e.g., iPro SmartHD system Real Time Face Matching function from Panasonic Systems Communications Company of North America, Secaucus, N.J.). A motion detector (e.g., Next® PG2 wireless digital passive infrared (PIR) detector, from Visonic, Ltd., Tel Aviv, Israel) is used to trigger activation of the video camera when someone enters the room. The recorded images are assigned a predictive value based on the quality of the information. For facial recognition, the predictive value may be assigned based on lighting, shadows, shading, face position in terms of skew, orientation, translation, facial expressions, and changes in facial hair, hair styles, weight, or eye wear. The facial recognition software running on the computer determines if the individual is part of the group of individuals being monitored by the system and if so looks to see if there are any active flags associated with the identified individual. If there are active flags, the appropriate set of physiological sensors in the common room are activated according to the individual's specific need-measurement criteria. A proximity sensor, as described above, may also be used to determine if the identified individual is in an optimal position relative to the physiological sensors to generate quality data.

The chairs and walls in either the community room or dining room of the group home are equipped with a variety of physiological sensors configured to measure various physiological parameters of an identified individual based on the individual's specific need-measurement criteria. Sensors associated with the chairs are in wireless communication with the centralized computer and are queried based on the identity of the individual and any associated flags. For example, the chairs may be configured to assess weight, electrocardiogram, heart rate, and respiration rate as necessary for an identified individual and wirelessly transmit the acquired physiological sensor values to the centralized computer. An electronic scale associated with a chair is queried in response to a flag indicating a need for a weight measurement. Electric potential sensors position 1 meter apart on opposite sides of the chair are queried in response to a flag indicating a need for an electrocardiogram. Non-conductive electric potential sensors to determine an individual's electrocardiogram are described (see, e.g., Harland et al., *Meas. Sci. Technol.* (2002) 13:163-169, which is incorporated herein by reference). Sensors built into the back of the chair including a source of radio frequency electromagnetic signals and a means to detect reflected electromagnetic signal waves are queried in response to a flag indicating a need for respiration rate and heart rate. A remote sensor to detect respiration and heart rate are described (see, e.g., U.S. Pat. No. 7,272,431, which is incorporated herein by reference). Sensors associated with the walls are in wireless and/or wired communication with the centralized computer and include audio/video equipment, infrared cameras, micro-impulse radar-based sensors, and/or ultra-wideband radar-based sensors. For example, an infrared camera installed in the wall is queried in response to a flag indicating a need to measure a body temperature of an identified individual. Devices and methods to determine core body temperature remotely are described (see, e.g., U.S. Pat. No. 7,340,293, which is incorporated herein by reference). An ultra-wide band (UWB) sensor consisting of antennas and a kilohertz pulser associated with the wall is queried in response to a flag indicating a need to measure a respiration rate and/or heart rate of an identified individual. A system for UWB monitoring of heart and respiration rate of multiple individuals simultaneously is described (see, e.g., Rivera et al., "Multi-target estimation of heart and respiration rates using ultra wideband sensors," European Signal Processing Conference, Sep. 4-8, 2006, Florence, Italy, which is incorporated herein by reference).

The acquired physiological sensor values are transmitted to the centralized computing device and assigned a quality value. If the assigned quality value meets or exceeds the minimum quality value threshold, the values are retained and the status of the flag is updated. If the assigned quality value does not meet or exceed the minimum quality value threshold, the flag remains active and the condition sensors and/or the physiological sensors are re-queried. The retained physiological sensor values are reported to an individual's respective physician or other caregiver and any adjustments to the need-measurement criteria are made and transmitted back to the centralized computer.

All of the above U.S. patents, U.S. patent application publications, U.S. Patent applications, foreign patents, foreign patent applications and non-patent publications referred to in this specification and/or listed in any Information Disclosure Statement, are incorporated herein by reference, to the extent not inconsistent herewith.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A system, comprising:
 a network of sensors including
  one or more physiological sensors configured to sense a physiological parameter of an individual; and one or more condition sensors configured to sense a position of the individual relative to the one or more physiological sensors; and a computing device operably connected to the one or more condition sensors and the one or more physiological sensors, the computing device including a processor programmed to query at least one of the one or more condition sensors to initiate measurement of the position of the individual relative to the one or more physiological sensors;

receive a set of condition sensor values from the at least one of the one or more condition sensors, the set of condition sensor values representative of the position of the individual relative to the one or more physiological sensors;

query at least one of the one or more physiological sensors to measure the physiological parameter of the individual if the set of condition sensor values meets or exceeds a threshold value; and re-query at least one of the one or more condition sensors if the set of condition sensor values fails to meet or exceed the threshold value.

2. The system of claim 1, wherein at least one of the one or more condition sensors includes at least one transmission unit including an antenna configured for wireless communication with the computing device.

3. The system of claim 1, wherein the one or more physiological sensors include one or more non-contact physiological sensors.

4. The system of claim 1, wherein the one or more physiological sensors include one or more micro impulse radar-based sensors.

5. The system of claim 1, wherein at least one of the one or more physiological sensors is configured to detect one or more physiological parameters of the individual diagnostic for heart failure.

6. The system of claim 1, wherein at least one of the one or more physiological sensors includes at least one transmission unit including an antenna configured for wireless communication with the computing device.

7. The system of claim 1, wherein the computing device is programmed to query the at least one of the one or more condition sensors to initiate measurement of one or more position parameters including proximity, visibility, line-of-sight, motion, or acceleration of the individual relative to the one or more physiological sensors.

8. The system of claim 1, wherein the computing device is programmed to query the at least one of the one or more condition sensors in response to a triggering event.

9. The system of claim 1, wherein the computing device is programmed to query the at least one of the one or more condition sensors to initiate measurement of the position of the individual relative to the one or more physiological sensors in response to a flag indicating a need to measure the physiological parameter of the individual based on one or more need-measurement criteria.

10. The system of claim 1, wherein the threshold value for a set of condition sensor values is represented as a position of the individual relative to the one or more physiological sensors sufficient to acquire a set of physiological sensor values from the one or more physiological sensors.

11. The system of claim 1, wherein the computing device is programmed to query the at least one of the one or more physiological sensors to measure the physiological parameter of the individual if the set of condition sensor values meets or exceeds the threshold value and at least one flag indicating a need to measure the physiological parameter of the individual is active based on one or more need-measurement criteria.

12. The system of claim 11, wherein the one or more need-measurement criteria include a number of queries needed over time for a reliable diagnosis.

13. The system of claim 1, wherein the computing device including the processor is further programmed to receive a set of physiological sensor values from at least one of the one or more physiological sensors, the set of physiological sensor values representative of the measured physiological parameter of the individual;

assign a quality value to the set of physiological sensor values received from the at least one of the one or more physiological sensors;

retain the set of physiological sensor values if the assigned quality value of the set of physiological sensor values meets or exceeds a minimum quality value threshold; and update at least one flag indicating a need to measure the physiological parameter of the individual if the assigned quality value of the set of physiological sensor values meets or exceeds the minimum quality value threshold.

14. The system of claim 13, wherein the computing device is programmed to assign the quality value to the set of physiological sensor values by comparing the set of physiological sensor values with a set of standard values.

15. The system of claim 13, wherein the computing device including the processor is further programmed to report the set of physiological sensor values to a user.

16. A method for controlling acquisition of information from a network of one or more sensors comprising:

receiving a set of condition sensor values for an individual from at least one of one or more condition sensors in response to one or more queries, the set of condition sensor values representative of a position of the individual relative to one or more physiological sensors;

querying at least one of the one or more physiological sensors to measure a physiological parameter of the individual if the the set of condition sensor values meets or exceeds a threshold value; and re-querying at least one of the one or more condition sensors if the set of condition sensor values fails to meet or exceed the threshold value.

17. The method of claim 16, further comprising:

querying the at least one of the one or more condition sensors to measure the position of the individual relative to the one or more physiological sensors.

18. The method of claim 17, wherein querying the at least one of the one or more condition sensors includes querying the at least one of the one or more condition sensors in response to a triggering event.

19. The method of claim 17, wherein querying the at least one of the one or more condition sensors includes querying the at least one of the one or more condition sensors in response to at least one flag indicating a need to measure the physiological parameter of the individual.

20. The method of claim 19, wherein the at least one flag indicating the need to measure the physiological parameter of the individual is generated based on one or more need-measurement criteria.

21. The method of claim 16, wherein querying the at least one of the one or more physiological sensors includes querying the at least one of the one or more physiological sensors through one or more wireless transmissions.

22. The method of claim 16, wherein querying the at least one of the one or more physiological sensors includes querying at least one of one or more non-contact physiological sensors.

23. The method of claim 16, wherein querying the at least one of the one or more physiological sensors includes querying at least one of one or more micro impulse radar-based sensors.

24. The method of claim 16, wherein querying the at least one of one or more physiological sensors to measure the physiological parameter of the individual includes querying the at least one of the one or more physiological sensors to measure a physiological parameter of the individual diagnostic for heart failure.

25. The method of claim 16, wherein re-querying the at least one of the one or more condition sensors includes re-querying at least one of the one or more condition sensors until the set of condition sensor values meets or exceeds the threshold value.

26. The method of claim 16, further comprising:
receiving a set of physiological sensor values from the at least one of the one or more physiological sensors, the set of physiological sensor values representative of the measured physiological parameter of the individual;
assigning a quality value to the set of physiological sensor values received from the at least one of the one or more physiological sensors;
retaining the set of physiological sensor values if the assigned quality value of the set of physiological sensor values meets or exceeds a minimum quality value threshold; and
updating at least one flag indicating a need to measure the physiological parameter of the individual if the assigned quality value of the set of physiological sensor values meets or exceeds the minimum quality value threshold.

27. The method of claim 26, wherein receiving the set of physiological sensor values from the at least one of the one or more physiological sensors includes receiving the set of physiological sensor values through one or more wireless transmissions.

28. The method of claim 26, wherein receiving the set of physiological sensor values from the at least one of the one or more physiological sensors includes receiving the set of physiological sensor values from at least one of one or more non-contact physiological sensors.

29. The method of claim 26, wherein receiving the set of physiological sensor values from the at least one of the one or more physiological sensors includes receiving the set of physiological sensor values from at least one of one or more micro impulse radar-based sensors.

30. The method of claim 26, wherein assigning the quality value to the set of physiological sensor values includes assigning the quality value to the set of physiological sensor values by comparing the set of physiological sensor values with a set of standard values.

31. The method of claim 30, wherein the set of standard values includes a set of standard values representing a relevant range of values for a specific physiological parameter.

32. The method of claim 26, further comprising:
reporting the set of physiological sensor values to a user.

33. A system comprising:
a computing device including a processor; and
non-transitory signal-bearing medium bearing one or more instructions for controlling acquisition of information from a network of one or more sensors, the non-transitory signal-bearing medium including one or more instructions for generating at least one flag indicating a need to measure a physiological parameter of an individual based on one or more need-measurement criteria;
one or more instructions for querying at least one of one or more condition sensors to measure a position of the individual relative to one or more physiological sensors in response to the at least one flag;
one or more instructions for receiving a set of condition sensor values from the at least one of the one or more condition sensors, the set of condition sensor values representative of the position of the individual relative to the one or more physiological sensors;
one or more instructions for re-querying at least one of the one or more condition sensors if the set of condition sensor values fails to meet or exceed a threshold value;
one or more instructions for querying at least one of the one or more physiological sensors to measure the physiological parameter of the individual if the set of condition sensor values meets or exceeds the threshold value;
one or more instructions for receiving a set of physiological sensor values from the at least one of the one or more physiological sensors, the set of physiological sensor values representative of the measured physiological parameter of the individual;
one or more instructions for assigning a quality value to the set of physiological sensor values received from the at least one of the one or more physiological sensors;
one or more instructions for retaining the set of physiological sensor values if the assigned quality value of the set of physiological sensor values meets or exceeds a minimum quality value threshold;
one or more instructions for updating the at least one flag indicating the need to measure the physiological parameter of the individual if the assigned quality value of the set of physiological sensor values meets or exceeds the minimum quality value threshold; and
one or more instructions for reporting the set of physiological sensor values to a user.

34. The system of claim 1, wherein the one or more condition sensors include one or more motion sensors, proximity sensors, contact sensors, or image capture devices.

35. The system of claim 1, further comprising:
at least one biometric sensor operably coupled to the computing device and configured to assess the identity of the individual relative to the one or more physiological sensors.

36. The system of claim 8, wherein the triggering event includes input from at least one of a motion detector, a timing device, a light sensor, or a proximity sensor.

37. The system of claim 10, wherein the threshold value for the set of condition sensor values is represented as a position of the individual relative to the one or more physiological sensors sufficient to acquire an optimal set of physiological sensor values from the one or more physiological sensors.

38. The system of claim 11, wherein the one or more need-measurement criteria includes at least one of a time of day and an interval of time since a previous measurement.

39. The method of claim 16, wherein receiving the set of condition sensor values for the individual from the at least one of the one or more condition sensors includes receiving the set of condition sensor values from at least one of a motion sensor, a proximity sensor, or a contact sensor.

* * * * *